United States Patent
Hull et al.

(10) Patent No.: US 6,479,666 B2
(45) Date of Patent: Nov. 12, 2002

(54) PHENYL-KETO-IMIDAZOLIDINE THIOAMIDE DERIVATIVES

(75) Inventors: Kenneth Gregory Hull, Marlborough, MA (US); Achytharao Sidduri, Livingston, NJ (US); Jefferson Wright Tilley, North Caldwell, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/863,567

(22) Filed: May 23, 2001

(65) Prior Publication Data

US 2002/0010338 A1 Jan. 24, 2002

(51) Int. Cl.⁷ .................... C07D 233/02; C07D 241/10; C07D 403/12; C07D 401/12

(52) U.S. Cl. .................. 548/300.1; 548/311.1; 548/314.7; 546/272.7; 544/171; 544/263

(58) Field of Search ............... 548/300.1, 311.1, 548/314.7, 112; 546/184, 250, 255, 268.1, 272.7; 544/171, 263; 514/359, 385, 396, 397, 398, 400

(56) References Cited

U.S. PATENT DOCUMENTS 6,229,011 B1 * 5/2001 Chen et al. ................. 544/171

* cited by examiner

Primary Examiner—Alan L. Rotman
Assistant Examiner—Rita Desai
(74) Attorney, Agent, or Firm—George W. Johnston; Dennis P. Tramaloni

(57) ABSTRACT

It has been discovered that compounds of the formula:

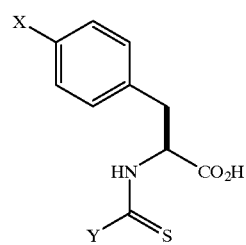

and the pharmaceutically acceptable salts and esters thereof wherein X and Y are as defined below, inhibit the binding of VCAM-1 to VLA-4 and are useful in treating inflammation associated with chronic inflammatory diseases such as rheumatoid arthritis (RA), multiple sclerosis, (MS), asthma, and inflammatory bowel disease (I BD).

21 Claims, No Drawings

PHENYL-KETO-IMIDAZOLIDINE THIOAMIDE DERIVATIVES

BACKGROUND OF THE INVENTION

Vascular cell adhesion molecule-1 (VCAM-1), a member of the immunoglobulin (Ig) supergene family, is expressed on activated, but not resting, endothelium. The integrin VLA-4 ($a_4b_1$), which is expressed on many cell types including circulating lymphocytes, eosinophils, basophils, and monocytes, but not neutrophils, is the principal receptor for VCAM-1. Antibodies to VCAM-1 or VLA-4 can block the adhesion of these mononuclear leukocytes, as well as melanoma cells, to activated endothelium in vitro. Antibodies to either protein have been effective at inhibiting leukocyte infiltration and preventing tissue damage in several animal models of inflammation. Anti-VLA-4 monoclonal antibodies have been shown to block T-cell emigration in adjuvant-induced arthritis, prevent eosinophil accumulation and bronchoconstriction in models of asthma, and reduce paralysis and inhibit monocyte and lymphocyte infiltration in experimental autoimmune encephalitis (EAE). Anti-VCAM-1 monoclonal antibodies have been shown to prolong the survival time of cardiac allografts. Recent studies have demonstrated that anti-VLA-4 mAbs can prevent insulitis and diabetes in non-obese diabetic mice, and significantly attenuate inflammation in the cotton-top tamarin model of colitis.

Thus, compounds which inhibit the interaction between $\alpha_4$-containing integrins and VCAM-1 will be useful as therapeutic agents for the treatment of inflammation resulting from chronic inflammatory diseases such as rheumatoid arthritis, multiple sclerosis (MS), asthma, and inflammatory bowel disease (IBD).

CROSS REFERENCE TO RELATED APPLICATIONS

This application is related to:

Chen, et al. U.S. Ser. No. 09/138,353 filed Aug. 21, 1998, Title: N-ALKANOYLPHENYLALANINE DERIVATIVES; and Chen, et al. U.S. Ser. No. 09/137,798 filed Aug. 21, 1998, Title: N-AROYLPHENYLALANINE DERIVATIVES.

SUMMARY OF THE INVENTION

It has been discovered that compounds of the formula:

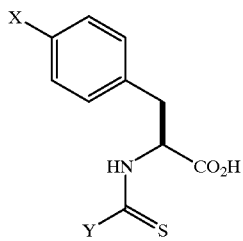

1 and the pharmaceutically acceptable salts and esters thereof wherein X and Y are as defined below, inhibit the binding of VCAM-1 to VLA-4 and are useful in treating inflammation associated with chronicinflammatory diseases such as rheumatoid arthritis (RA), multiple sclerosis, (MS), asthma, and inflammatory bowel disease (I BD).

DETAILED DESCRIPTION OF THE INVENTION

The present invention is directed to the discovery that compounds of the formula:

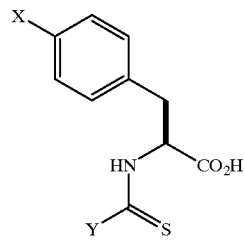

1 and the pharmaceutically acceptable salts and esters thereof, inhibit the binding of VCAM-1 to VLA-4 and are useful in treating inflammation associated with chronic inflammatory diseases such as rheumatoid arthritis (RA), multiple sclerosis, (MS), asthma, and inflammatory bowel disease (I BD).

In accordance with the invention, X is a group X-1, X-2 or X-3 as described below. Y is a group Y-1, Y-2 or Y-3 as described below.

The group X-1 is of the formula:

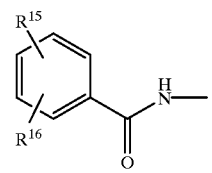

X-1 wherein:

$R_{15}$ is halogen, nitro, lower alkyl sulfonyl, cyano, lower alkyl, lower alkoxy, lower alkoxycarbonyl, carboxy, lower alkyl aminosulfonyl, perfluorolower alkyl, lower alkylthio, hydroxy lower alkyl, alkoxy lower alkyl, lower alkylthio lower alkyl, lower alkylsulfinyl lower alkyl, lower alkylsulfonyl lower alkyl, lower alkylsulfinyl, lower alkanoyl, aroyl, aryl, aryloxy;

$R_{16}$ is hydrogen, halogen, nitro, cyano, lower alkyl, OH, perfluorolower alkyl, or lower alkylthio.

The groups $R_{15}$ and $R_{16}$ are preferably independently hydrogen, lower alkyl, nitro, halogen (especially chloro or fluoro), perfluoromethyl, or cyano for $R_{16}$, and lower alkyl, nitro, halogen (especially chloro or fluoro), perfluoromethyl, or cyano for $R_{15}$.

It is preferred that groups selected as $R_{15}$, or $R_{15}$ and $R_{16}$, be electron-deficient as defined below.

X-2 is a group of the formula:

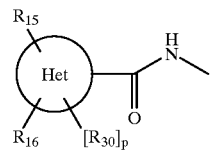

X-2 wherein Het is a 5- or 6-membered heteroaromatic ring containing 1, 2 or 3 heteroatoms selected from N, O, and S, or Het is a 9- or 10-membered bicyclic heteroaromatic ring containing 1, 2, 3 or 4 heteroatoms selected from O, S, and N;

$R_{15}$ and $R_{16}$ are as above, and $R_{30}$ is hydrogen or lower alkyl; and p is an integer from 0 to 1.

Het is preferably a 5- or 6-membered monocyclic heteroaromatic ring containing 1, 2 or 3 nitrogens, or a nitrogen and a sulfur, or a nitrogen and an oxygen. When Het is a bicyclic heteroaromatic ring, it preferably contains from 1 to 3 nitrogens as the heteroatoms. $R_{15}$ is preferably, nitro, lower alkyl sulfonyl, cyano, lower alkyl, lower alkoxy, perfluorolower alkyl, lower alkylthio, lower alkanoyl, or aryl (especially unsubstituted phenyl); $R_{16}$ is preferably hydrogen, halogen, nitro, cyano, lower alkyl, perfluoro lower alkyl; and $R_{30}$, when present, is preferably hydrogen or lower alkyl.

The group X-3 is of the formula:

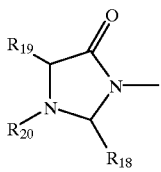

wherein:
$R_{18}$ is aryl, heteroaryl,
$R_{19}$ is substituted or unsubstituted lower alkyl, aryl, heteroaryl, arylalkyl, heteroaryl alkyl, and
$R_{20}$ is substituted or unsubstituted lower alkanoyl or aroyl
  $R_{18}$ is preferably phenyl. $R_{19}$ is preferably lower alkyl, which is unsubstituted or substituted by pyridyl or phenyl. $R_{20}$ is preferably lower alkanoyl
Y is a group of formula Y-1, Y-2, or Y-3 wherein:
  Y-1 is a group of the formula:

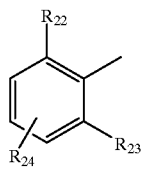

wherein:
$R_{22}$ and $R_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen, and
$R_{24}$ is hydrogen, lower alkyl, lower alkoxy, aryl, nitro, cyano, lower alkyl sulfonyl, or halogen Y-2 is a group of the formula

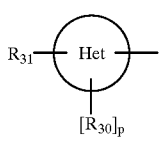

Het is a five or six membered heteroaromatic ring bonded via a carbon atom wherein said ring contains one, two or three heteroatoms selected from the group consisting of N, O and S and $R_{30}$ and $R_{31}$, are independently hydrogen, lower alkyl, cycloalkyl, halogen, cyano, perfluoroalkyl, or aryl and at least one of $R_{30}$ and $R_{31}$, is adjacent to the point of attachment, p is an integer of from 0 to 1.

Y-3 is a 3–7 membered ring of the formula:

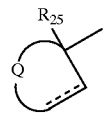

wherein:
$R_{25}$ is lower alkyl, unsubstituted or fluorine substituted lower alkenyl, or a group of formula $R_{26}$—$(CH_2)_e$—, $R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula —$NR_{28}R_{29}$, wherein
  $R_{28}$ is H or lower alkyl,
  $R_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylamninocarbonyl, or
  $R_{28}$ and $R_{29}$ taken together form a 4, 5 or 6-membered saturated carbocyclic ring optionally containing one heteroatom selected from O, S, and N with the carbon atoms in the ring being unsubstituted or substituted by lower alkyl or halogen,
Q is —$(CH_2)_fO$—, —$(CH_2)_fS$—, —$(CH_2)_fN(R_{27})$—, or —$(CH_2)_f$—,
$R_{27}$ is H, lower alkyl, aryl, lower alkanoyl, aroyl or lower alkoxycarbonyl,
e is an integer from 0 to 4, and f is an integer from 0 to 3; the dotted bond is optionally hydrogenated.

This invention is directed to a compound of the formula:

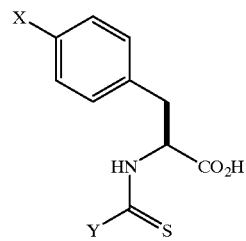

wherein X is a group of the formula

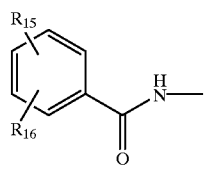

wherein:
$R_{15}$ is halogen, nitro, lower alkyl sulfonyl, cyano, lower alkyl, lower alkoxy, lower alkoxycarbonyl, carboxy, lower alkyl aminosulfonyl, perfluorolower alkyl, lower alkylthio, hydroxy lower alkyl, alkoxy lower alkyl, lower alkylthio lower alkyl, lower alkylsulfinyl lower alkyl, lower alkylsulfonyl lower alkyl, lower alkylsulfinyl, lower alkanoyl, aroyl, aryl, aryloxy;
$R_{16}$ is hydrogen, halogen, nitro, cyano, lower alkyl, OH, perfluorolower alkyl, or lower alkylthio;

or
X is a group of formula X-2

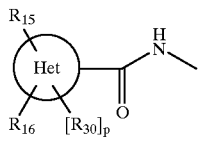

wherein Het is a 5- or 6-membered heteroaromatic ring containing 1, 2 or 3 heteroatoms selected from N, O, and S, or
Het is a 9- or 10-membered bicyclic heteroaromatic ring containing 1, 2, 3 or 4 heteroatoms selected from O, S, and N;
$R_{15}$ and $R_{16}$ are as above;
$R_{30}$ is hydrogen or lower alkyl; and p is an integer from 0 to 1
or X is a group of formula X-3

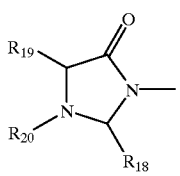

wherein:
$R_{18}$ is aryl, heteroaryl, aryl lower alkyl, heteroaryl lower alkyl
$R_{19}$ is substituted or unsubstituted lower alkyl, aryl, heteroaryl, arylalkyl, heteroaryl alkyl, and
$R_{20}$ is substituted or unsubstituted lower alkanoyl or aroyl;
and Y is a group of formula Y-1

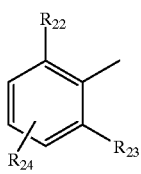

wherein:
$R_{22}$ and $R_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen, and
$R_{24}$ is hydrogen, lower alkyl, lower alkoxy, aryl, nitro, cyano, lower alkyl sulfonyl, or halogen;
or Y-2 is a group of the formula:

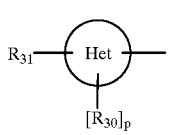

Het is a five or six membered heteroaromatic ring bonded via a carbon atom wherein said ring contains one, two or three heteroatoms selected from the group consisting of N, O and S and $R_{30}$ and $R_{31}$ are independently hydrogen, lower alkyl, cycloalkyl, halogen, cyano, perfluoroalkyl, or aryl and at least one of $R_{30}$ and $R_{31}$ is adjacent to the point of attachment; p is an integer of from 0 to 1;
or Y is a group of formula Y-3

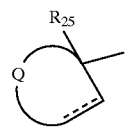

wherein:
$R_{25}$ is lower alkyl, unsubstituted or fluorine substituted lower alkenyl, or a group of formula $R_{26}-(CH_2)_e-$, $R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula $-NR_{28}R_{29}$,
wherein
$R_{28}$ is H or lower alkyl,
$R_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylaminocarbonyl, or $R_{28}$ and $R_{29}$ taken together form a 4, 5 or 6-membered saturated carbacyclic ring optionally containing one heteroatom selected from O, S, and N; with the carbon atoms in the ring being unsubstituted or substituted by lower alkyl or halogen,
Q is $-(CH_2)_fO-$, $-(CH_2)_fS-$, $-(CH_2)_fN(R_{27})-$, or $-(CH_2)_f-$,
$R_{27}$ is H, lower alkyl, aryl, lower alkanoyl, aroyl or lower alkoxycarbonyl,
e is an integer from 0 to 4, and
f is an integer from 0 to 3; and the dotted bond is optionally hydrogenated;
and pharmaceutically acceptable salts and esters thereof.
Preferred compounds are as follows:
Compounds where X is a group of the formula

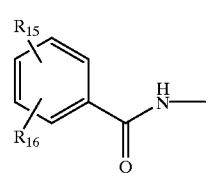

and Y, $R_{15}$ and $R_{16}$ are as in formula 1.
Such compounds where $R_{15}$ is lower alkyl, nitro, halogen, perfluoromethyl, or cyano and $R_{16}$ is hydrogen, lower alkyl, nitro, halogen, perfluoromethyl, or cyano, especially where $R_{15}$ and $R_{16}$ are independently chloro or fluoro are preferred, especially where X-1 is selected from the group of

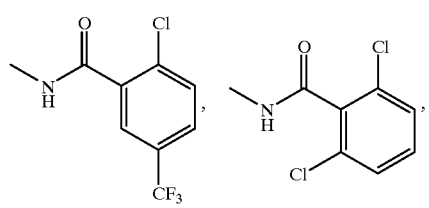

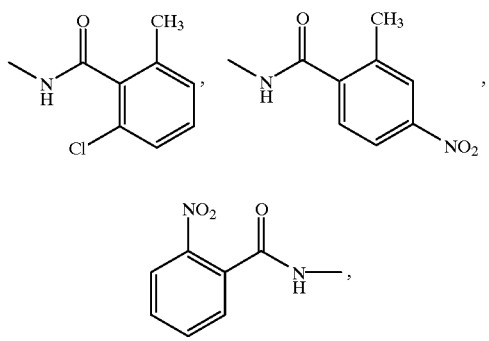

and

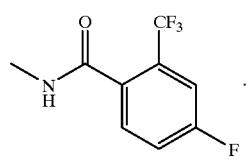

Compounds of formula 1 wherein X is a group of the formula X-2

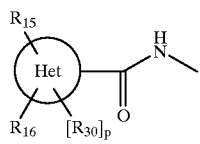

X-2 and p, Y, $R_{15}$, $R_{16}$, and $R_{30}$ are as in formula 1 (compound A) especially where Het is a 5-or 6-membered monocyclic heteroaromatic ring containing 1, 2 or 3 nitrogens, or a nitrogen and a sulfur, or a nitrogen and an oxygen or where Het is a bicyclic heteroaromatic ring containing from 1 to 3 nitrogens or where $R_{15}$ is nitro, lower alkyl sulfonyl, cyano, lower alkyl, lower alkoxy, perfluorolower alkyl, lower alkylthio, lower alkanoyl, or aryl, especially where aryl is unsubstituted phenyl. In compound A $R_{16}$ may be hydrogen, halogen, nitro, cyano, lower alkyl, perfluoro lower alkyl; and $R_{30}$ is hydrogen or lower alkyl, or in compound A Het may be a 6 membered monocyclic heteroaromatic ring containing 1 or 2 nitrogens or a 10 membered bicyclic heteroaromatic ring containing one nitrogen, $R_{15}$ is lower alkyl, or perfluoroalkyl and $R_{16}$ is hydrogen, lower alkyl, or perfluoroalkyl, and $R_{30}$ is absent. In compound A , X-2 may be selected from the group of

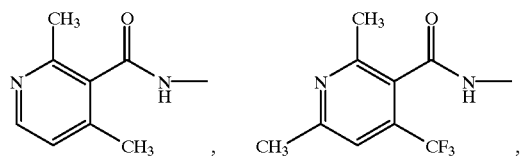

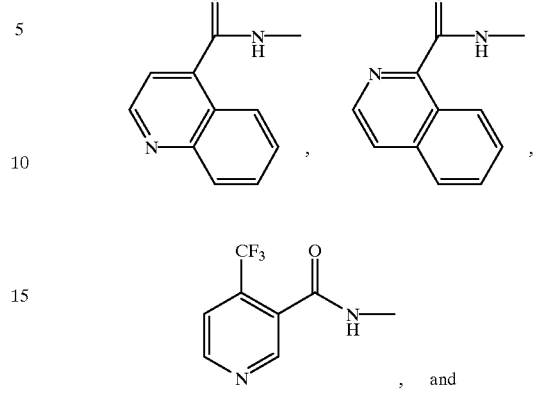

and

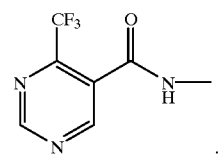

Compounds of formula 1 wherein X is a group of formula X-3

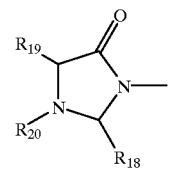

X-3 and Y, $R_{18}$, $R_{19}$, and $R_{20}$ are as in formula 1 (compound B). In compound B, it is preferred that $R_{18}$ is phenyl. In compound B it is also preferred that $R_{19}$ is lower alkyl which is unsubstituted or substituted by pyridyl or phenyl. In compound B it is also preferred that $R_{20}$ is substituted or unsubstituted lower alkanoyl. In compound B it is also preferred that $R_{18}$ is phenyl, $R_{19}$ is lower alkyl which is unsubstituted or substituted by pyridyl or phenyl and $R_{20}$ is lower alkanoyl. In compound B it is preferred that $R_{18}$ is phenyl which is unsubstituted or substituted by halogen or lower alkoxy; $R_{19}$ is phenyl lower alkyl which is unsubstituted or substituted by lower alkoxy, pyridyl lower alkyl, or lower alkyl; and $R_{20}$ is substituted or unsubstituted lower alkanoyl.

In this latter compound, it is preferred that X-3 is selected from the group of

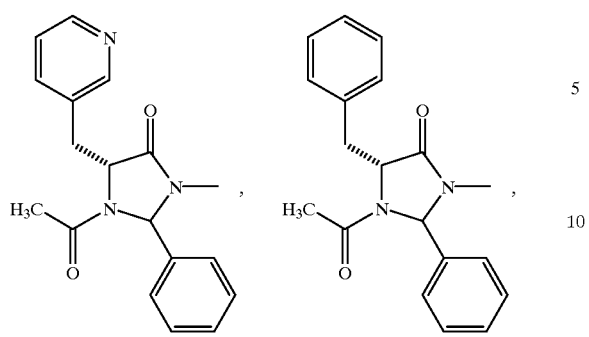
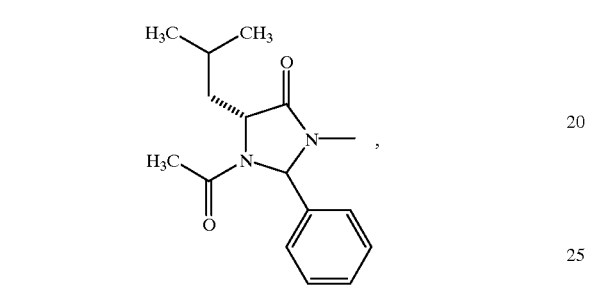
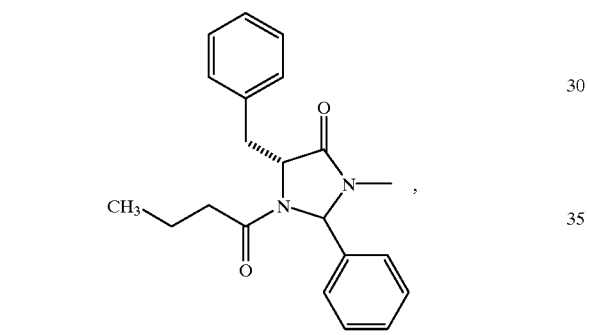
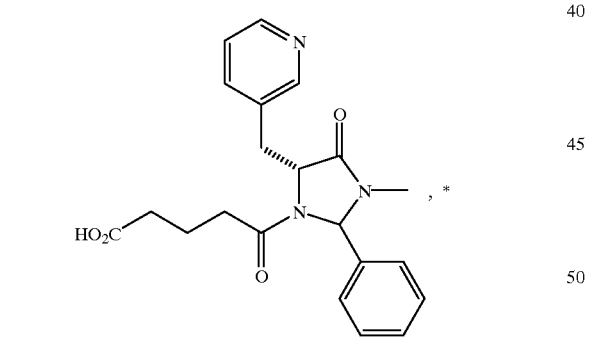
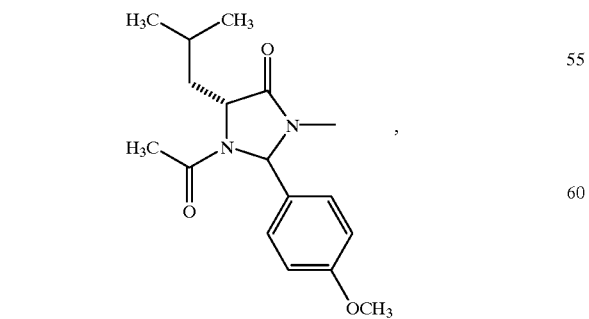
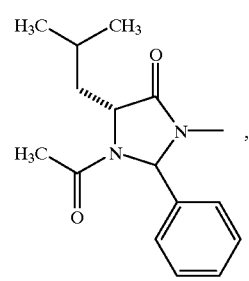
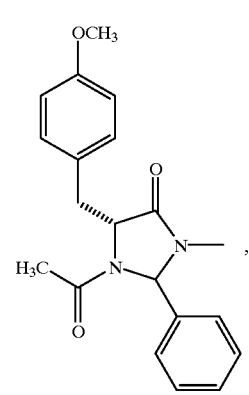
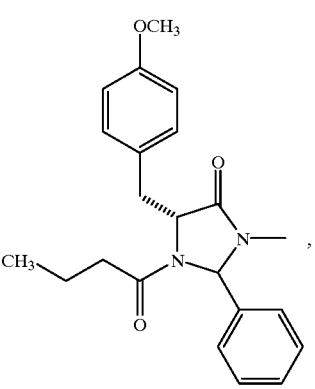
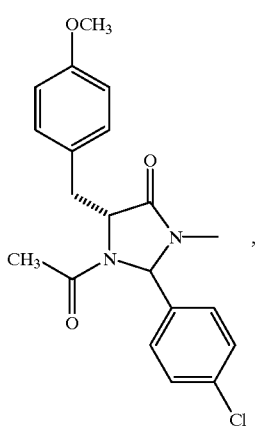

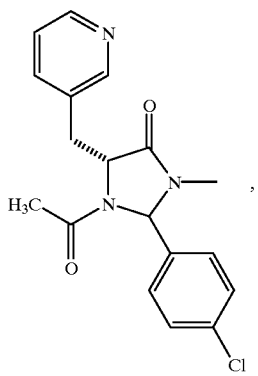

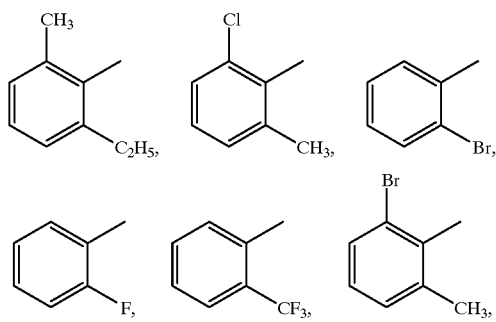

Compounds of formula 1 where Y is a group of formula

Y-1 and X, $R_{22}$, $R_{23}$, and $R_{24}$ are as in formula 1 (compound C). It is preferred for compound C that $R_{22}$ and $R_{23}$ are lower alkyl, trifluoromethyl, or halogen and $R_{24}$ is hydrogen, lower alkyl, lower alkoxy, or halogen, especially when Y-1 is selected from the group of

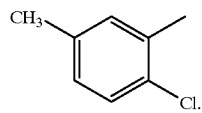

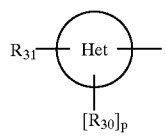

and

Compounds of formula 1 wherein Y is a group of the formula Y-2

Y-2 and p, X, Het, $R_{30}$ and $R_{31}$, are as in formula 1 (compound D). It is preferred for compound D that Het is a 6 membered heteroaromatic ring, especially where the heteroatom is N, and preferably where Y-2 is selected from the group of and

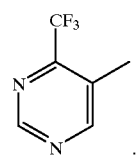
Compounds of formula 1 where Y is a group of formula Y-3
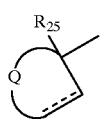 Y-3
and Y, $R_{25}$ and Q are as in formula 1, and the dotted bond can be optionally hydrogenated (compound E). It is preferred for compound E that Y-3 is selected from the group of
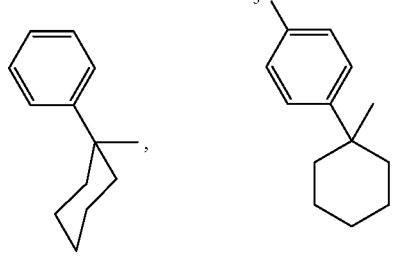
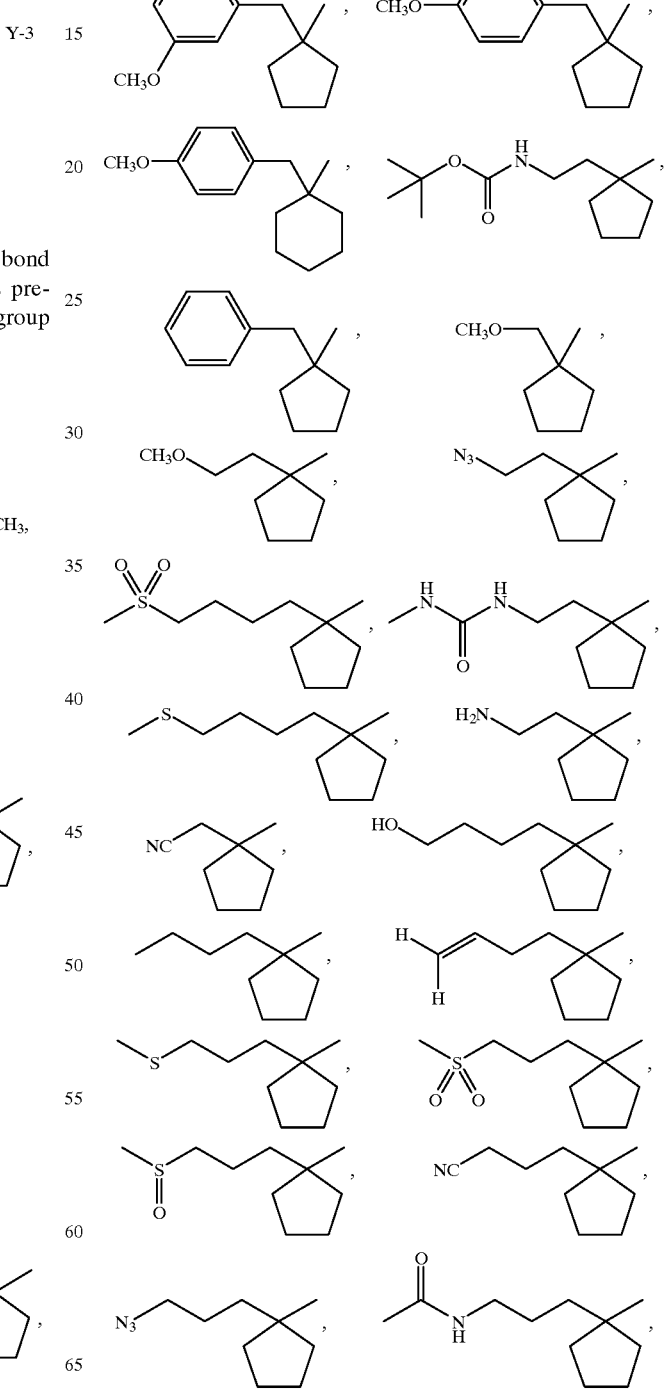

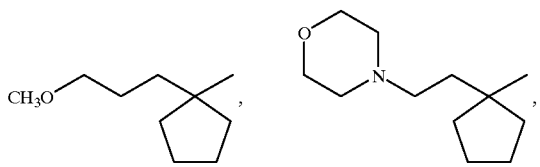

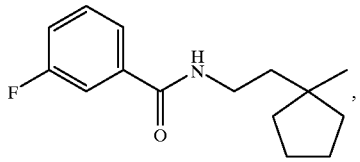

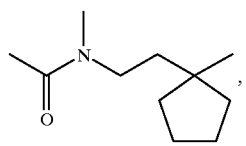

and

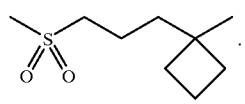

A compound of formula 1 wherein X is a group of the formula X-1I and Y is a group of the formula Y-1.

A compound of formula 1 wherein X is a group of the formula X-1 and Y is a group of the

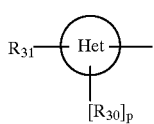

formula Y-2.

A compound of formula 1 wherein X is a group of the formula X-1 Y is a group of the formula Y-3 wherein $R_{15}$, $R_{16}$, $R_{25}$ and Q are as above; and the dotted bond can be optionally hydrogenated.

A compound of formula 1 wherein X is a group of the formula X-2 and Y is a group of the formula Y-1.

A compound of formula 1 wherein X is a group of the formula X-2 and Y is a group of the formula Y-2

A compound of formula 1 wherein X is a group of the formula X-2 and Y is a group of the formula Y-3

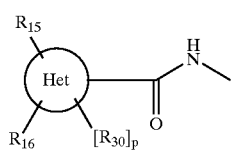

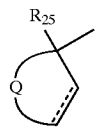

wherein $R_{15}$, $R_{16}$, $R_{25}$, $R_{30}$, Q and p are as above and the dotted bond can be optionally hydrogenated.

A compound of formula 1 where X is a group of the formula X-3 and Y is a group of the formula Y-1.

A compound of formula 1 wherein X is a group of the formula X-3 and Y is a group of the formula Y-2.

A compound of formula 1 wherein X is a group of the formula X-3 and Y is a group of the formula Y-3 where $R_{18}$, $R_{19}$, $R_{20}$, $R_{25}$, and Q are as above and the dotted bond can be optionally hydrogenated.

A compound of claim 1 wherein X is a group of the formula X-1

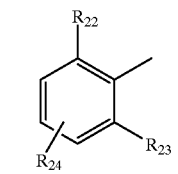

wherein $R_{16}$ is in the ortho position and is hydrogen, lower alkyl, nitro, cyano, halogen, lower alkylthio, perfluoroloweralkyl and $R_{15}$ is lower alkyl, nitro, cyano, halogen, lower alkylsulfonyl, perfluoroloweralkyl, and Y is a group of the formula Y-1

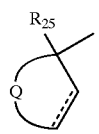

where $R_{22}$ is hydrogen, halogen, trifluoroalkyl, or lower alkyl and $R_{23}$ is halogen, trifluoroalkyl, or lower alkyl, and R24 is hydrogen or Y is a group of the formula Y-3

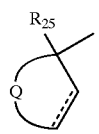

wherein Q is as above and the dotted bond can be optionally hydrogenated; $R_{25}$ is $R_{26}$—$(CH_2)e$—; e is 2–4 and $R_{26}$ is azido, cyano, hydroxy, lower alkoxy, lower alkoxycarbonyl, lower alkanoyl, lower alkyl sulfonyl, lower alkyl sulfinyl, perfluoro lower alkanoyl, nitro, or lower alkylthio or $R_{25}$ is $NHR_{29}$ where $R_{29}$ is lower alkanoyl or lower alkylamino carbonyl (compound E).

In compound E it is preferred that X is a group of the formula X-1

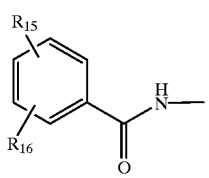

wherein $R_{16}$ is in the ortho position and is hydrogen, lower alkyl, nitro, cyano, halogen, lower alkylthio, perfluoroloweralkyl and $R_{15}$ is lower alkyl, nitro, cyano, halogen, lower alkylsulfonyl, perfluoroloweralkyl; and Y is a group of the formula Y-1

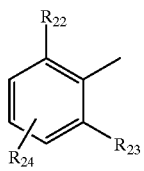

where $R_{22}$ is hydrogen, halogen, or lower alkyl and $R_{23}$ is halogen or lower alkyl, and R24 is hydrogen, especially where $R_{16}$ is hydrogen or halogen and $R_{15}$ is halogen; R22 is hydrogen, halogen, ethyl, or methyl and $R_{23}$ is halogen, ethyl, or methyl, and additionally where $R_{16}$ is in the ortho position and $R_{15}$ and R16 are both chlorine, and $R_{22}$ is methyl and $R_{23}$ is chlorine or ethyl. An example of such a compound is 4-[[(2,6-dichlorophenyl)carbonyl]amino]-N-[(2-chloro-6-methylphenyl)thioxomethyl]-L-phenylalanine.

In compound E it is also preferred that X is a group of the formula X-1

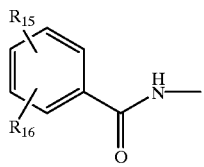

wherein $R_{16}$ is in the ortho position and is hydrogen, lower alkyl, nitro, cyano, halogen, lower alkylthio, perfluoroloweralkyl and $R_{15}$ is lower alkyl, nitro, cyano, halogen, lower alkylsulfonyl, perfluoroloweralkyl; and Y is a group of the formula Y-3

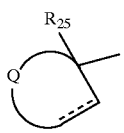

which is a four to six membered cycloalkyl ring, $R_{25}$ is $R_{26}$—(CH$_2$)e—; e is 2–4 and $R_{26}$ is azido, cyano, hydroxy, lower alkoxy, lower alkoxycarbonyl, lower alkanoyl, lower alkyl sulfonyl, lower alkyl sulfinyl, perfluoro lower alkanoyl, nitro, or lower alkylthio; and the dotted bond is hydrogenated. In such a compound it is preferred that $R_{16}$ is hydrogen or halogen and $R_{15}$ is halogen; and Y-3 is a four or five membered ring and $R_{26}$ is lower alkoxy, lower alkyl sulfonyl, lower alkyl sulfinyl, or lower alkylthio, especially where $R_{16}$ is in the ortho position and $R_{15}$ and $R_{16}$ are both chlorine, and $R_{26}$ is lower alkyl sulfonyl or lower alkylthio. An example of such a compound is 4-[[(2,6-dichlorophenyl)carbonyl]amino]-N-[[1-[(4-methylsulfonyl)butyl]cyclopentyl]thioxomethyl]-L-phenylalanine.

For another preferred compound E X is a group of the formula X-1

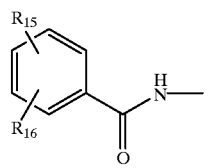

where $R_{16}$ is hydrogen or halogen and $R_{15}$ is halogen and Y is a group of the formula Y-1

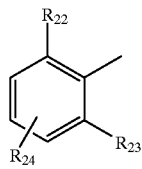

where $R_{22}$ is hydrogen, halogen, ethyl, or methyl and $R_{23}$ is halogen, ethyl, or methyl and $R_{24}$ is hydrogen or Y is a group of the formula Y-3

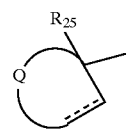

where Y-3 is a four or five membered ring, $R_{25}$ is as in claim 39 and $R_{26}$ is lower alkoxy, lower alkyl sulfonyl, lower alkyl sulfinyl, or lower alkylthio, and the dotted bond is optionally hydrogenated. For such a compound it is preferred that $R_{16}$ is in the ortho position and $R_{15}$ and $R_{16}$ are both chlorine, and when Y is Y-1 then $R_{22}$ is methyl and $R_{23}$ is chlorine or ethyl and when Y is Y-3, Y-3 is a four or five membered ring and $R_{26}$ is lower alkyl sulfonyl or lower alkylthio.

A compound of formula 1 wherein Y is as in formula 1 and X is X-1

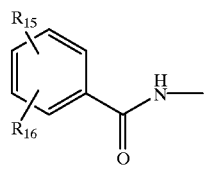

where $R_{15}$ is ortho and is halogen, lower alkyl, or perfluoroalkyl and $R_{16}$ is hydrogen, halogen, lower alkyl, or perfluoroalkyl (compound F).

For compound F it is preferred that $R_{,,}$ is chlorine and $R_{16}$ is hydrogen or chlorine.

A compound of formula 1 wherein Y is as in formula 1 and X is X-2 where Het is pyridine or pyrimidine and $R_{15}$ is lower alkyl or perfluoroalkyl $R_{16}$, and $R_{20}$ are hydrogen, lower alkyl, or perfluoroalkyl (compound G).

A compound of formula 1 wherein Y is as in formula 1 and X is X-3 where $R_{19}$ is pyridinyl lower alkyl or phenyl lower alkyl, $R_{20}$ is lower alkanoyl, and R18 is phenyl (compound H).

A compound of formula 1 where X is as in formula 1 and Y is Y-1 where $R_{22}$ is hydrogen or lower alkyl, $R_{23}$ is halogen, lower alkyl, or perfluoroalkyl, and R24 is hydrogen, especially where $R_{22}$ is hydrogen or methyl and $R_{23}$ is halogen, ethyl, or trifluoromethyl.

A compound of formula 1 wherein X is as in formula 1 and Y is Y-3 which is a four to six membered cycloalkyl ring, $R_{25}$ is $R_{26}$—($CH_2$)e—, e is 2–4, and $R_{26}$ is alkoxy, lower alkyl sulfonyl, loweralkylthio, or $NHR_{29}$ where $R_{29}$ is loweralkoxycarbonyl or loweralkylaminocarbonyl, and the dotted bond is hydrogenated. It is preferred that $R_{26}$ is methoxy, methyl sulfonyl, or methylthio.

A preferred compound F has Y is Y-1 where $R_{22}$ is hydrogen or lower alkyl, $R_{23}$ is halogen, lower alkyl, or perfluoroalkyl, and $R_{24}$ is hydrogen. It is preferred that $R_{15}$ is chlorine and $R_{16}$ is hydrogen or chlorine. Examples are
4-[[(2,6-dichlorophenyl)carbonyl]amino]-N-[(2-bromophenyl)thioxomethyl]-L-phenylalanine;
4-[[(2,6,-dichlorophenyl)carbonyl]amino-N-[(2-ethyl-6-methylphenyl)thioxomethyl]L-phenylalanine.
4-[[(2,6,-dichlorophenyl)carbonyl]amino]-N-[(2-fluorophenyl)thioxomethyl]-L-phenylalanine. 4-[[2,6,-dichlorophenyl)carbonyl]amino]-N-[[2-(trifluoromethyl)phenyl]thioxomethyl]-L-phenylalanine.

In a preferred compound G, Y is Y-1 where $R_{22}$ is hydrogen or lower alkyl, $R_{23}$ is halogen, lower alkyl, or perfluoroalkyl, and $R_{24}$ is hydrogen.

In a preferred compound H, Y is Y-1 where $R_{22}$ is hydrogen or lower alkyl, $R_{23}$ is halogen, lower alkyl, or perfluoroalkyl, and $R_{24}$ is hydrogen. An example of such a compound is 4-[(2S,4R)-3-acetyl-2-phenyl-4-[(3-pyridinyl)methyl]-5-oxo-iridazolidin-1-yl]-N-[(2-ethyl-6-methylphenyl) thioxomethyl]-L-phenylalanine.

In a preferred compound F, Y is Y-3 which is a four to six membered cycloalkyl ring, $R_{25}$

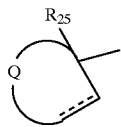

is $R_{26}$—($CH_2$)e—, e is 2–4, and $R_{26}$ is alkoxy, lower alkyl sulfonyl, loweralkylthio, or $NHR_{29}$ where $R_{29}$ is loweralkoxycarbonyl or loweralkylaminocarbonyl, and the dotted bond is hydrogenated. It
is preferred that $R_{15}$ is chlorine and $R_{16}$ is hydrogen or chlorine. Examples of such compounds are 4-[[2,6-dichlorophenyl)carbonyl]amino-N-[[1-[2-(acetylamino)ethyl]cyclopentyl]thioxomethyl]-L-phenylalanine.
[[1-[2-[[(methylamino)carbonyl]amino]ethyl]cyclopentyl]thioxomethyl]-4-[[(2,6-dichlorophenyl)carbonyl]amino]L-phenylalanine.
4-[[(2,6,-dichlorophenyl)carbonyl]amino]-N-[[1-(2-methoxyethyl)cyclopentyl]thioxomethyl]-L-phenylalanine.
4-[[(2,6,-dichlorophenyl)carbonyl]amino]-N-[[1-[(4-methylsulfonyl)butyl]cyclobutyl]thioxomethyl]-L-phenylalanine.
4-[[(2,6,-dichlorophenyl)carbonyl]amino]-N-[[1-(3-methylthio)propyl]cyclobutyl]thioxomethyl]-L-phenylalanine.
4-[[(2,6,-dichlorophenyl)carbonyl]amino]-N-[[1-(3-methylsulfonyl)propyl]cyclobutyl]thioxomethyl]-L-phenylalanine.

It is preferred that R26 is methoxy, methyl sulfonyl, or methyl thio, especially where $R_{15}$ is chlorine and $R_{16}$ is hydrogen or chlorine.

A preferred compound G wherein Y is Y-3 which is a four to six membered cycloalkyl ring, $R_{25}$ is $R_{26}$—($CH_2$)e—, e is 2–4, and $R_{26}$ is alkoxy, lower alkyl sulfonyl, loweralkylthio, or $NHR_{29}$ where $R_{29}$ is loweralkoxycarbonyl or loweralkylaminocarbonyl, and the dotted bond is hydrogenated. Preferably $R_{26}$ is methoxy, methyl sulfonyl, or methyl thio. Examples are
4-[(2,6-dimethyl-3-pyridinylcarbonyl)amino]-N-[[1-[(4-methylsulfonyl)butyl]cyclopentyl]thioxomethyl]-L-phenylalanine.
4-[[[4-(trifluoromethyl)-5-pyrimidinyl]carbonyl]amino]-N-[[1-(4-methylsulfonyl)butyl]cyclobutyl]thioxomethyl]-L-phenylalanine.
4-[[(2,4-dimethyl-6-trifluoromethyl-3-pyridinyl)carbonyl]amino]-N-[[1-[(4-methylsulfonyl)butyl]cyclobutyl]thioxomethyl]-L-phenylalanine.

In a preferred compound H, Y is Y-3 which is a four to six membered cycloalkyl ring, $R_{25}$

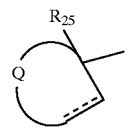

is $R_{26}$—($CH_2$)e—, e is 2–4, and $R_{26}$ is alkoxy, lower alkyl sulfonyl, loweralkylthio, or $NHR_{29}$ where $R_{29}$ is loweralkoxycarbonyl or loweralkylaminocarbonyl, and the dotted bond is optionally hydrogenated, especially where $R_{26}$ is methoxy, methyl sulfonyl, or methyl thio. Examples are
4-[(2S,4R)-3-acetyl-2-phenyl-4-[(3-phenyl)methyl]-5-oxo-imidazolidin-1-yl]-N-[[(4-methylsulfonyl)butyl]cyclopentyl]thioxomethyl]-L-phenylalanine
4-[(2R,4R)-3-acetyl-2-phenyl-4-[(3-phenyl)methyl]-5-oxo-imidazolidin-1-yl]-N-[[(4-methylsulfonyl)butyl]cyclopentyl]thioxomethyl]-L-phenylalanine.

As used in this specification, the terms are defined as follows:

The term "halogen" means bromine, chlorine, fluorine, or iodine, and the term "halo" means a halogen substituent. The term "perfluoro" means complete substitution of all hydrogen atoms with fluoro substituted, as in perfluoro lower alkyl, perfluoroloweralkanoyl and perfluoroalkanoylamino. An example is trifluoromethyl.

The term "lower alkyl", alone or in combination (for example as part of lower alkanoyl, below), means a straight-chain or branched-chain alkyl group containing a maximum of six carbon atoms, such as methyl, ethyl, n-propyl, isopropyl, n-butyl, sec.butyl, isobutyl, tert.butyl, n-pentyl, n-hexyl and the like. Lower alkyl groups may be unsubstituted or substituted by one or more groups selected independently from cycloalkyl, nitro, aryloxy, aryl (preferably phenyl or pyridyl), hydroxy (lower alkylhydroxy or hydroxylower alkyl), halogen, cyano, lower alkoxy (alkoxy lower alkyl or lower alkyl alkoxy), lower alkanoyl, lower alkylthio (lower alkylthio lower alkyl) sulfinyl (lower alkyl sulfinyl), sulfinyl lower alkyl (lower alkyl sulfinyl lower alkyl) sulfonyl (lower alkyl sulfonyl), sulfonyl lower alkyl (lower alkyl sulfonyl lower alkyl) perfluoro perfluoro lower alkyl) and substituted amino such as aminosulfonyl (lower alkyl aminosulfonyl) or aminocarbonyl (lower alkyl aminocarbonyl). Examples of substituted lower alkyl groups include 2-hydroxylethyl, 3-oxobutyl, cyanomethyl, and 2-nitropropyl. The term "lower alkylthio" means a lower alkyl group bonded through a divalent sulfur atom, for example, a methyl mercapto or a isopropyl mercapto group.

The term "cycloalkyl" means an unsubstituted or substituted 3-to 7-membered carbacyclic ring. Substituents useful in accordance with the present invention are hydroxy, halogen, cyano, lower alkoxy, lower alkanoyl, lower alkyl, aroyl, lower alkylthio, lower alkyl sulfinyl, lower alkyl sulfonyl, aryl, heteroaryl and substituted amino.

The term "lower alkoxy" means a lower alkyl group as defined above, bonded through an oxygen atom. Examples are methoxy, ethoxy, n-propoxy, isopropoxy, n-butoxy, tert-butoxy and the like.

The term "lower alkenyl" means a nonaromatic partially unsaturated hydrocarbon chain containing at least one double bond, which is preferably 1–10 and more preferably 1–6 carbons in length. The group may be unsubstituted, or substituted with conventional substituents, preferably fluoro. Examples are vinyl, allyl, dimethylallyl, butenyl, isobutenyl, pentenyl.

The term "aryl" means a mono- or bicylic aromatic group, such as phenyl or naphthyl, which is unsubstituted or substituted by conventional substituent groups. Preferred substituents are lower alkyl, lower alkoxy, hydroxy lower alkyl, hydroxy, hydroxyalkoxy, halogen, lower alkylthio, lower alkylsulfinyl, lower alkylsulfonyl, cyano, nitro, perfluoroalkyl, alkanoyl, aroyl, aryl alkynyl, lower alkynyl, aminoalkylcarbonyl (arylaminocarbonyl) and lower alkanoylamino. The especially preferred substituents are lower alkyl, hydroxy, and perfluoro lower alkyl. Examples of aryl groups that may be used in accordance with this invention are phenyl, p-tolyl, p-methoxyphenyl, p-chlorophenyl, m-hydroxy phenyl, m-methylthiophenyl, 2-methyl-5-nitrophenyl, 2,6-dichlorophenyl, 1-naphthyl and the like.

The term "arylalkyl" means a lower alkyl group as hereinbefore defined in which one or more hydrogen atoms is/are replaced by an aryl group as herein defined. Any conventional aralkyl may be used in accordance with this invention, such as benzyl and the like. Similarly, the term "heteroarylalkyl" is the same as an arylalkyl group except that there is a heteroaryl group as defined below in place of an aryl group. Either of these groups may be unsubstituted, or may be substituted on the ring portion with conventional substituents such as The term "heteroaryl" means an unsubstituted or substituted 5- or 6-membered monocyclic hetereoaromatic ring or a 9-or 10-membered bicyclic heteroaromatic ring containing 1, 2, 3 or 4 heteroatoms which are independently N, S or O. Examples of hetereoaryl rings are pyridine, benzimidazole, indole, imidazole, thiophene, isoquinoline, quinzoline and the like. Substituents as defined above for "aryl" apply equally here in the definition of heteroaryl. The term "heteroaromatic ring" may be used interchangeably with the term heteroaryl.

The term "lower alkoxycarbonyl" means a lower alkoxy group bonded via a carbonyl group. Examples of alkoxycarbonyl groups are ethoxycarbonyl and the like.

The term "lower alkylcarbonyloxy" means lower alkylcarbonyloxy groups bonded via an oxygen atom, for example an acetoxy group.

The term "lower alkanoyl" means lower alkyl groups bonded via a carbonyl group and embraces in the sense of the foregoing definition groups such as acetyl, propionyl and the like. Lower alkanoyl groups may be unsubstituted, or substituted with conventional substituents such as alkoxy, lower alkyl, hydroxy, aryl, and hetereoaryl.

The term "lower alkylcarbonylamino" means lower alkylcarbonyl groups bonded via a nitrogen atom, such as acetylamino.

The term "aroyl" means an mono- or bicyclic aryl or heteroaryl group bonded via a carbonyl group. Examples of aroyl groups are benzoyl, 3-cyanobenzoyl, 2-naphthyl and the like. Aroyl groups may be unsubstituted, or substituted with conventional substituents such as The term "aryloxy" means an aryl group, as hereinbefore defined, which is bonded via an oxygen atom. The preferred aryloxy group is phenoxy.

The term "electron-deficient substituent" means a substituent on an aromatic or heteroaromatic ring which has a positive Hammett sigma valus as defined for example in Jerry March, Advanced Organic Chemistry, 2nd Edition, McGraw Hill, 1977, page 246–253. Typical electron withdrawing groups are cyano, nitro, chloro, alkoxycarbonyl lower alkyl sulfonyl, and aminocarbonyl.

In the compound of formula 1, Y is preferably the group Y-1 whereby the invention comprises a compound of the formula:

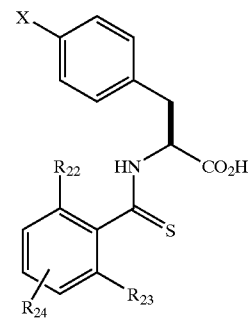

wherein X, $R_{22}$, $R_{23}$ and $R_{24}$ are as above.

In the group Y-1, $R_{22}$ and $R_{23}$ are preferably lower alkyl or halogen and R24 is preferably hydrogen.

Among the groups Y-1, when $R_{23}$ is lower-alkyl or halogen, Y-1 is preferably:

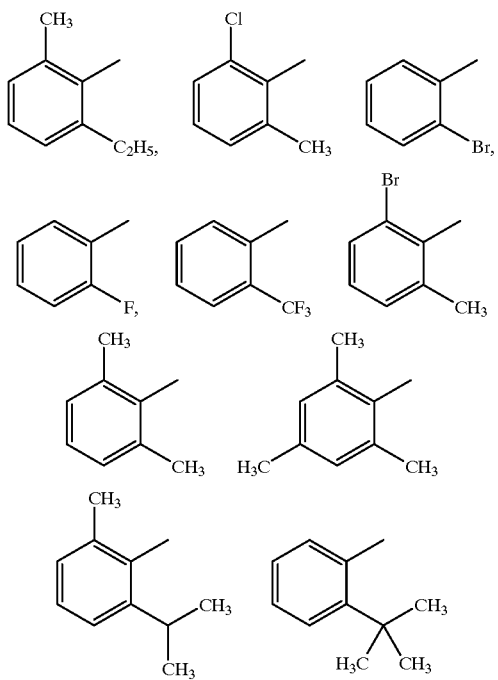

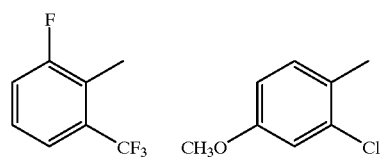
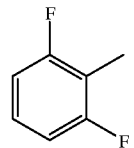
When Y is a group Y-2, Y is preferably:
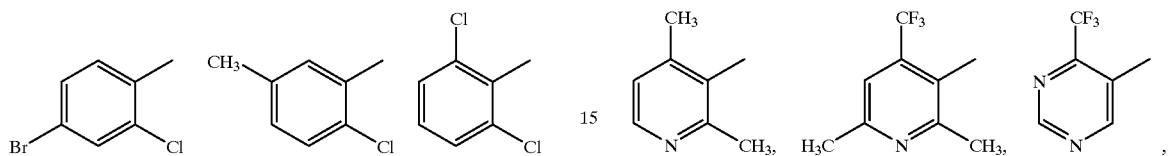
When Y is a group Y-3, Y is preferably:
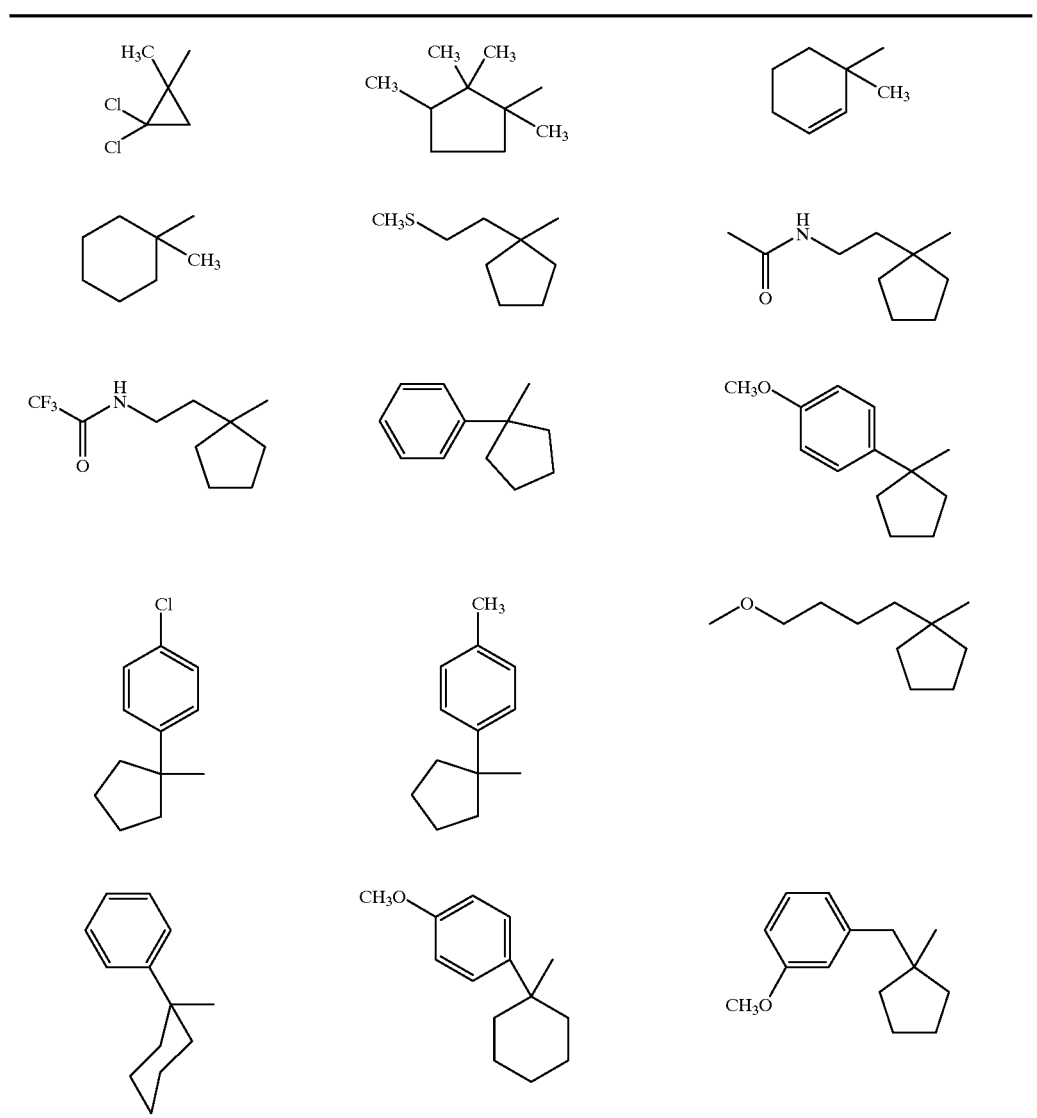

-continued
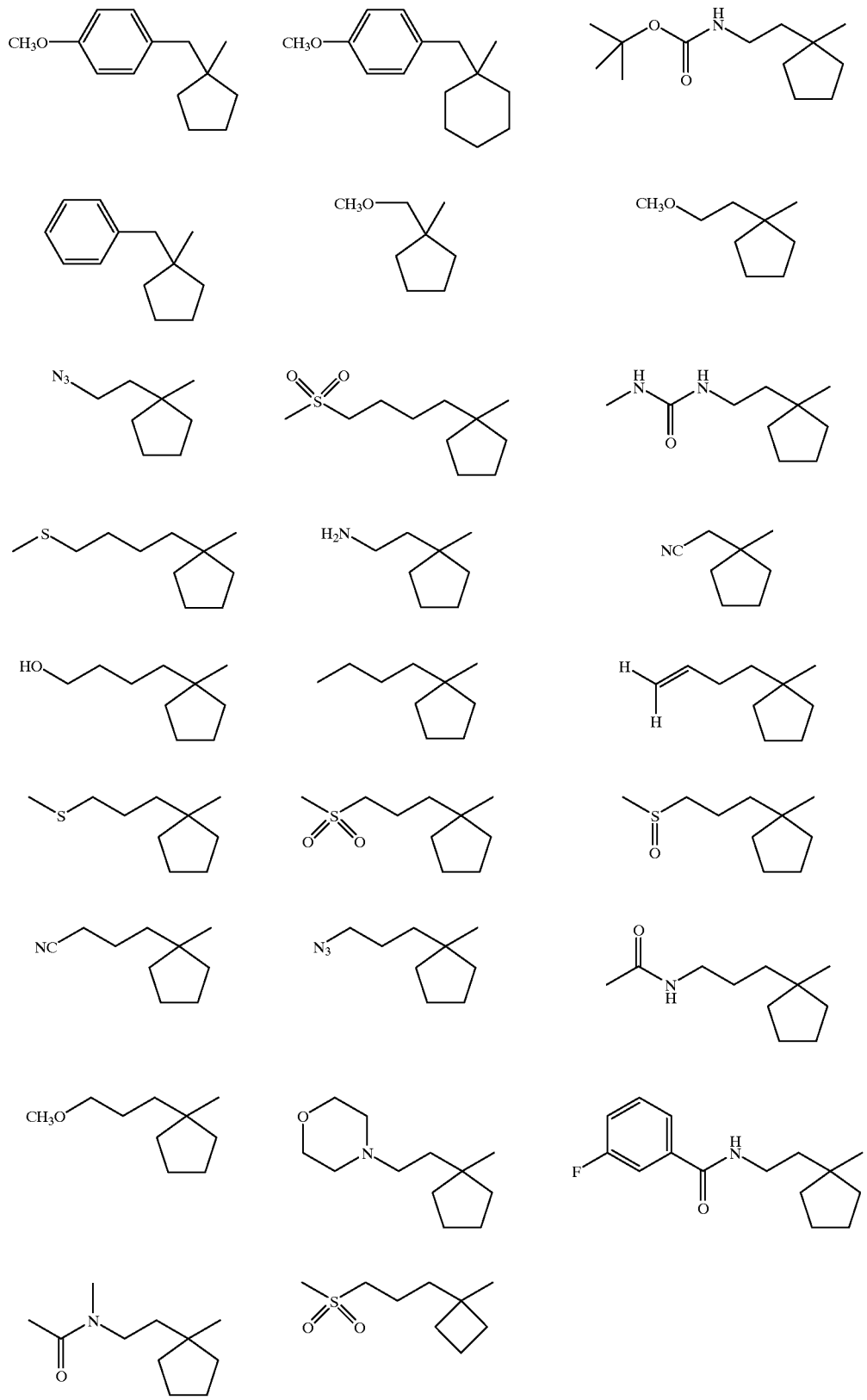

The especially preferred groups X-1 are of the formula:
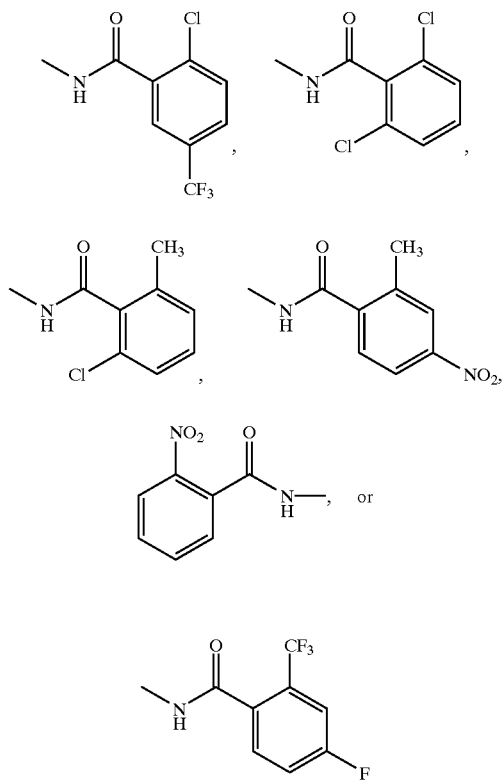
The especially preferred groups X-2 are of the formula:
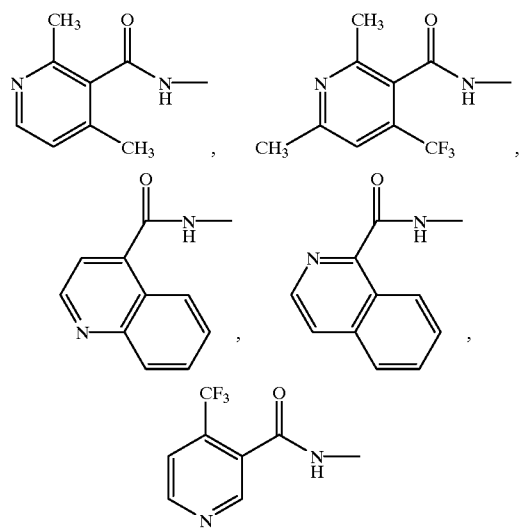
and
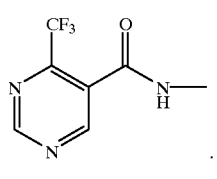
They especially preferred groups X-3 are of the formula:
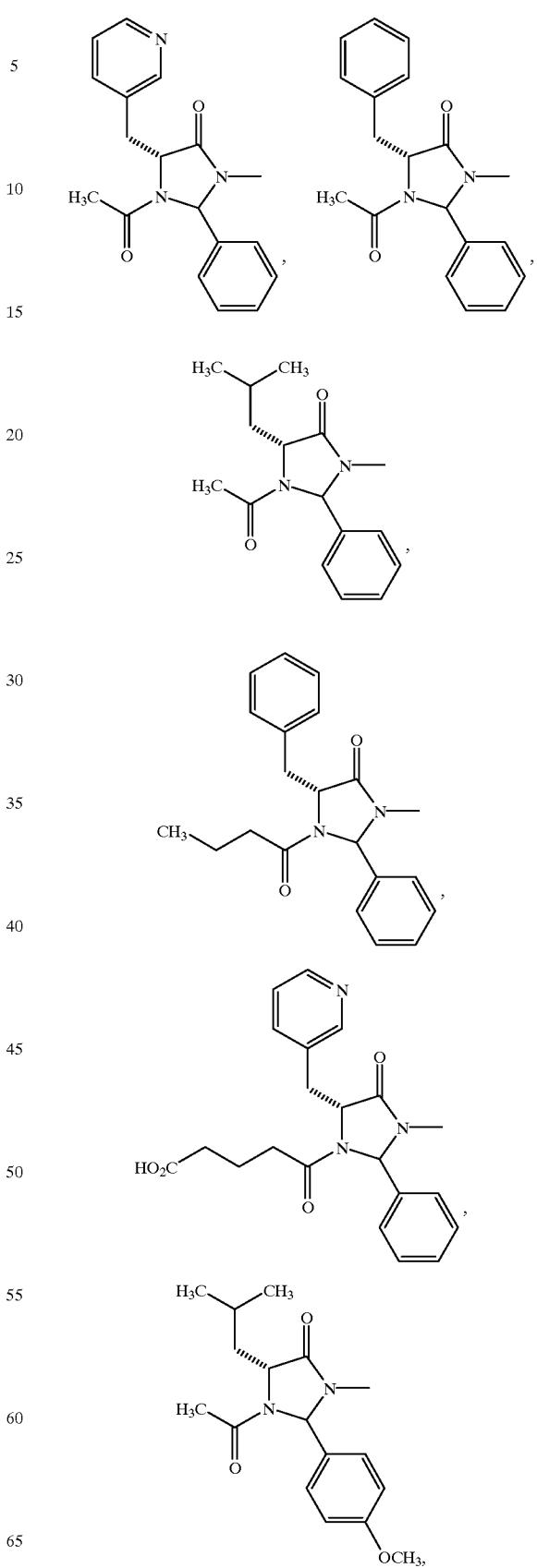

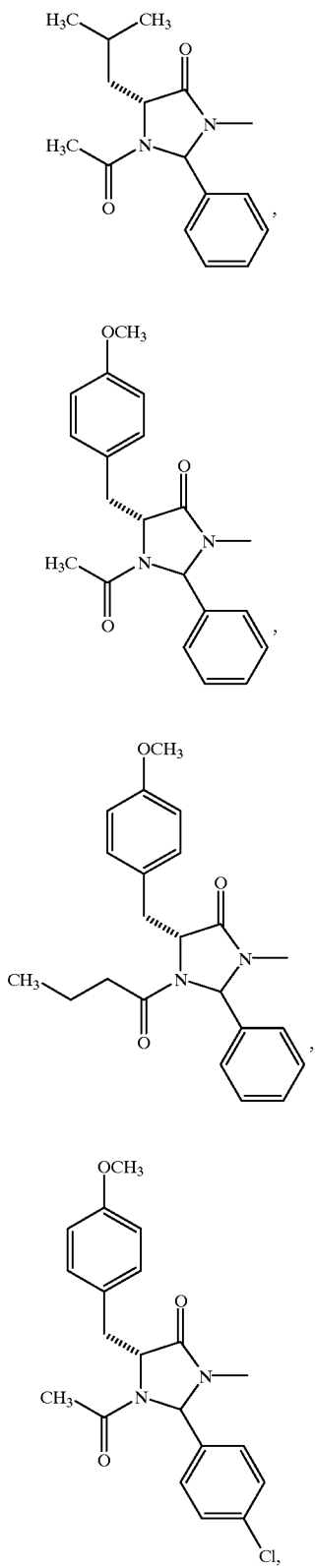

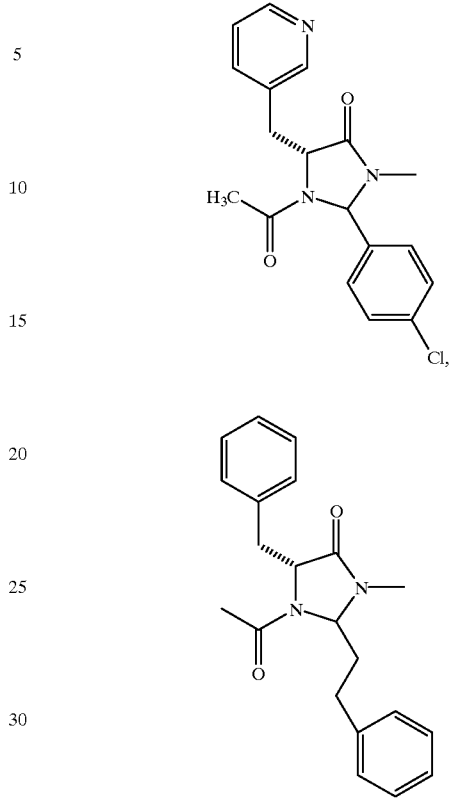

The compounds of the invention can exist as stereoisomers and diastereomers, all of which are encompassed within the scope of the present invention.

The compounds of the invention inhibit the binding of VCAM-1 and fibronectin to VLA-4 on circulating lymphocytes, eosinophils, basophils, and monocytes ("VLA-4-expressing cells"). The binding of VCAM-1 and fibronectin to VLA-4 on such cells is known to be implicated in certain disease states, such as rheumatoid arthritis, multiple sclerosis, inflammatory bowel disease, and particularly in the binding of eosinophils to pulmonary endothelium which contributes to the cause of the pulmonary inflammation which occurs in asthma. Thus, the compounds of the present invention would be useful for the treatment of asthma.

On the basis of their capability of inhibiting binding of VCAM-1 and fibronectin to VLA-4 on circulating lymphocytes, eosinophils, basophils, and monocytes, the compounds of the invention can be used as medicament for the treatment of disorders which are known to be associated with such binding. Examples of such disorders are rheumatoid arthritis, multiple sclerosis, asthma, and inflammatory bowel disease. The compounds of the invention are preferably used in the treatment of diseases which involve pulmonary inflammation, such as asthma. The pulmonary inflammation, which occurs in asthma, is related to eosinophil infiltration into the lungs wherein the eosinophils bind to endothelium which has been activated by some asthma-triggering event or substance.

Furthermore, compounds of the invention also inhibit the binding of VCAM-1 and MadCAM to the cellular receptor alpha4-beta7, also known as LPAM, which is expressed on lymphocytes, eosinophils and T-cells. While the precise role of alpha4-beta7 interaction with various ligands in inflammatory conditions such as asthma is not completely understood, compounds of the invention which inhibit both alpha4-beta1 and alpha4-beta7 receptor binding are particularly effective in animal models of asthma. Furthermore work with monoclonal antibodies to alpha4-beta7 indicate that compounds which inhibit alpha4-beta7 binding to MadCAM or VCAM are useful for the treatment of inflammatory bowel disease. They would also be useful in the treatment of other diseases in which such binding is implicated as a cause of disease damage or symptoms.

The compounds of the invention can be administered orally, rectally, or parentally, e.g., intravenously, intramuscularly, subcutaneously, intrathecally or transdermally; or sublingually, or as opthalmalogical preparations, or as an aerosol in the case of pulmonary inflammation. Capsules, tablets, suspensions or solutions for oral administration, suppositories, injection solutions, eye drops, salves or spray solutions are examples of administration forms.

Intravenous, intramuscular, oral or inhalation administration is a preferred form of use. The dosages in which the compounds of the invention are administered in effective amounts depending on the nature of the specific active ingredient, the age and the requirements of the patient and the mode of administration. Dosages may be determined by any conventional means, e.g., by dose-limiting clinical trials. Thus, the invention further comprises a method of treating a host suffering from a disease in which VCAM-1 of fibronectin binding to VLA-4-expressing cells is a causative factor in the disease symptoms or damage by administering an amount of a compound of the invention sufficient to inhibit VCAM-1 or fibronectin binding to VLA-4-expressing cells so that said symptoms or said damage is reduced. In general, dosages of about 0.1–100 mg/kg body weight per day are preferred, with dosages of 1–25 mg/kg per day being particularly preferred, and dosages of 1–10 mg/kg body weight per day being especially preferred.

The invention further comprises pharmaceutical compositions which contain a pharmaceutically effective amount of a compound of the invention and a pharmaceutically acceptable carrier. Such compositions may be formulated by any conventional means. Tablets or granulates can contain a series of binders, fillers, carriers or diluents. Liquid compositions can be, for example, in the form of a sterile water-miscible solution. Capsules can contain a filler or thickener in addition to the active ingredient. Furthermore, flavor-improving additives as well as substances usually used as preserving, stabilizing, moisture-retaining and emulsifying agents as well as salts for varying the osmotic pressure, buffers and other additives can also be present.

The previously mentioned carrier materials and diluents can comprise any conventional pharmaceutically acceptable organic or inorganic substances, e.g., water, gelatin, lactose, starch, magnesium stearate, talc, gum arabic, polyalkylene glycols and the like.

Oral unit dosage forms, such as tablets and capsules, preferably contain from 25 mg to 1000 mg of a compound of the invention.

The compounds of the present invention may be prepared by any conventional means. In reaction Scheme 1, a 4-nitro-L-phenylalanine derivative of formula 1 in which $R_1$ is lower alkyl, which is a known compound or readily prepared by conventional means, is acylated with a benzoic acid derivative of formula 2 in which $R_2$ hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl, $R_3$ is hydrogen, halogen or lower alkyl and R4 is hydrogen, lower alkyl, lower alkoxy, aryl, nitro, cyano, lower alkyl sulfonyl, or halogen, using conventional means for amide bond formation. For example, a compound of formula 2 may be converted to the corresponding acid chloride and condensed with a compound of formula 1 in the presence of a proton acceptor such as a tertiary alkylamine. Alternatively compound 1 can be coupled with a carboxylic acid of formula 2 using standard peptide coupling conditions, for example HBTU in the presence of DIPEA in a polar, aprotic solvent such as DMF at a temperature between 0° C. and room temperature to give a compound of formula 3.

Conversion of the compound of formula 3 to the corresponding thioamide of formula 4 can be carried out by treatment with Lawesson's reagent which is [2,4-bis(4-methoxyphenyl)-1,3-dithia-2,4-diphosphetane-2,4-disulfide]. The procedure is standard and has been described in detail. See for example, Scheibey, S., Pedersen, B. S., Lawesson, S.-O. Bull Soc. Chim. Belg. 1978 87, 229 and Cava, M. P., Levinson, M. I., Tetrahedron 1985, 41, 5061. The nitro group of the compound of formula 4 may be reduced to the corresponding amine by any of the conventional means which are compatible with thioamides. One convenient procedure employs zinc dust as the reducing agent in the presence of methanol, ammonium chloride and water at a temperature of from 35 to 60° C. to give a compound of formula 5. Acylation of this compound with an aryl- or heteroaryl carboxylic acid of formula 6 using standard peptide coupling conditions, for example HBTU in the presence of DIPEA in a polar, aprotic solvent such as DMF at a temperature between 0° C. and room temperature gives a compound of formula 7. In certain cases, for example with hindered carboxylic acids 6, it may be advantageous to form the corresponding acid halide and react it with the amine of formula 5, typically in the presence of a slight excess of a base such as a tertiary amine or 4-(dimethylamino)pyridine. The carboxylic acid of formula 6 may be substituted by halogen, nitro, lower alkyl sulfonyl, cyano, lower alkyl, lower alkoxy, lower alkoxycarbonyl, carboxy, lower alkyl aminosulfonyl, perfluorolower alkyl, lower alkylthio, hydroxy lower alkyl, alkoxy lower alkyl, alkylthio lower alkyl, alkylsulfinyl lower alkyl, alkylsufonyl lower alkyl, lower alkylsulfinyl, lower alkanoyl, aroyl, aryl, aryloxy. Where appropriate, it may also incorporate suitably protected reactive functionalities which must be removed to permit final conversion into compounds of the invention. The choice and use of such groups will be apparent to those skilled in the art. Guidance for the selection and use of protecting groups is provided in standard reference works, for example: "T. W. Green and P. G. M. Wuts, Protective Groups in Organic Synthesis, $2^{nd}$ edition, Wiley Interscience, New York, 1991. The ester moiety of compound 7 can generally be cleaved to the corresponding carboxylic acid by treatment with an alkali metal hdyroxide, for example, lithium hydroxide in aqueous methanol at a temperature of from room temperature to 50° C. Depending on the nature of $R_1$, alternative procedures may be preferred. The choice of conditions for ester cleavage in the presence of functionalities such as thioamides is well known to those skilled in the art.

Scheme 1

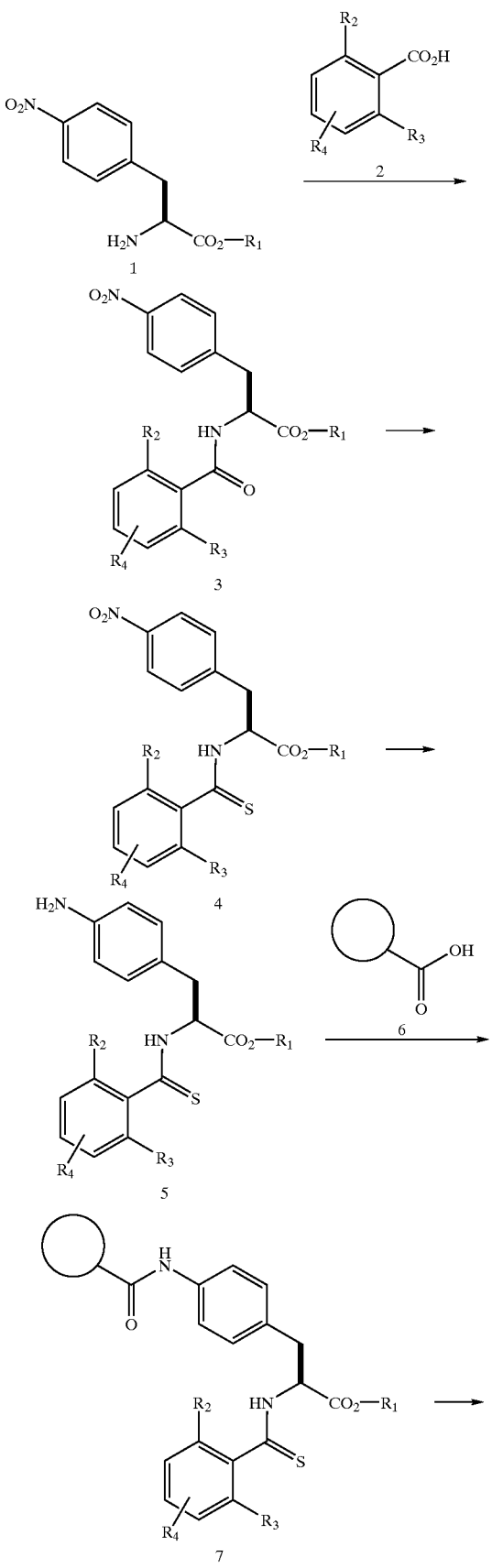

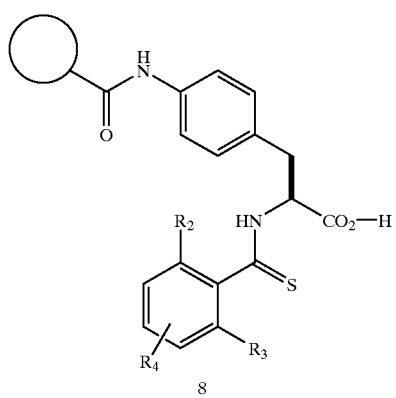

Ortho-substituted benzoic acid derivatives which are not commercially available can be prepared by conventional means. For example ortho-substituted aryl iodides or triflates may be carbonylated in the presence of carbon monoxide and a suitable palladium catalyst. The preparation of such iodide or triflate intermediates is dependent on the particular substitution pattern desired and they may be obtained by direct iodination or diazotization of an aniline followed by treatment with a source of iodide for example, potassium iodide. Triflates may be derived from the corresponding phenols by conventional means such as treatment with trifluoromethane sulfonic anhydride in the presence of a base such as triethylamine or diisopropylethylamine in an inert solvent. Other means of obtaining ortho-substituted benzoic acids involves treatment of an 2-methoxyphenyloxazoline derivative such as 9 with an alkyl Grignard reagent followed by hydrolysis of the oxazoline ring following the general procedure described by Meyers, A. I., Gabel, R., Mihelick, E. D, *J. Org. Chem.* 1978, 43, 1372–1379., to give an acid of formula 10. 2-or 2,6-Disubstituted benzonitriles also serve as convenient precursors to the corresponsing benzoic acids. In the case of highly hindered nitrites, for example 2-chloro-6-methylbenzonitrile, conventional hydrolysis under acidic or basic conditions is difficult and better results are obtained by DIBAL reduction to the corresponding benzaldehyde followed by oxidation using a sodium chlorite/hydroperoxide oxidizing reagent.

Scheme 2

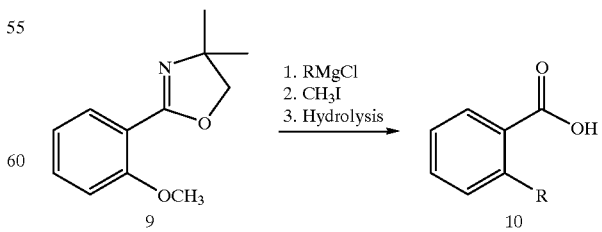

Employing essentially the same procedures described in Scheme 1, utilizing a heteroaromatic carboxylic acid in place of 2, one can prepare compounds of formula 11.

11

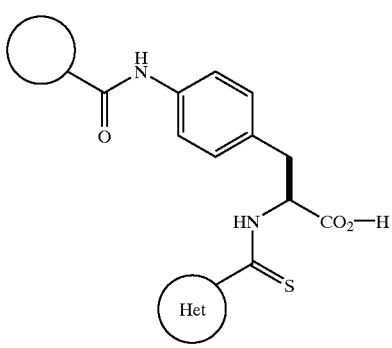

For the synthesis of analogues a branched chain or cycloalkyl moiety, a similar procedure to that described in scheme 1 can be employed starting with the appropriate branched chain or cycloalkyl carboxylic acid of formula 12. In this case, $R_6$ represents is lower alkyl, unsubstituted or fluorine substituted lower alkenyl, or a substituted lower alkyl group wherein the substituents may be chosen from aryl, heteroaryl, azido, cyano, hydroxy, lower alkoxy, lower alkoxycarbonyl, lower alkylthio, lower alkyl sulfonyl, perfluoro lower alkanoyl, nitro, or a protected amino group. The amine protecting group must be chosen to be compatible with the reagents needed to convert carboxamides to thioamides. Carbamates, for example, the tert-butoxycarbonyl moiety are suitable. As appropriate, these protecting groups may be removed by conventional means later in the synthesis and the resulting free amine can be further functionalized utilizing standard methods. For example, the amine can be acylated by treatment with the appropriate anhydride, isocyanate or acid halide.

12

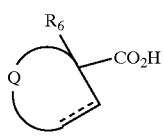

The synthesis of imidazolidinones of formula 21 is described in reaction scheme 3. An aminophenylalanine derivative of structure 13 in which $R_6$ is aryl, heteroaryl, branched chain alkyl or derived from a compound of formula 12, and $R_7$ is lower alkyl, is coupled with a N-protected alpha-amino acid of formula 14, in which $R_8$ can be a natural or unnatural, D- or L-α-amino acid side chain and $R_9$ is a nitrogen protecting group of the type conventionally used in peptide chemistry, for example, a Fmoc group, using standard peptide coupling conditions, for example HBTU in the presence of DIPEA in a polar, aprotic solvent such as DMF at a temperature between 0° C. and room temperature to give a compound of formula 15. Depending on the nature of protecting group $R_9$, an appropriate deprotection method is employed to give compound of formula 16. In the case of the protecting group $R_9$ is Fmoc group, it may be removed from 15 using standard base treatment well known to those practicing peptide chemistry, for example with piperidine in DMF, to afford an amine of formula 16. The compound 16 can then react with an aldehyde 17, in which $R_{10}$ is lower alkyl, aryl, or aryl lower alkyl, in the presence of a water scavenger such as 4 Å molecular sieves in an appropriate solvent such as dichloromethane or THF at 25–60° C. to give an imine of formula 18. The imine 18 may then be treated with an acylating agent such as the acyl chloride of formula 19 in which $R_{11}$ can be an alkyl or aryl group in the presence of a base such DIPEA or DBU in an appropriate solvent such as dichloromethane or THF at 25–60° C. to give an acyl imidazolidinone of formula 20. Alternatively, other reactive acylating groups such as acid anhydrides or mixed anhydrides may be employed in this reaction. Compound 20 may be converted to a compound of the invention by an appropriate hydrolysis procedure, for example by hydrolysis by treatment with an alkali metal hydroxide, for example sodium hydroxide in aqueous alcohol to give, after acidification, a carboxylic acid of formula 21.

Scheme 3

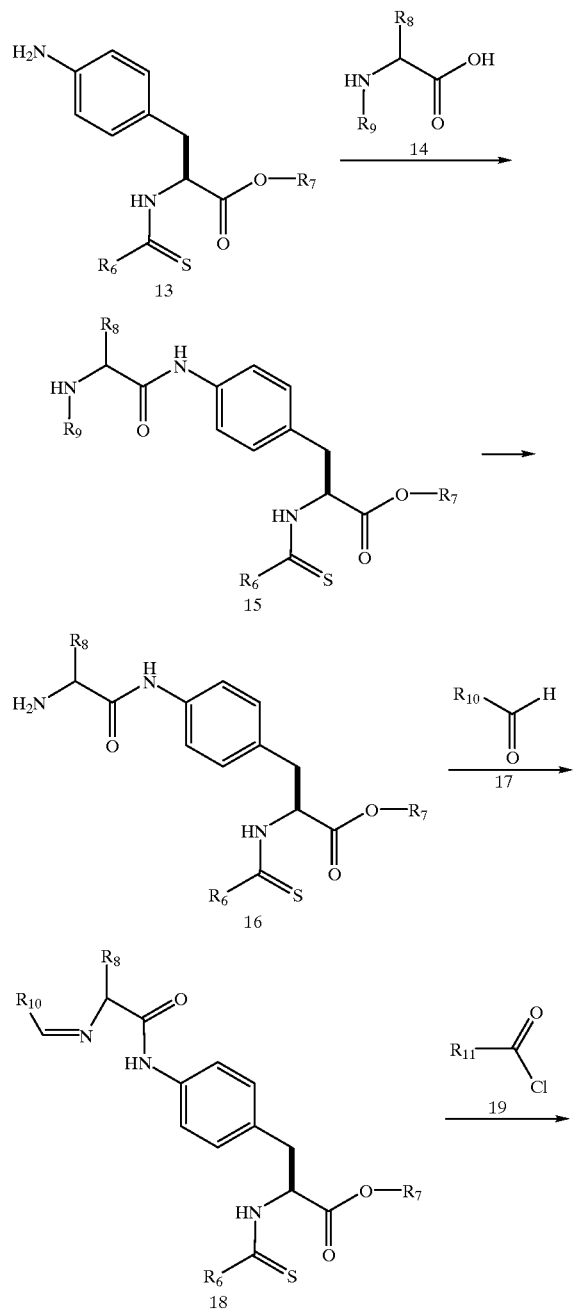

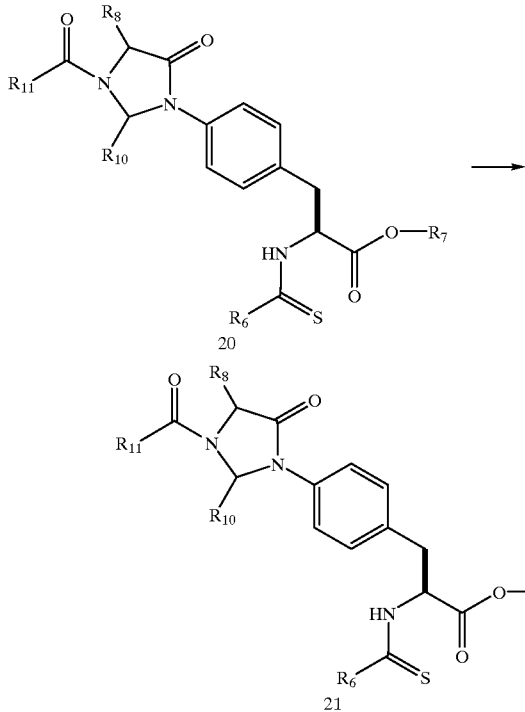

General Melting points were taken on a Thomas-Hoover apparatus and are uncorrected. Optical rotations were determined with a Perkin-Elmer model 241 polarimeter. $^1$H-NMR spectra were recorded with Varian XL-200 and Unityplus 400 MHz spectrometers, using tetramethylsilane (TMS) as internal standard. Electron impact (EI, 70 ev) and fast atom bombardment (FAB) mass spectra were taken on VG Autospec or VG 70E-HF mass spectrometers. Silica gel used for column chromatography was Mallinkrodt SiliCar 230–400 mesh silica gel for flash chromatography; columns were run under a 0–5 psi head of nitrogen to assist flow. Thin layer chromatograms were run on glass thin layer plates coated with silica gel as supplied by E. Merck (E. Merck # 1.05719) and were visualized by viewing under 254 nm UV light in a view box, by exposure to $I_2$ vapor, or by spraying with either phosphomolybdic acid (PMA) in aqueous ethanol, or after exposure to $Cl_2$, with a 4,4'-tetramethyldiaminodiphenylmethane reagent prepared according to E. Von Arx, M. Faupel and M Brugger, *J. Chromatography*, 1976, 120, 224–228.

Reversed phase high pressure liquid chromatography (RP-HPLC) was carried out using either a Waters Delta Prep 4000 employing a 3×30 cm, Waters Delta Pak 15 μM C-18 column at a flow of 40 mL/min employing a gradient of acetonitrile:water (each containing 0.75% TFA) typically from 5 to 95% acetonitrile over 35–40 min or a Rainin HPLC employing a 41.4×300 mm, 8 μM, Dynamax™ C-18 column at a flow of 49 mL/min and a similar gradient of acetonitrile:water as noted above. HPLC conditions are typically described in the format (5-95-35-214); this refers to a linear gradient of from 5% to 95% acetonitrile in water over 35 min while monitoring the effluent with a UV detector set to a wavelength of 214 nM.

Methylene chloride (dichloromethane), 2-propanol, DMF, THF, toluene, hexane, ether, and methanol, were Fisher reagent grade and were used without additional purification except as noted, acetonitrile was Fisher hplc grade and was used as is.

Definitions:
THF is tetrahydrofuran,
DMF is N,N-dimethylformamide,
HOBT is 1-hydroxybenzotriazole,
BOP is [(benzotriazole-1-yl)oxytris-(dimethylamino) phosphonium hexafluorophosphate,
HATU is O-(7-azabenzotriazol-1-yl)-1,1,3,3-tetramethyluronium hexafluorophosphate
HBTU is O-benzotriazole-N,N,N',N',-tetramethyluronium hexafluorophosphate,
DIPEA is diisopropylethylamine,
DMAP is 4-(N,N-dimethylamino)pyridine
DPPA is diphenylphosphoryl azide
DPPP is 1,3-bis(diphenylphosphino)propane
DBU is 1,8-diazabicyclo[5.4.0]undec-7-ene
NaH is sodium hydride
brine is saturated aqueous sodium chloride solution
TLC is thin layer chromatography
LDA is lithium diisopropylamide
BOP-Cl is bis(2-oxo-3-oxazolidinyl)phosphinic chloride
NMP is N-methyl pyrrolidinone Lawesson's reagent is [2,4-bis(4-methoxyphenyl)-1,3-dithia-2,4-diphosphetane-2,4-disulfide]

EXAMPLES

Example 1. N-[[1-(2-methoxyethyl)cyclopentyl]thioxomethyl]-4-nitro-L-phenylalanine methyl ester.

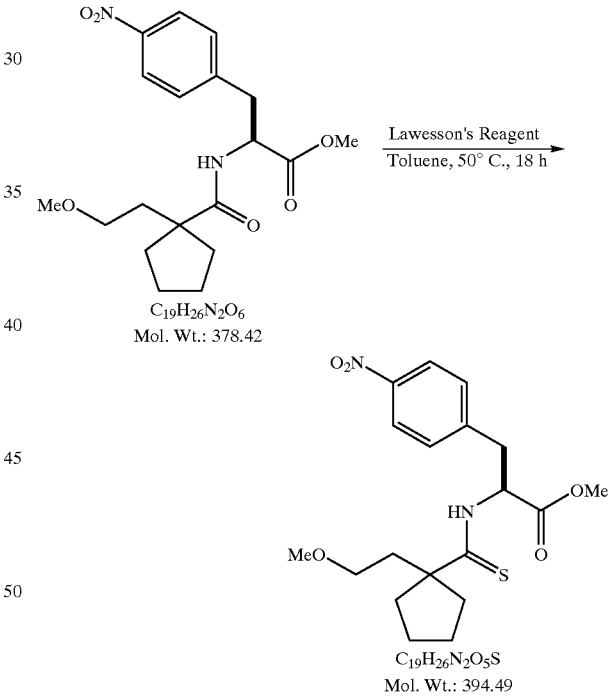

To a solution of [[1-(2-methoxyethyl)cyclopentyl]carbonyl]-4-nitro-L-phenylalanine methyl ester (4.30 g, 11.4 mmol) in toluene (20 mL) was added Lawesson's reagent (2.60 g, 6.27 mmol). The resultant mixture was warmed to 50° C. and stirred for 18 h. The reaction mixture was filtered through a sintered glass funnel and the filtrate was concentrated in vacuo. The residue was by flash column chromatography over silica gel (hexane-ethyl acetate, 9:1 then 8:1) to afford N-[[1-(2-methoxyethyl)cyclopentyl]thioxomethyl]-4-nitro-L-phenylalanine methyl ester (2.44 g, 54%; 70% based on recovered starting material) as a light yellow oil. HR MS: Obs. mass, 395.1639. Calcd. mass, 395.1640 (M+H).

Example 2. 4-[[(2,6-dichlorophenyl)carbonyl]amino]-N-[[1-(2-(methoxyethyl)-cyclopentyl]thioxomethyl]-L-phenylalanine methyl ester.

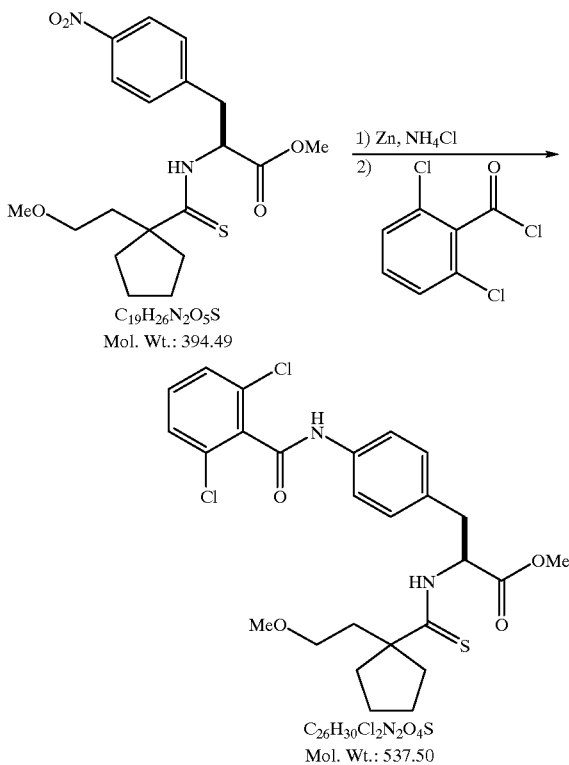

Example 3. 4-[[(2,6-dichlorophenyl)carbonyl]amino]-N-[[1-(2-methoxy-ethyl)cyclopentyl]thioxomethyl]-L-phenylalanine.

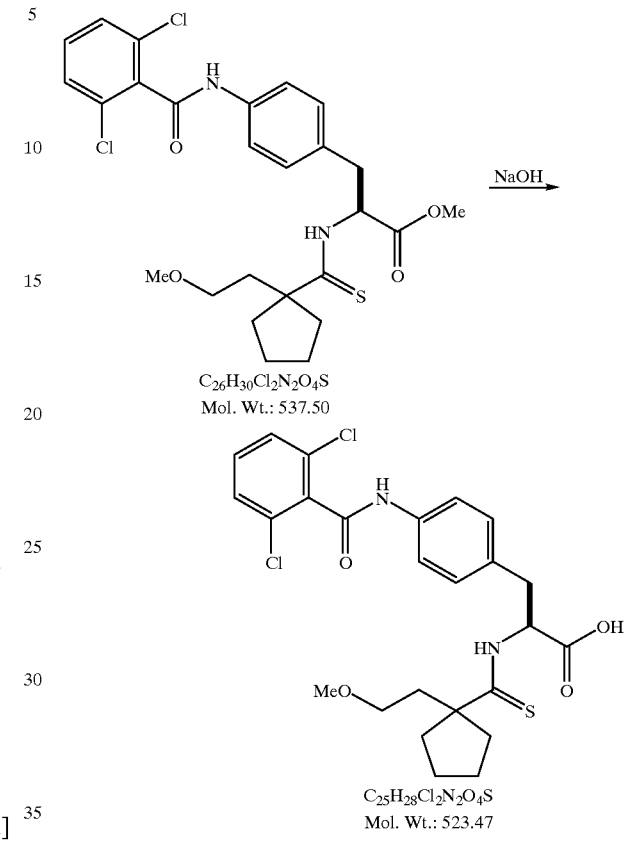

To a suspension of N-[[1-(2-methoxyethyl)cyclopentyl]thioxomethyl[-4-nitro-L-phenylalanine methyl ester (4.58 g, 11.6 mmol), zinc dust (7.50 g, 116 mmol) and ammonium chloride (9.20 g, 174 mmol) in methanol (200 mL) was added $H_2O$ (100 mL) slowly over 5 min. After stirring for 20 min, the reaction mixture was partitioned between ethyl acetate (400 mL) and sat. ammonium chloride solution (150 mL). The separated aqueous layer was back-extracted with ethyl acetate (3×100 mL) and the organic layers were combined, dried over $Na_2SO_4$, filtered and concentrated in vacuo. The residual oil was dried under high vacuum for 2 h to give crude 4-amino-N-[[1-(2-methoxyethyl)cyclopentyl]thioxomethyl]-L-phenylalanine methyl ester (4.5 g).

To a solution of the crude amine obtained above (3.40 g, ~8.77 mmol based on 94% purity) and diisopropylethylamine (1.70 mL, 9.65 mmol) in dichloromethane (15 mL) was added a solution of 2,6-dichlorobenzoyl chloride (1.9 g, 9.21 mmol) in dichloromethane (5 mL). The resultant mixture was stirred overnight, then was concentrated in vacuo and transferred to a separatory funnel containing ethyl acetate (150 mL) and water (40 mL). The aqueous layer was separated and back extracted with ethyl acetate (1×50 mL). The combined organic layer was washed with a sat. solution of $Na_2CO_3$ followed by brine, dried over $MgSO_4$, filtered and concentrated in vacuo. The reaction product by silica gel flash column chromatography (hexane-ethyl acetate, 3:1) to give 4-[[(2,6-dichlorophenyl)carbonyl]amino]-N-[[1-(2-methoxyethyl)cyclopentyl]thioxomethyl]-L-phenylalanine methyl ester (4.50 g, 95%). HR MS: Obs. mass, 559.1201. Calcd. mass, 559.1201 (M+Na).

To a solution of 4-[[(2,6-dichlorophenyl)carbonyl]amino]-N-[[1-(2-methoxyethyl) cyclopentyl]thioxomethyl]-L-phenylalanine methyl ester (4.00 g, 7.44 mmol) in methanol (18 mL) was added a solution of NaOH (421 mg, 10.5 mmol) in water (3 mL). The mixture was stirred for 2 h and then acidified (pH~1–2) with 0.5N HCl. The reaction mixture was poured into a separatory funnel containing ethyl acetate (150 mL) and water (25 mL). The separated aqueous layer was back-extracted with ethyl acetate (2×50 mL). The combined organic layers was washed with brine, dried over $MgSO_4$, filtered and concentrated in vacuo. Purification of the residual material by RP-HPLC (15–95% acetonitrile-water gradient over 25 min) provided 4-[[(2,6-dichlorophenyl)carbonyl]amino]-N-[[1-(2-methoxyethyl) cyclopentyl]thioxomethyl]-L-phenylalanine (3.05 g, 78%). HR MS: Obs. mass, 545.1043. Calcd. mass, 545.1045 (M+Na).

Example 4. 1-(2-azidoethyl)cyclopentanecarboxylic acid.

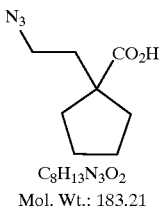

To an ice cold solution of diisopropylamine (56 mL, 0.396 mol) in THF (85 mL) was added n-butyl lithium in hexane solution (240 mL, 1.6 M, 0.393 mol) over 20 min. The mixture was stirred at 0° C. for 30 min, cooled to a bath temperature of −65° C. and ethyl cyclopentanecarboxylate (37.4 g, 0.263 mol) in THF (50 mL) was added over 20 min. After 1 h, a solution of 1,2-dibromoethane (47 mL, 0.545 mol) in THF (50 mL) was added, the mixture was held at -65 ° C for 3 h and then was allowed to warm to room temperature overnight. After the reaction was quenched by addition of saturated ammonium chloride solution (200 mL), the layers were separated and the aqueous layer was extracted with ethyl acetate (100 mL). The combined extracts were washed with 1:1 brine:water (250 mL) and were dried ($Na_2SO_4$). The solution was filtered, concentrated in vacuo then the residue was diluted with toluene (100 mL) and concentrated. The dilution and concentration cycle was repeated twice to give ethyl 1-(2-bromoethyl) cyclopentanecarboxylate (52.5 g).

A solution of the above bromide (52.5 g, 0.211 mol) and sodium azide (54 g, 0.831 mol) in DMF (200 mL) was stirred at 50° C. for 5 h under a nitrogen atmosphere and was filtered. The filtrate was concentrated to near dryness, diluted with ethyl acetate (500 mL), filtered and concentrated to give crude ethyl 1-(2-azidoethyl) cyclopentanecarboxylate (40.9 g) as a brown oil. This material was combined with product from a previous run (total 63.5 g) and was purified by chromatography over 250 g of silica gel (5% ethyl acetate in hexane) to give 50.3 g of product as a light brown oil.

The oil from above (50.3 g, 0.238 mol) was dissolved in THF (750 mL) and methanol (375 mL) and a solution of LiOH hydrate (15 g, 0.357 mol) in water (300 mL) was added. The resulting solution was stirred at 40° C. overnight and concentrated. The residue was dissolved in 2 L of water containing 40 mL of 1N NaOH and was washed with hexane (1 L). The aqueous layer was treated with 1 N HCl (375 mL) and was extracted with diethyl ether (2×1 L). The combined extracts were dried ($Na_2SO_4$), filtered and concentrated under reduced pressure to give 1-(2-azidoethyl) cyclopentane carboxylic acid (37.5 g) as an amber liquid.

Example 5. N-[[1-(2-azidoethyl)cyclopentyl]carbonyl]-4-nitro-L-phenylalanine methyl ester.

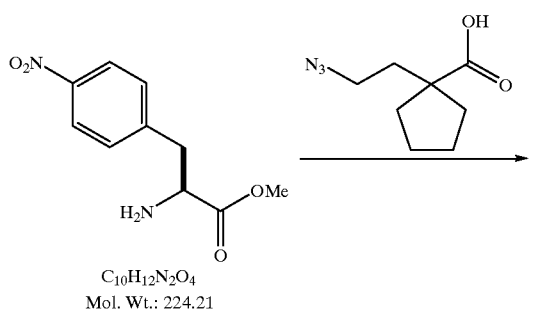

$C_{10}H_{12}N_2O_4$
Mol. Wt.: 224.21

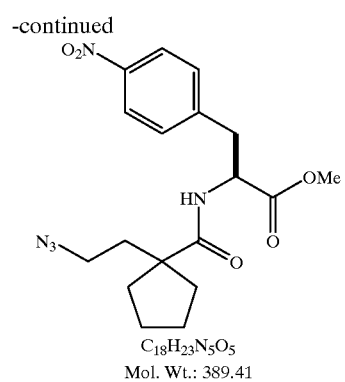

$C_{18}H_{23}N_5O_5$
Mol. Wt.: 389.41

A solution of 4-nitro-L-phenylalanine methyl ester hydrochloride (3.0 g, 11.5 mmol), 1-(2-azidoethyl)cyclopentane carboxylic acid (2.3 g, 12.7 mmol) and BOP (5.34 g, 12.1 mmol) in dichloromethane (6 mL) and DMF (4 mL) was treated with diisopropylethylamine (4.2 mL, 24.2 mmol). The mixture was stirred overnight at which time TLC (1:1 hexane:ethyl acetate) indicated no more starting material. The mixture was diluted with water, extracted with ethyl acetate. The extracts were washed with water and brine, then were dried ($Na_2SO_4$), filtered and evaporated in vacuo. The residue was purified by chromatography over silica gel (3:1 hexane:ethyl acetate) to afford 4.26 g of N-[[1-(2-azidoethyl)cyclopentyl]carbonyl]-4-nitro-L-phenylalanine methyl ester.

Example 6. N-[[1l-[2-[[(1,1l-dimethylethoxy)carbonyl]amino]ethyl]cyclopentyl]carbonyl]-4-nitro-L-phenylalanine methyl ester.

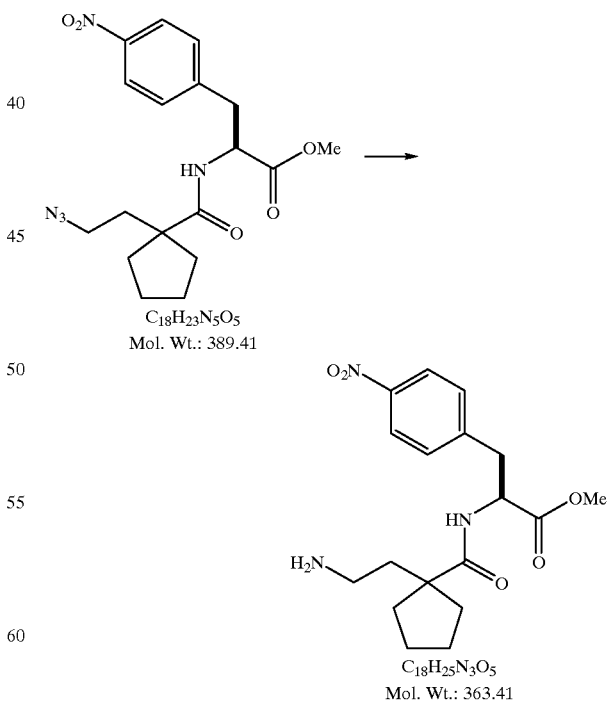

a. A solution of N-[[1-(2-azidoethyl)cyclopentyl]carbonyl]-4-nitro-L-phenylalanine methyl ester (1.92 g, 4.93 mmol) in THF (20 mL) was treated dropwise with a 1 M solution of trimethylphosphine in THF. After the addition was complete, the mixture was stirred for 20 min and water (0.17 mL) was added. The reaction was stirred a further 2 h, then a little trifluoroacetic acid was added and the mixture was dried over sodium sulfate and concentrated.

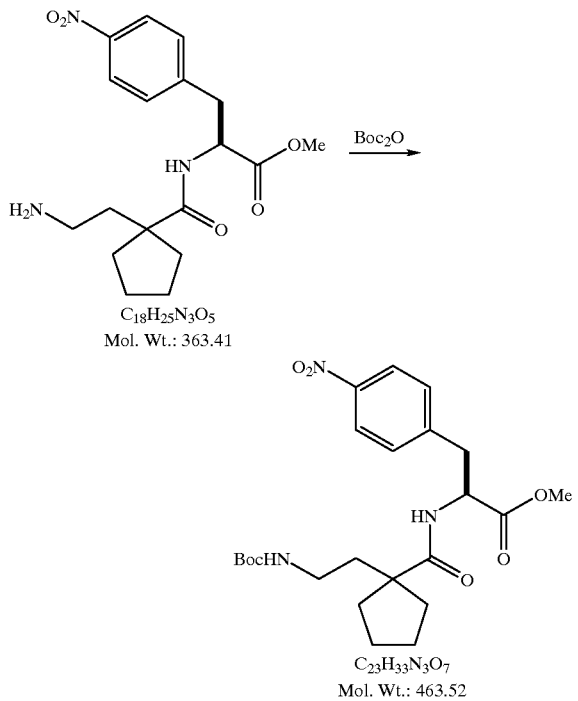

b. To a solution of N-[[1-(2-aminoethyl)cyclopentyl] carbonyl]-4-nitro-L-phenylalanine methyl ester trifluoroacetic acid salt (2.35 g, 4.93 mmol) in dioxane (25 mL) was added diisopropylethylamine (0.860 mL, 4.93 mmol) and di-tert-butyl dicarbonate (1.08 g, 4.93 mmol). The resultant mixture was stirred for 18 h. The reaction mixture was filtered through a sintered glass funnel and the filtrate was concentrated in vacuo. Purification of the residual material by silica gel flash column chromatography (hexane-ethyl acetate 3:1) afforded N-[[1-[2-[[(1,1-dimethylethoxy) carbonyl]amino]ethyl]cyclopentyl]carbonyl]-4-nitro-L-phenylalanine methyl ester (2.20 g, 95%). HR MS: Obs. mass, 464.2397. Calcd. mass, 464.2397 (M+H).

Example 7. N-[[1-[2-[[(1,1-dimethylethoxy) carbonylamino]ethyl]cyclopentyl]thioxomethyl]-4-nitro-L-phenylalanine methyl ester.

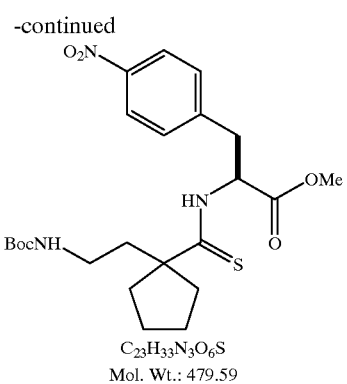

To a solution of N-[[1-[2-[[(1,1-dimethylethoxy)carbonyl] amino]ethyl]cyclopentyl]carbonyl]-4-nitro-L-phenylalanine methyl ester (1.00 g, 2.16 mmol) in toluene/dioxane (1: 1, 10 mL) was added Lawesson's reagent (0.524 g, 1.29 mmol). The resultant mixture was warmed to 50° C. and was stirred for 24 h. The reaction mixture was filtered through a sintered glass funnel and the filtrate was concentrated in vacuo. Purification of the crude product by silica gel flash column chromatography (hexane-ethyl acetate, 6:1 then 4:1), afforded N-[[1-[2-[[(1,1-dimethylethoxy)carbonyl]amino] ethyl]cyclopentyl]thioxomethyl]-4-nitro-L-phenylalanine methyl ester (460 mg, 44%; 65% based on recovered starting material) as a light yellow oil. HR MS: Obs. mass, 478.2014. Calcd. mass, 478.2012 (M−H).

Example 8. N-[[1-[2-(acetylamino)ethyl] cyclopentyl]thioxomethyl]-4-nitro-L-phenylalanine methyl ester.

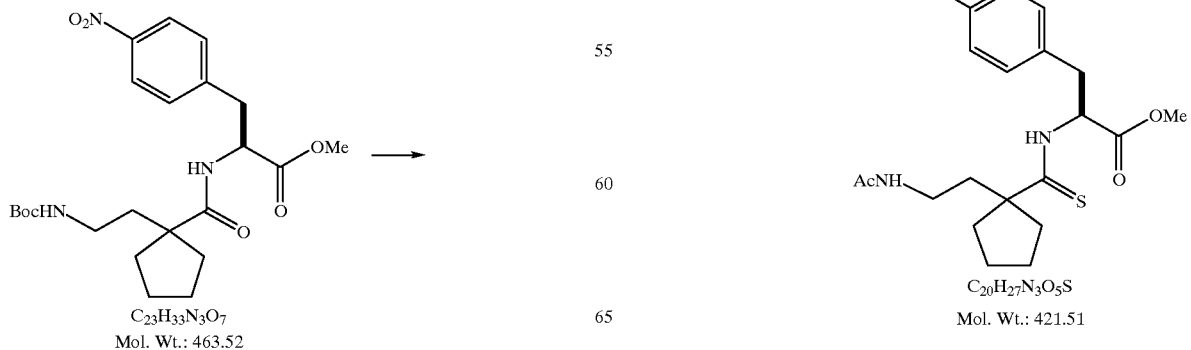

To a solution of N-[[1-[2-[[(1,1-dimethylethoxy)carbonyl]amino]ethyl]-cyclopentyl]thioxomethyl]-4-nitro-L-phenylalanine methyl ester (1.26 g, 2.63 mmol) in dichloromethane (15 mL) was added dropwise trifluoroacetic acid (7 mL) and the resultant mixture was stirred for 2 h at room temperature. The reaction mixture was concentrated in vacuo to afford the trifluoroacetic acid salt of crude N-[[1-(2-aminoethyl)-cyclopentyl]thioxomethyl]-4-nitro-L-phenylalanine methyl ester as a yellow oil (1.4 g).

To a solution of the salt obtained above (1.4 g,~2.63 mmol) in dichloromethane (10 mL) was added diisopropylethylamine (1.37 mL, 7.88 mmol) and acetic anhydride (0.250 mL, 2.63 mmol). The resultant mixture was stirred overnight. The reaction mixture was concentrated in vacuo and transferred to a separatory funnel containing ethyl acetate (100 mL) and water (40 mL). The aqueous layer was separated and back extracted with ethyl acetate (1×50 mL). The combined organic layer was washed with brine, dried over $MgSO_4$, filtered and concentrated in vacuo. The resulting residue was purified by flash column chromatography (dichloromethane-acetone, 5:1) to furnish N-[[1-[2-(acetylamino)ethyl]cyclopentyl]thioxomethyl]-4-nitro-L-phenylalanine methyl ester (743 mg, 67%). HR MS: Obs. mass, 422.1744. Calcd. mass, 422.1750 (M+H).

Example 9. 4-amino-N-[[1-[2-acetylamino)ethyl]cyclopentyl]thioxomethyl]-L-phenylalanine methyl ester.

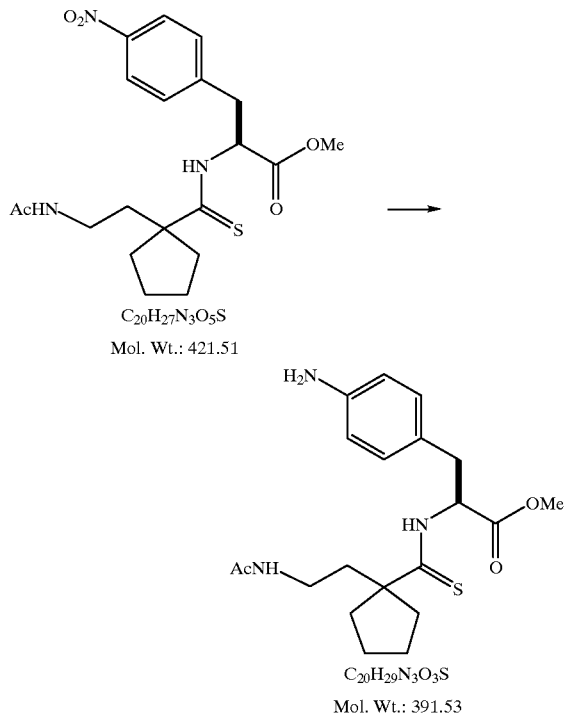

To a suspension of N-[[1-[2-(acetylamino)ethyl]cyclopentyl]thioxomethyl]-4-nitro-L-phenylalanine methyl ester (740 mg, 1.75 mmol), zinc dust (1.14 g, 17.5 mmol) and ammonium chloride (1.41 g, 26.3 mmol) in methanol (20 mL) was added $H_2O$ (10 mL) slowly over 5 min. After stirring for 20 min, the reaction mixture was diluted with ethyl acetate (80 mL) and sat. ammonium chloride solution (25 mL). The separated aqueous layer was back-extracted with ethyl acetate (3×25 mL) and the organic layers were combined, dried over $Na_2SO_4$, filtered and concentrated in vacuo. The residual oil was dried under high vacuum for 2 h to give the crude amine (750 mg)which was by flash silica gel column chromatography (dichloromethane-acetone 2:1) to furnish 4-amino-N-[[1-[2-acetylamino)ethyl]cyclopentyl]thioxomethyl]-L-phenylalanine methyl ester (650 mg, 95%). HR MS: Obs. mass, 392.2016. Calcd. mass, 392.2008 (M+H).

Example 10. N-[[1-[2-(acetylamino) ethyl] cyclopentyl]thioxomethyl]-4-[[(2,6-dichlorophenyl) carbonyl]amino]-L-phenylalanine.

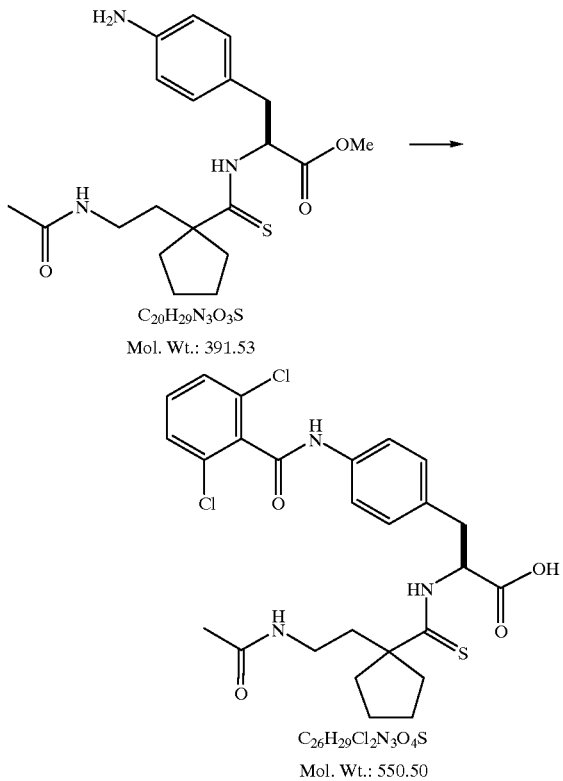

To a solution of 4-amino-N-[[1-[2-(acetylamino)ethyl]cyclopentyl]thioxomethyl]-L-phenylalanine methyl ester (195 mg, 0.498 mmol) and diisopropylethylamnine (0.0950 mL, 0.548 mmol) in dichloromethane (1 mL) was added a solution of 2,6-dichlorobenzoyl chloride (110 mg, 0.523 mmol) in dichloromethane (1 mL). The resultant mixture was stirred overnight then was concentrated in vacuo and transferred to a separatory funnel containing ethyl acetate (50 mL) and water (10 mL). The separated aqueous layer back-extracted with ethyl acetate (1×25 mL). The combined organic layer was washed in turn sat. solution of $Na_2CO_3$ and brine, then was dried over $MgSO_4$, filtered and concentrated in vacuo to provide crude N-[[1-[2-(acetylamino) ethyl]cyclopentyljthioxomethyl]-4-[[(2,6-dichlorophenyl) carbonyl]amino-L-phenylalanine methyl ester (300 mg).

To a solution of the above methyl ester (300 mg, ~0.498 mmol) in methanol (1 mL) was added a solution of NaOH (64 mg, 14.9 mmol) in water (1 mL). The mixture was stirred for 2 h and was then acidified (pH 1–2) with 0.5M HCl. The reaction mixture was poured into a separatory funnel containing ethyl acetate (50 mL) and water (10 mL) and the separated aqueous layer was back-extracted with ethyl acetate (2×25 mL). The combined organic layers were washed with brine, dried over $MgSO_4$, filtered and concentrated in vacuo. Purification of the crude by RP-HPLC (15–95% acetonitrile-water gradient over 25 min) and lyophylization of the appropriate fractions, provided N-[[1-[2-(acetylamino) ethyl]cyclopentylithioxomethyl]-4-[[(2,6-dichlorophenyl)carbonyl]amino]-L-phenylalanine (126 mg, 46%) as a colorless solid. HR MS: Obs. mass, 550.1330. Calcd. mass, 550.1334 (M+H).

Example 11. 4-[[(2,6-dichlorophenyl)carbonyl]amino]-N-[[1-[2-[[(methylamino)carbonyl]amino]ethyl]cyclopentyl]thioxomethyl]-L-phenylalanine.

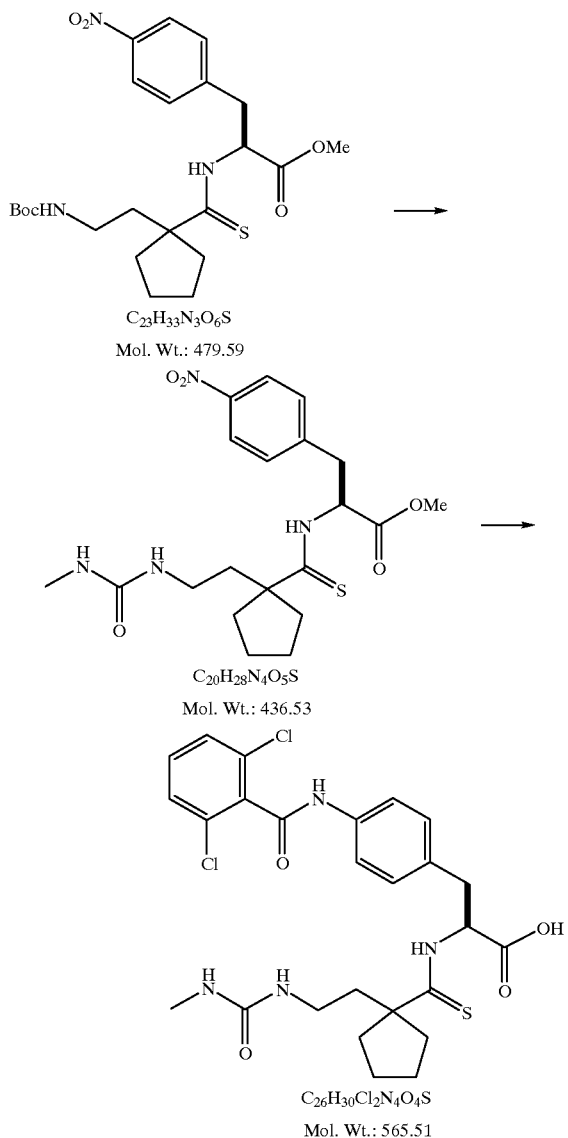

4-[[(2,6-dichlorophenyl)carbonyl]amino]-N-[[1-[2-[[(methylamino)carbonyl]amino]ethyl]cyclopentyl]thioxomethyl]-L-phenylalanine was prepared from N-[[1-[2-[[(1,1-dimethylethoxy)carbonyl]amino]ethyl]cyclopentyl]thioxomethyl]-4-nitro-L-phenylalanine methyl ester and methyl isocyanate by using the general procedure described in examples 8 to 10. HR MS: Obs. mass, 565.1436. Calcd. mass, 565.1443 (M+H).

Example 12. 2-chloro-6-methylbenzaldehyde.

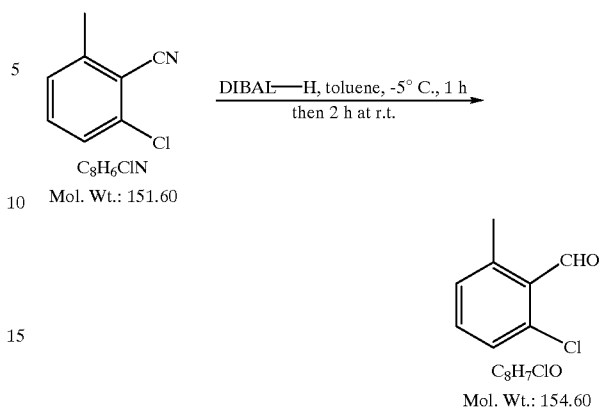

A 500 mL, three-necked, round bottomed flask equipped with a magnetic stirrer, thermometer, addition funnel, and argon inlet was charged with 75 g (494 mmol) of 2-chloro-6-methylbenzonitrile and 400 mL of toluene (stored over 4 Å molecular sieves). The mixture was cooled to −2° C. (ice/acetone bath) and a 1M solution of DIBAL-H in hexanes (593 mmol, 593 mL) was added dropwise over a period of 30 min while maintaining the temperature below 0° C. After the addition was completed, the reaction mixture was stirred for 1 h at 0° C. and then allowed to warm to room temperature. After 2 h at room temperature, TLC analysis indicated the absence of starting material (4:1 hexane:diethyl ether, phosphomolybdic acid spray, as analysis by UV fluorescence was misleading). The reaction was poured into a mixture of ice (2000 g) and concentrated sulfuric acid (50 mL) and was stirred for overnight. The precipitated solids were collected by filtration and the filtrate was extracted with diethyl ether (2×200 mL). The combined extracts were washed with brine, dried (MgSO$_4$) and filtered. Evaporation of the solvent under reduced pressure gave the crude aldehyde, which was combined with the above solid to afford 71.31 g (93%) of light yellow colored aldehyde suitable for use in the next step.

Example 13. 2-chloro-6-methylbenzoic acid.

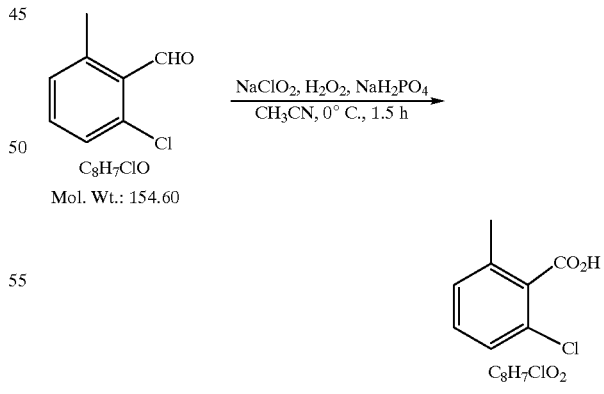

A 1000 mL, three-necked, round bottomed flask equipped with a magnetic stirrer, thermometer, addition funnel, and argon inlet was charged with 2-chloro-6-methylbenzaldehyde (71.31 g, 461 mmol, crude obtained from the above experiment) and 750 mL of acetonitrile. To this suspension, a solution of monobasic sodium phosphate (115 mmol, 15.9 g) in water 240 mL) was added followed by hydrogen peroxide (50 mL, 30%) at room temperature. Then, a solution of sodium chlorite (73.5 g, 811 mmol) in water (700 mL) was added dropwise at 0° C. while maintaining the temperature below 3° C. After the addition was complete, the yellow suspension was stirred for 15 h at 0° C. to room temperature. TLC analysis of the mixture indicated the absence of starting material. A solution of sodium bisulfite (73 g, 701 mmol) in water (200 mL) was added dropwise at 0° C. until the yellow color disappeared (KI-paper positive). Cooling was maintained throughout to control the exothermic reaction. The solvent was removed under vacuum to afford a colorless solid. The solid was collected by filtration and the filtrate was extracted with diethyl ether (200 mL). The above solid was dissolved in the combined diethyl ether extracts which were then washed with 10% NaOH solution (2×200 mL). The combined aqueous washings were acidified with 10% HCl to pH 1. The resulting colorless precipitate was collected by filtration and air-dried to afford 54.88 g (65%, overall in two steps) of 2-chloro-6-methylbenzoic acid as a colorless solid.

Example 14. N-[(2-chloro-6-methylphenyl)carbonyl]-4-nitro-L-phenylalanine methyl ester.

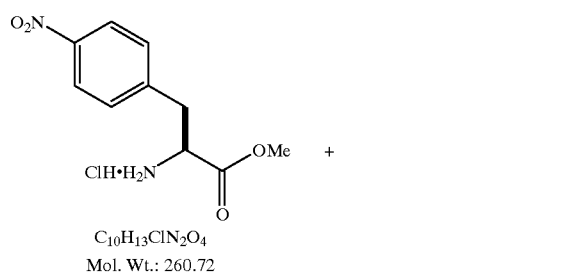

To a solution of 4-nitro-L-phenylalanine methyl ester hydrochloride salt (7.44 mmol, 1.94 g), 2-chloro-6-methylbenzoic acid (8.2 mmol, 1.4 g) and HBTU (8.2 mmol, 3.11 g) in DMF (27 mL) was added diisopropylethylamine (18.6 mmol, 3.24 mL) at room temperature. The clear solution was stirred for 48 h at room temperature and was diluted with 100 mL of ethyl acetate. The solution was washed in turn with 0.5N hydrochloric acid (2×50 mL), saturated sodium bicarbonate solution (2×50 mL), brine (100 mL) then was dried (MgSO$_4$) and filtered. Concentration of the solution to dryness gave 2.67 g (95%) of N-[(2-chloro-6-methylphenyl)carbonyl]-4-nitro-L-phenylalanine methyl ester as a colorless solid, mp 120–123° C. HRMS: Obs. mass, 376.4274. Calcd. mass, 376.4238 (M+H).

Example 15. N-[(2-chloro-6-methylphenyl)thioxomethyl]-4-nitro-L-phenylalanine methyl ester.

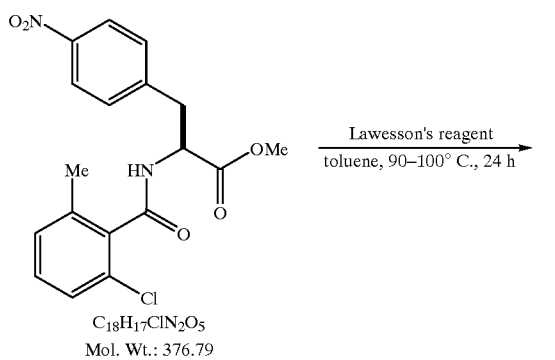

To a mixture of N-[(2-chloro-6-methylphenyl)carbonyl]-4-nitro-L-phenylalanine methyl ester (9.66 mmol, 3.64 g) and Lawesson's reagent (6.0 mmol, 2.46 g, 0.62 equiv.) was added toluene (15 mL, which had been stored over 4 Å molecular sieves) at room temperature. The suspension was heated to 90–100° C. and was stirred for 24 h. Examination of the resulting clear solution by TLC failed to detect the presence of starting material. The reaction mixture was diluted with ethyl acetate (50 mL) and washed with water (50 mL), saturated sodium bicarbonate solution (50 mL), and brine (50 mL). The organic extract was dried (MgSO$_4$) filtered and evaporated under reduced pressure. The crude compound was purified by careful silica gel column chromatography (hexane:ethyl acetate, 4:1 to 2:1) to obtain 1.52 g (40%) of N-[(2-chloro-6-methylphenyl)thioxomethyl]-4-nitro-L-phenylalanine methyl ester as a yellow solid, mp 150–153° C. (triturated from diethyl ether/ hexane 3:1 ratio). HRMS: Obs. mass, 393.0685. Calcd. mass, 393.0677 (M+H).

Example 16. 4-amino-N-[(2-chloro-6-methylphenyl)thioxomethyl]-L-phenylalanine methyl ester.

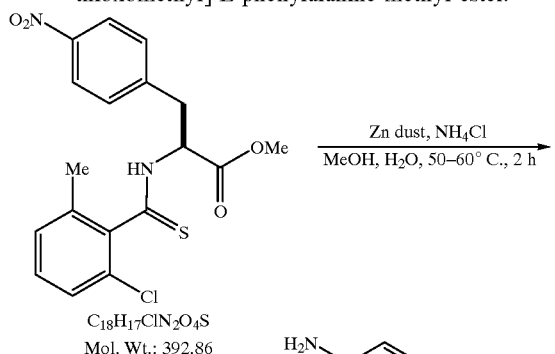

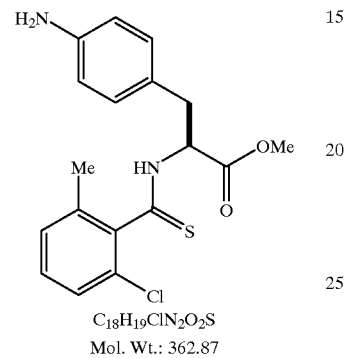

C<sub>18</sub>H<sub>19</sub>ClN<sub>2</sub>O<sub>2</sub>S
Mol. Wt.: 362.87

To a mixture of N-[(2-chloro-6-methylphenyl)thioxomethyl]-4-nitro-L-phenylalanine methyl ester (3.86 mmol, 1.52 g), zinc dust ([325 mesh, 39.0 mmol, 2.55 g, 10 equiv.) and ammonium chloride (58.0 mmol, 3.09 g, 15 equiv.) was added methanol (50 mL) and water (25 mL) at room temperature. After addition of water, an exothermic reaction ensued and the temperature rose to between 45 and 50° C. After the suspension was stirred for 2 h at a bath temperature of 50–60° C., TLC analysis of the mixture indicated the absence of starting material. The reaction mixture was filtered through a pad of celite and the filter cake was washed with methanol(50 mL) and water (40 mL). The filtrate was concentrated under vacuum to remove methanol and the product was extracted into ethyl acetate (2×50 mL). The combined extracts were washed with brine (50 mL), dried (MgSO<sub>4</sub>), filtered and concentrated in vacuo to give 1.3 g (92%) of 4-amino-N-[(2-chloro-6-methylphenyl)thioxomethyl]-L-phenylalanine methyl ester as an amorphous yellow solid, which was used directly for next step. HRMS: Obs. mass, 363.0932. Calcd. mass, 363.0934 (M+H).

Example 17. N-[(2-chloro-6-methylphenyl)thioxomethyl]-4-[[(2,6-dichlorophenyl)carbonyl]amino]-L-phenylalanine methyl ester.

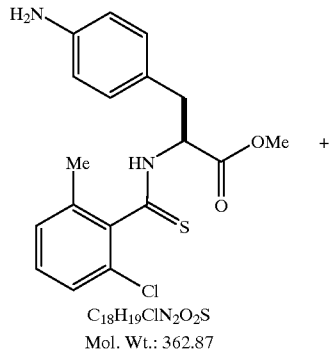

C<sub>18</sub>H<sub>19</sub>ClN<sub>2</sub>O<sub>2</sub>S
Mol. Wt.: 362.87

+

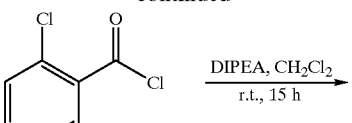

C<sub>7</sub>H<sub>3</sub>Cl<sub>3</sub>O
Mol. Wt.: 209.46

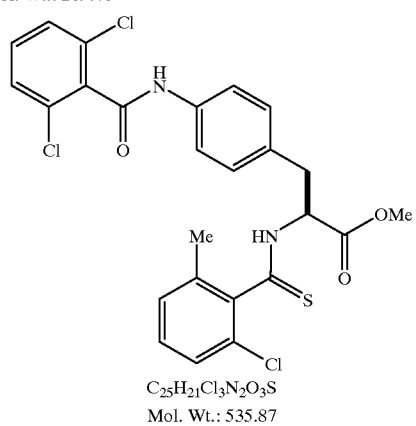

C<sub>25</sub>H<sub>21</sub>Cl<sub>3</sub>N<sub>2</sub>O<sub>3</sub>S
Mol. Wt.: 535.87

To a solution of 4-amino-N-[(2-chloro-6-methylphenyl)thioxomethyl]-L-phenylalanine methyl ester (3.57 mmol, 1.296 g) and 2,6-dichlorobenzoyl chloride (3.75 mmol,0.785 g) in dichloromethane (20 mL) was added diisopropylethylamine (5.35 mmol, 0.93 mL) at room temperature. The solution was stirred for 15 h at which time TLC analysis of the mixture indicated the absence of starting material. After the addition of water (30 mL), the layers were separated and the aqueous phase was extracted with dichloromethane (20 mL). The combined extracts were washed with brine (50 mL), dried (MgSO<sub>4</sub>) and concentrated under reduced pressure. The residue was purified by silica gel column chromatography ( hexane:ethyl acetate, 4:1 to 1:1) to obtain 1.91 g (83%) of N-[(2-chloro-6-methylphenyl)thioxomethyl]-4-[[(2,6-dichlorophenyl)carbonyl]amino]-L-phenylalanine methyl ester as an amorphous colorless solid. HRMS: Obs. mass, 535.0399. Calcd. mass, 535.0416 (M+H).

Example 18. 4-[[(2,6-dichlorophenyl)carbonyl]amino]-N-[(2-chloro-6-methylphenyl)thioxomethyl]-L-phenylalanine.

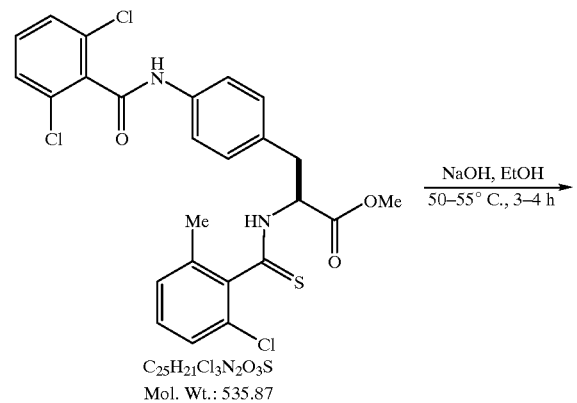

C<sub>25</sub>H<sub>21</sub>Cl<sub>3</sub>N<sub>2</sub>O<sub>3</sub>S
Mol. Wt.: 535.87

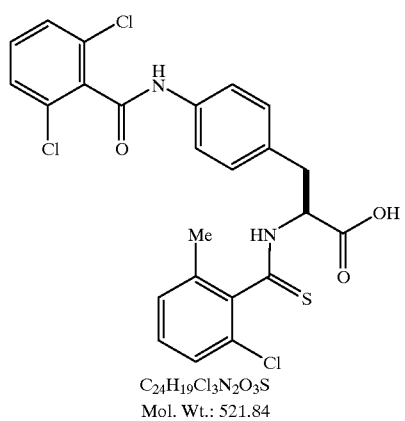

C₂₄H₁₉Cl₃N₂O₃S
Mol. Wt.: 521.84

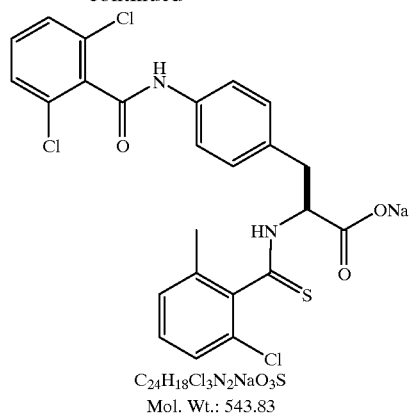

C₂₄H₁₈Cl₃N₂NaO₃S
Mol. Wt.: 543.83

To a suspension of N-[(2-chloro-6-methylphenyl) thioxomethyl]-4-[[(2,6-dichlorophenyl)carbonyl]amino]-L-phenylalanine methyl ester (2.89 mmol, 1.55 g) in ethanol (8 mL) was added aqueous 1.0N sodium hydroxide (5 mL) at room temperature. The mixture was heated to 50–55° C. and the resulting clear solution was stirred for 3–4 h. TLC analysis of the mixture indicated the absence of starting material. The mixture was concentrated to remove ethanol, then was diluted with 15 mL of water and extracted with 25 mL of diethyl ether to remove any neutral impurities. The aqueous layer was acidified with 1N HCl and the precipitated colorless solid was extracted into ethyl acetate (2×30 mL). The combined extracts were washed with brine, dried (MgSO₄) and concentrated in vacuo to afford 1.45 g (96%) of N-[(2-chloro-6-methylphenyl)thioxomethyl]-4-[[(2,6-dichlorophenyl)carbonyl]amino]-L-phenylalanine as an amorphous colorless solid. HRMS: Obs. mass, 521.0241. Calcd. mass, 521.0260 (M+H).

Example 19. N-[(2-chloro-6-methylphenyl) thioxomethyl]-4-[[(2,6-dichlorophenyl)carbonyl] amino]-L-phenylalanine sodium salt.

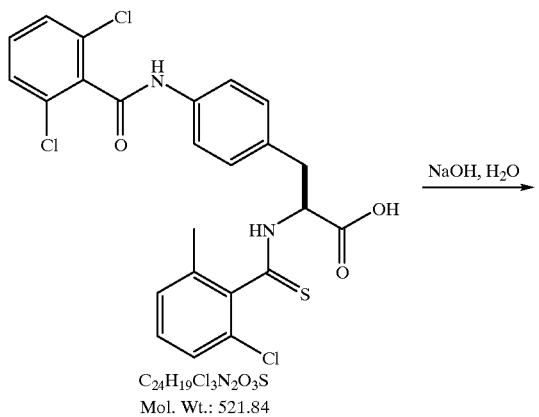

C₂₄H₁₉Cl₃N₂O₃S
Mol. Wt.: 521.84

N-[(2-chloro-6-methylphenyl)thioxomethyl]-4-[[(2,6-dichlorophenyl)carbonlyllaminlo]-L-phenylalanine (2.77 mmol, 1.45 g) was dissolved in water (10 mL) containing 1.5 equivalents of aqueous 1.0N sodium hydroxide (4.2 mL) at room temperature. The solution was loaded into a reverse phase column size of 8 inches length with 1.5 inches diameter containing C-18 silica gel and eluted with water to remove excess base. The product was eluted with 5–20% methanol in water. After the appropriate fractions were combined and concentrated, the residue was dissolved in 50 mL water and lyophilized to afford 1.3 g of the sodium salt as a colorless amorphous solid. HRMS: Obs. mass, 543.0076. Calcd. mass, 543.0079 (M+H).

Example 20. 2-ethyl-6-methylbenzoic acid.

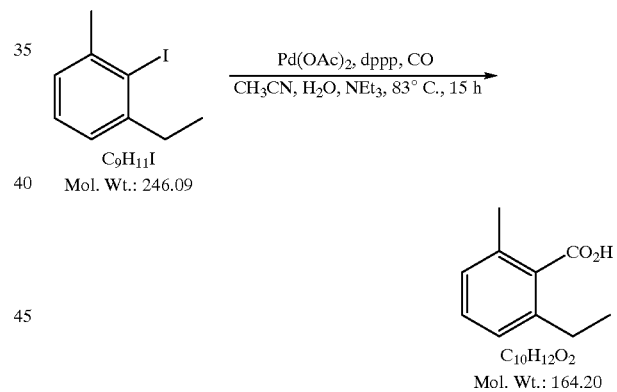

A 250 mL pressure bottle was charged with 2-ethyl-6-methyliodobenzene (30.07 mmol, 7.4 g), Pd(OAc)₂ (1.43 mmol, 334 mg) and dppp (1.43 mmol, 620 mg). The flask was closed with a septum and evacuated three times with argon. Acetonitrile (96 mL), triethylamine (189 mmol, 19.0 g, 26.25 mL) and water (19.1 mL) were added in succession by the aid of syringe and the rubber septum was replaced with a teflon lined cap connected to a carbon monoxide source. The flask was now pressurized with carbon monoxide (40 psi) and the excess pressure was released. This process was repeated three times and finally the mixture was stirred for 5 min under 40 psi carbon monoxide pressure. The flask was then disconnected from the carbon monoxide cylinder and immersed in a preheated oil bath (83–85° C). The reaction mixture turned black within 1 h and was stirred for another 14 h at this temperature, then was cooled to room temperature and the pressure was released. The resulting mixture was diluted with diethyl ether (200 mL) and 1.0N NaOH (20 mL). The formed sodium was extracted into water (2×100 mL). The combined water extracts were acidified with 1.0N HCl and the mixture was extracted with dichloromethane (3×100 mL). The combined dichloromethane extracts were washed with brine, dried (MgSO$_4$), filtered and the volatiles were removed under vacuum to provide 3.58 g (72.5%) of 2-ethyl-6-methylbenzoic acid as a viscous brown oil which slowly solidified overnight. HR MS: Obs. mass, 164.0833. Calcd. mass, 164.0837 (M+).

Example 21. N-[(2-ethyl-6-methylphenyl)carbonyl]-4-nitro-L-phenylalanine methyl ester.

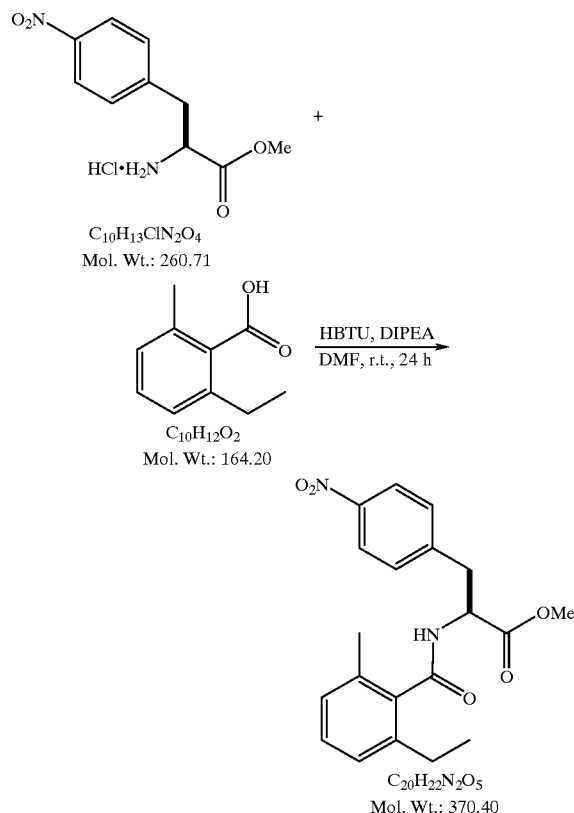

Using the procedure described in example 14, N-[(2-ethyl-6-methylphenyl)carbonyl]-4-nitro-L-phenylalanine methyl ester was prepared in 72% yield as a colorless solid, mp 119–121° C. HR MS: Obs. mass, 371.1610. Calcd. mass, 371.1607 (M+H).

Example 22. N-[(2-ethyl-6-methylphenyl)thioxomethyl]-4-nitro-L-phenylalanine methyl ester.

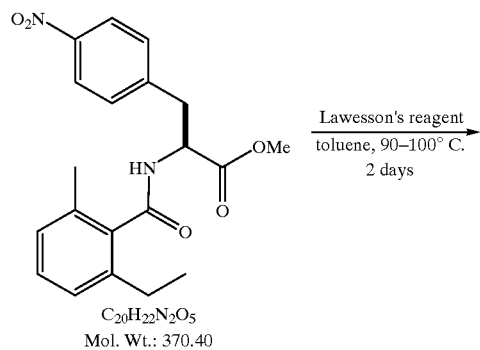

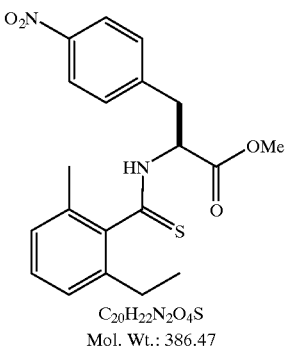

Using the procedure described in example 15, N-[(2-ethyl-6-methylphenyl)thioxomethyl]-4-nitro-L-phenylalanine methyl ester was prepared in 47% yield as an amorphous colorless solid. HR MS: Obs. mass, 387.1383. Calcd. mass, 387.1378 (M+H).

Example 23. 4-amino-N-[(2-ethyl-6-methylphenyl)thioxomethyl]-L-phenylalanine methyl ester.

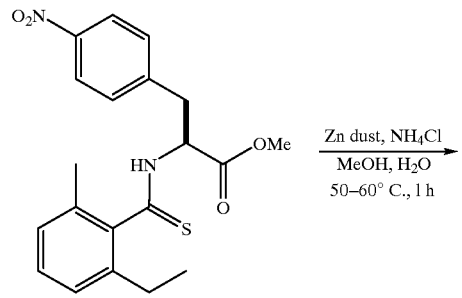

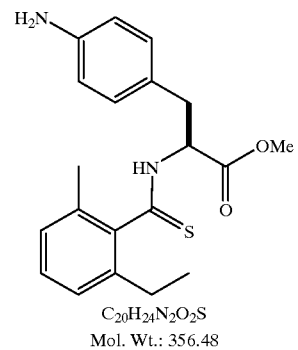

Using the general procedure described in example 16, 4-amino-N-[(2-ethyl-6-methylphenyl)thioxomethyl]-L-phenylalanine methyl ester was prepared in 94% yield as an amorphous colorless solid. HR MS: Obs. mass, 357.1640. Calcd. mass, 357.1638 (M+H).

Example 24. 4-[[(2,6-dichlorophenyl)carbonyl]amino]-N-[(2-ethyl-6-methylphenyl)thioxomethyl]-L-phenylalanine methyl ester.

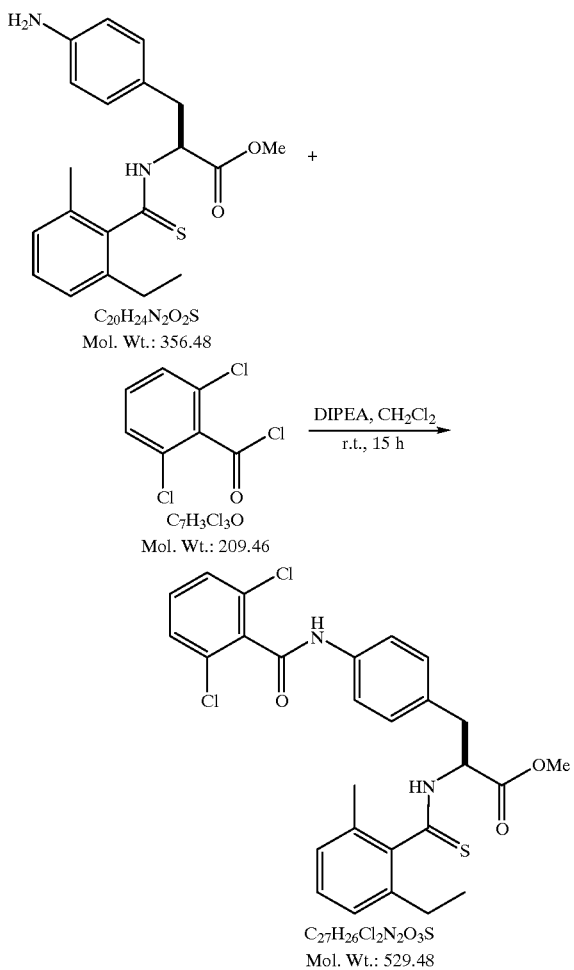

Using the procedure described in example 17, 4-[[(2,6-dichlorophenyl)carbonyl]amino]-N-[(2-ethyl-6-methylphenyl)thioxomethyl]-L-phenylalanine methyl ester was prepared in 70% yield as an amorphous colorless solid. HR MS: Obs. mass, 529.1094. Calcd. mass, 529.1119 (M+H).

Example 25. 4-[[(2,6-dichlorophenyl)carbonyl]amino]-N-[(2-ethyl-6-methylphenyl)thioxomethyl]-L-phenylalanine.

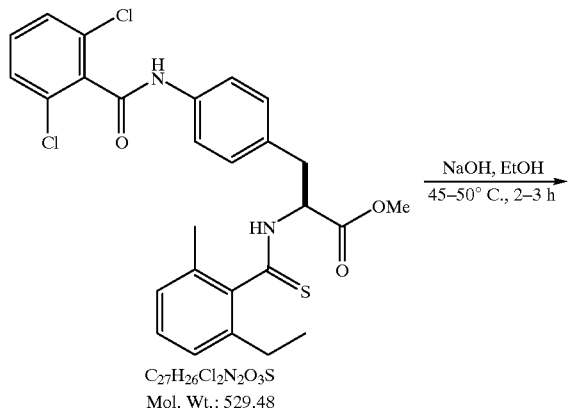

-continued

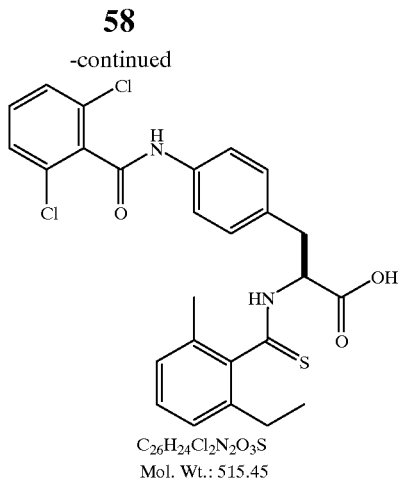

Using the procedure described in example 18, 4-[[(2,6-dichlorophenyl)carbonyl]amino]-N-[(2-ethyl-6-methylphenyl)thioxomethyl]-L-phenylalanine was prepared in 77% yield as an amorphous colorless solid. HR MS: Obs. mass, 515.0942. Calcd. mass, 515.0963 (M+H).

Example 26. N-[(2-ethyl-6-methylphenyl)thioxomethyl]-4-[[(2R)-2-(Fmoc-amino)-1-oxo-3-(pyridin-3-yl)propyl]amino]-L-phenylalanine methyl ester.

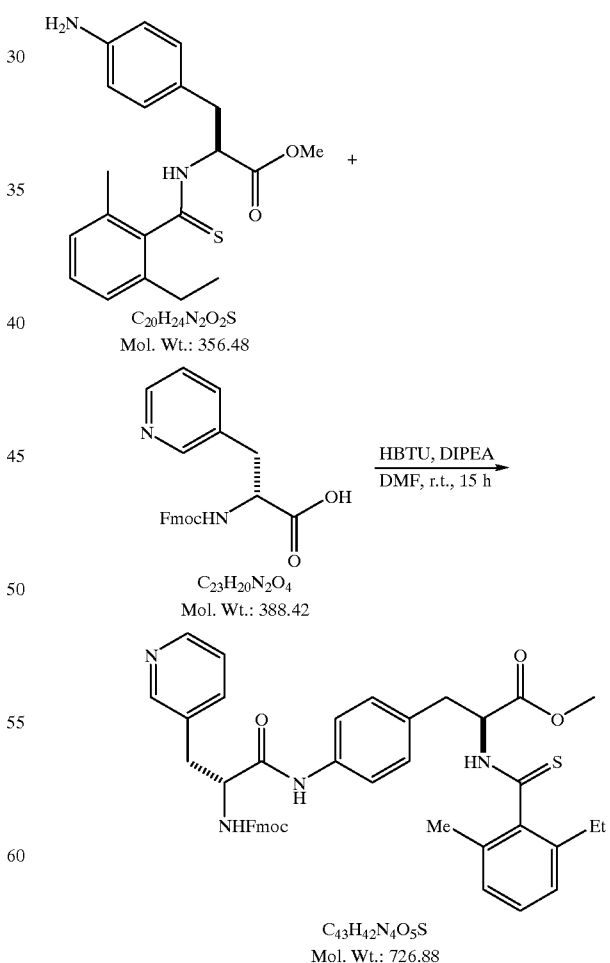

Using the procedure described in example 1, N-[(2-ethyl-6-methylphenyl)thioxomethyl]-4-[[(2R)-2-(Fmoc-amino)-1- oxo-3-(pyridin-3-yl)propyl]amino]-L-phenylalanine methyl ester was prepared in 72% yield as an amorphous colorless solid. HR MS: Obs. mass, 727.2973. Calcd. mass, 727.2954 (M+H).

Example 27. 4-[[(2R)-2-amino-1-oxo-3-(pyridin-3-yl)propyl]amino]-N-[(2-ethyl-6-methylphenyl)thioxomethyl]-L-phenylalanine methyl ester.

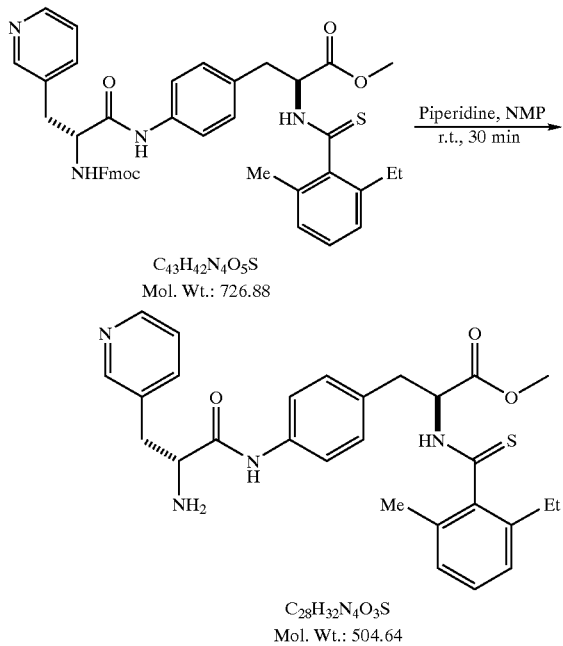

N-[(2-ethyl-6-methylphenyl)thioxomethyl]-4-[[(2R)-2-(Fmoc-amino)-1-oxo-3-(pyridin-3-yl)propyl]amino]-L-phenylalanine methyl ester from example 26 (0.308 mmol, 224 mg) was treated with 25% piperidine in NMP (3 mL) and the solution was stirred at room temperature. Within 1 h, TLC analysis of the mixture indicated the absence of starting material. The mixture was diluted with hexane (25 mL) and the formed layers were separated. The bottom yellow layer was washed with hexane, then was diluted with water and extracted with ethyl acetate and THF (2:1, 3×25 mL). The combined extracts were washed with water (50 mL), brine (50 mL), dried (MgSO₄), filtered and the solvents were removed under vacuum. The resulting residue was dried under high vacuum to afford 126 mg (81%) of 4-[[(2R)-2-amino-1-oxo-3-(pyridin-3-yl)propyl]amino]-N-[(2-ethyl-6-methylphenyl)thioxomethyl]-L-phenylalanine methyl ester as an amorphous colorless solid. HR MS: Obs. mass, 505.2270. Calcd. mass, 505.2274 (M+H).

Example 28. 4-[(2S,4R)-3-acetyl-5-oxo-2-phenyl-4-[(pyridin-3-yl)methyl]imidazolidin-1-yl]-N-[(2-ethyl-6-methylphenyl)thioxomethyl]-L-phenylalanine methyl ester.

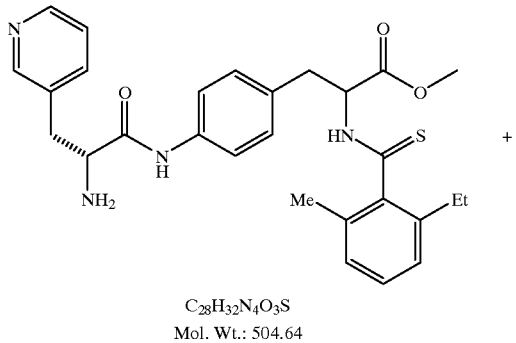

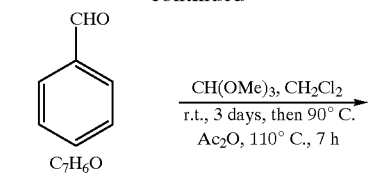

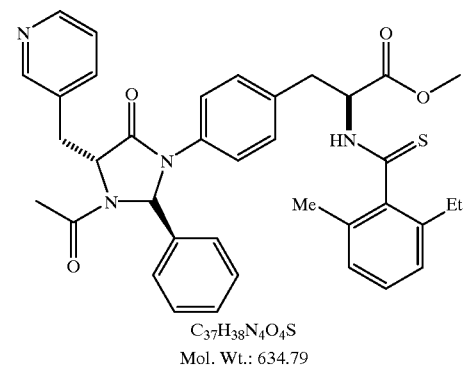

To a solution of 4-[[(2R)-2-amino-1-oxo-3-(pyridin-3-yl)propyl]amino]-N-[(2-ethyl-6-methylphenyl)thioxomethyl]-L-phenylalanine methyl ester (0.224 mmol, 113 mg) in dichloromethane (0.75 mL) and trimethyl orthoformate (0.75 mL), was added benzaldehyde (0.25 mmol, 27.5 mg). After the resulting light yellow solution was stirred for 3 days at room temperature, it was heated to 90° C. (oil bath temperature) and excess acetic anhydride (2.0 mmol, 0.21 mL) was introduced via a syringe. The solution was stirred at 110–120° C. (oil bath temperature) for 6 h, then was cooled to room temperature and the solvents were removed in vacuo. The crude residue was purified by RP-HPLC to obtain 95 mg (67%) of 4-[(2S,4R)-3-acetyl-5-oxo-2-phenyl-4-[(pyridin-3-yl)methyl]imidazolidin-1-yl]-N-[(2-ethyl-6-methylphenyl)thioxomethyl]-L-phenylalanine methyl ester as an amorphous colorless solid. HR MS: Obs. mass, 635.2672. Calcd. mass, 635.2692 (M+H). Another isomer was formed in very minor amount by HPLC (<5%) and not attempted to isolate it.

Example 29. 4-[(2S,4R)-3-acetyl-5-oxo-2-phenyl-4-[(pyridin-3-yl)methyl]imidazolidin-1-yl]-N-[(2-ethyl-6-methylphenyl)thioxomethyl]-L-phenylalanine.

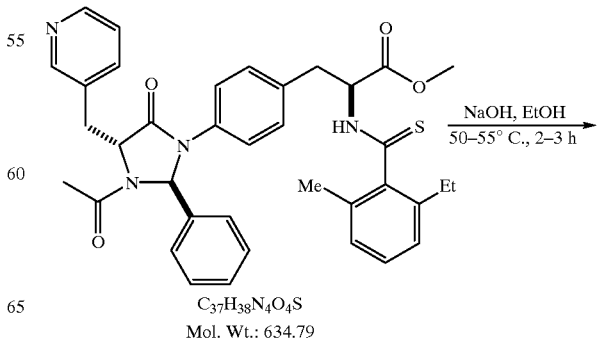

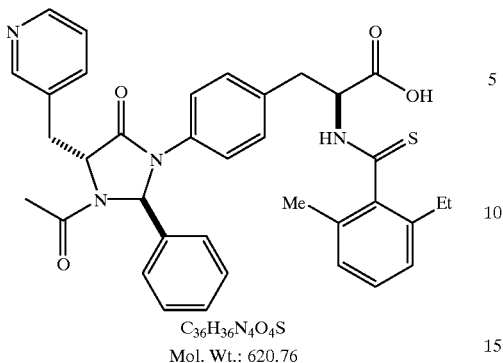

C₃₆H₃₆N₄O₄S
Mol. Wt.: 620.76

The hydrolysis of 4-[(2S,4R)-3-acetyl-5-oxo-2-phenyl-4-[(pyridin-3-yl)methyl]imidazolidin-1-yl]-N-[(2-ethyl-6-methylphenyl)thioxomethyl]-L-phenylalanine methyl ester was carried out using the general procedure described in example 18. The obtained crude product was purified by RP-HPLC, using a 5–95% acetonitrile-water gradient over 30 min and the appropriate fraction was collected. The acetonitrile was removed under vacuum and the product was extracted into ethyl acetate: THF (3:1) (2×25 mL). The combined extracts were washed with brine, dried (MgSO₄), filtered and the solvents were removed under reduced pressure. The resulting residue was dried under high vacuum to obtain 4-[(2S,4R)-3-acetyl-5-oxo-2-phenyl-4-[(pyridin-3-yl)methyl]imidazolinidin-1-yl]-N-[(2-ethyl-6-methylphenyl)thioxomethyl]-L-phenylalanine in 30% yield as an amorphous colorless solid. HR MS: Obs. mass, 621.2520. Calcd. mass, 621.2535 (M+H).

Example 30. N-[(2-fluorophenyl)carbonyl]-4-nitro-L-phenylalanine methyl ester.

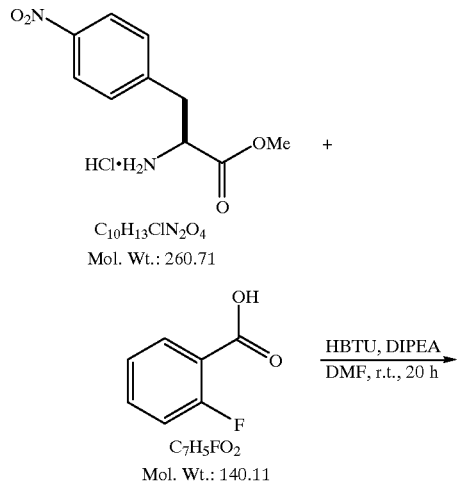

Using the general procedure described in example 14, starting with 4-nitro-L-phenylalanine methyl ester hydrochloride salt and 2-fluorobenzoic acid, N-[(2-fluorophenyl)carbonyl]-4-nitro-L-phenylalanine methyl ester was prepared in 99% yield as a colorless solid, mp 137–139° C. HR MS: Obs. mass, 346.0977. Calcd. mass, 346.0980, M+.

Example 31. N-[(2-fluorophenyl)thioxomethyl]-4-nitro-L-phenylalanine methyl ester.

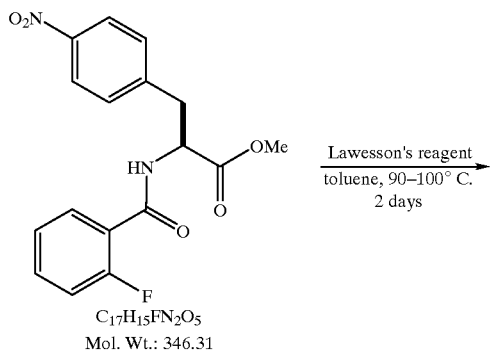

Using the general procedure described in example 15, starting with N-[(2-fluorophenyl)carbonyl]-4-nitro-L-phenylalanine methyl ester, N-[(2-fluorophenyl)thioxomethyl]-4-nitro-L-phenylalanine methyl ester was prepared in 99% yield as an amorphous colorless solid. HR MS: Obs. mass, 363.0816. Calcd. mass, 363.0815 (M+H).

Example 32. 4-amino-N-[(2-fluorophenyl)thioxomethyl]-L-phenylalanine methyl ester.

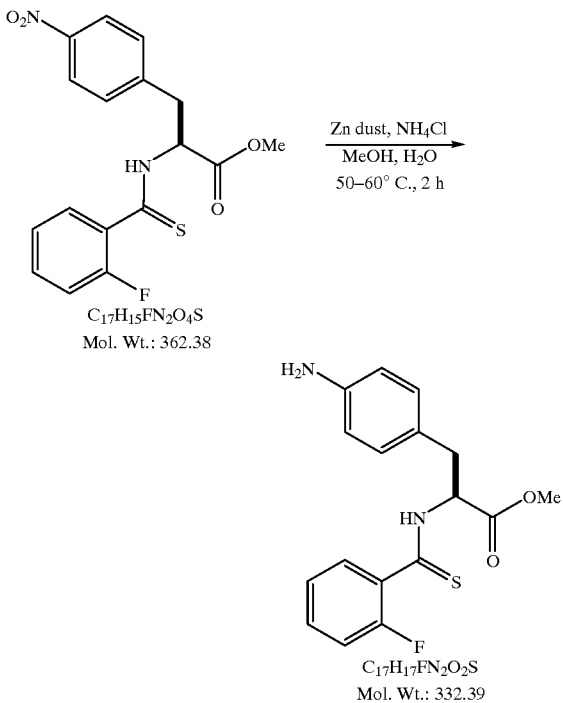

Using the general procedure described in example 16, starting with N-[(2-fluorophenyl)thioxomethyl]-4-nitro-L-phenylalanine methyl ester, 4-amino-N-[(2-fluorophenyl)thioxomethyl]-L-phenylalanine methyl ester was prepared in 87% yield as an amorphous colorless solid. HR MS: Obs. mass, 332.1042. Calcd. mass, 332.1046, (M+H).

Example 33. 4-[[(2,6-dichlorophenyl)carbonyl]amino]-N-[(2-fluorophenyl)thioxomethyl]-L-phenylalanine methyl ester.

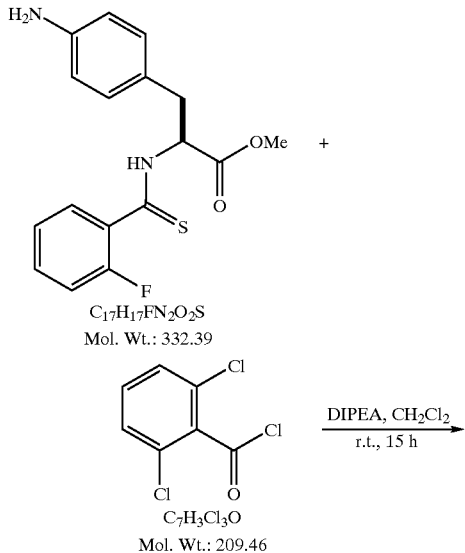

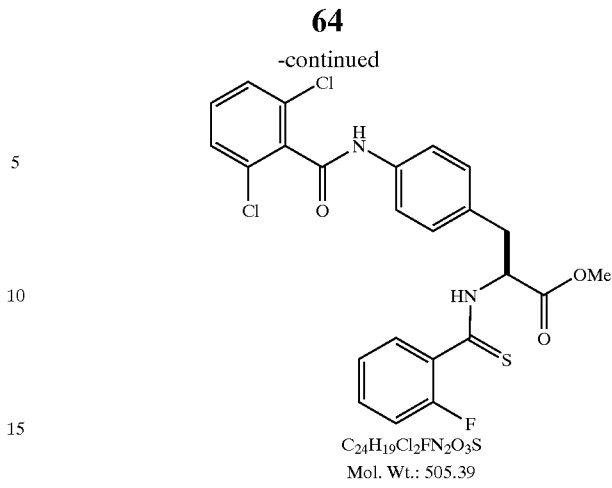

Using the general procedure described in example 17, starting with 4-amino-N-[(2-fluorophenyl)thioxomethyl]-L-phenylalanine methyl ester and 2,6-dichlorobenzoyl chloride, 4-[[(2,6-dichlorophenyl)carbonyl]amino]-N-[(2-fluorophenyl)thioxomethyl]-L-phenylalanine methyl ester was prepared in 74% yield as an amorphous colorless solid. HR MS: Obs. mass, 505.0561. Calcd. mass, 505.0555, (M+H).

Example 34. 4-[[(2,6-dichlorophenyl)carbonyl]amino]-N-[(2-fluorophenyl)thioxomethyl]-L-phenylalanine.

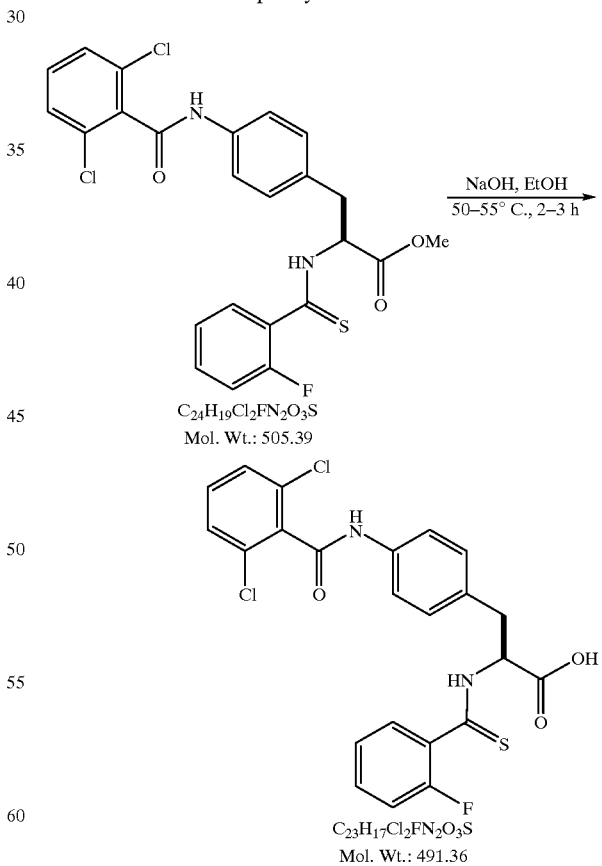

Using the general procedure described in example 18, starting with 4-[[(2,6-dichlorophenyl)carbonyl]amino]-N-[(2-fluorophenyl)thioxomethyl]-L-phenylalanine methyl ester, 4-[[(2,6-dichlorophenyl)carbonyl]amino]-N-[(2- fluorophenyl)thioxomethyl]-L-phenylalanine was prepared in 89% yield as an amorphous colorless solid. HR MS: Obs. mass, 491.0407. Calcd. mass, 491.0399 (M+H).

Example 35. 4-nitro-N-[[(2-(trifluoromethyl)phenyl]carbonyl]-L-phenylalanine methyl ester.

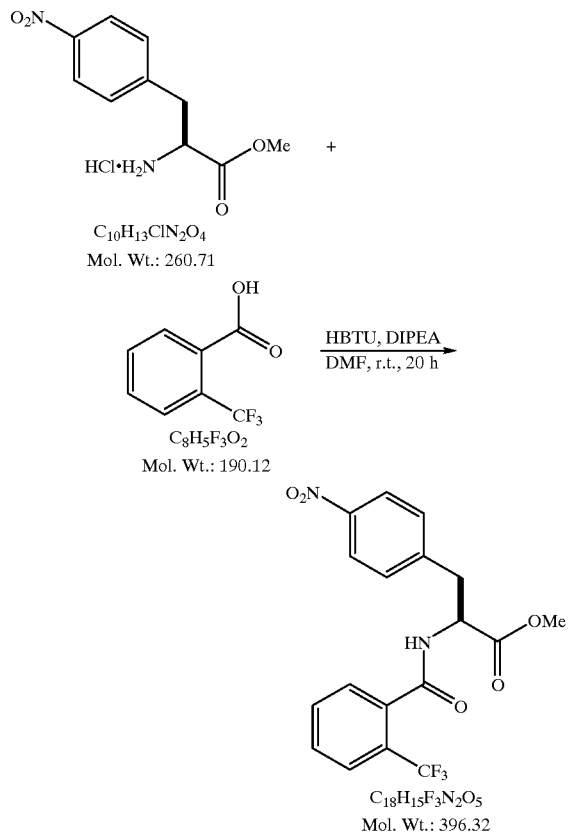

Using the general procedure described in example 14, starting with 4-nitro-L-phenylalanine methyl ester hydrochloride salt and 2-trifluoromethylbenzoic acid, 4-nitro-N-[[(2-(trifluoromethyl)phenyl]carbonyl]-L-phenylalanine methyl ester was prepared in 69% yield as a colorless solid, mp 152–154° C. HR MS: Obs. mass, 397.1017. Calcd. mass, 397.1011 (M+H).

Example 36. 4-nitro-N-[[2-(trifluoromethyl)phenyl]thioxomethyl]-L-phenylalanine methyl ester

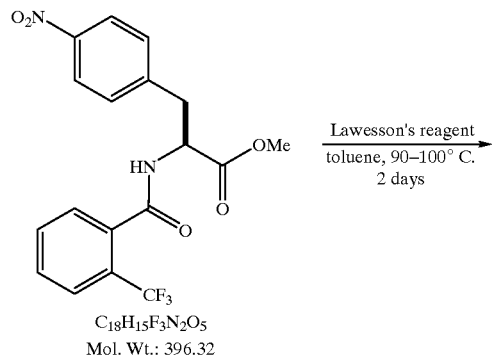

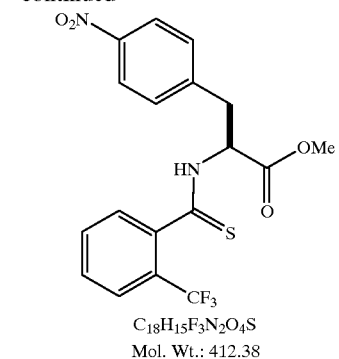

Using the general procedure described in example 15, starting with 4-nitro-N-[[(2-(trifluoromethyl)phenyl]carbonyl]-L-phenylalanine methyl ester, 4-nitro-N-[[2-(trifluoromethyl)phenyl]thioxomethyl]-L-phenylalanine methyl ester was prepared in 67% yield as an amorphous colorless solid. HR MS: Obs. mass, 412.0752. Calcd. mass, 412.0757 (M+H).

Example 37. 4-amnino-N-[[2-(trifluoromethyl)phenyllthioxomethyl]-L-phenylalanine methyl ester.

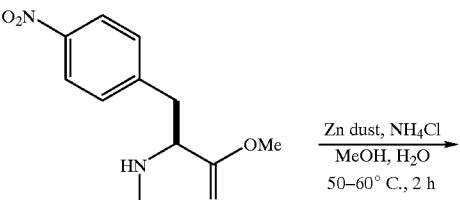

Using the general procedure described in example 16, starting with 4-nitro-N-[[2-(trifluoromethyl)phenyl]thioxomethyl]-L-phenylalanine methyl ester, 4-amino-N-[[2-(trifluoromethyl)phenyl]thioxomethyl]-L-phenylalanine methyl ester was prepared in 98% yield as an amorphous colorless solid. HR MS: Obs. mass, 382.1072. Calcd. mass, 382.1078, (M+H).

Example 38. 4-[[(2,6-dichlorophenyl)carbonyl]amino]-N-[[2-(trifluoromethyl) phenyl]thioxomethyl]-L-phenylalanine methyl ester.

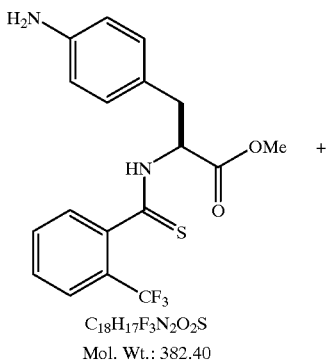

C$_{18}$H$_{17}$F$_{3}$N$_{2}$O$_{2}$S
Mol. Wt.: 382.40

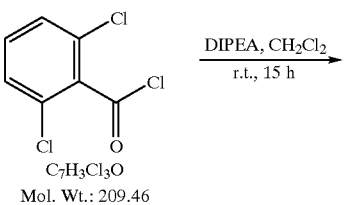

C$_{7}$H$_{3}$Cl$_{3}$O
Mol. Wt.: 209.46

DIPEA, CH$_2$Cl$_2$
r.t., 15 h

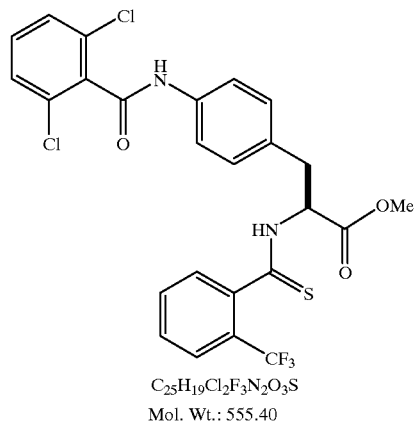

C$_{25}$H$_{19}$Cl$_{2}$F$_{3}$N$_{2}$O$_{3}$S
Mol. Wt.: 555.40

Using the general procedure described in example 17, starting with 4-amino-N-[[2-(trifluoromethyl)phenyl]thioxomethyl]-L-phenylalanine methyl ester and 2,6-dichlorobenzoyl chloride, 4-[[(2,6-dichlorophenyl)carbonyl]amino]-N-[[2-(trifluoromethyl)phenyl]thioxomethyl]-L-phenylalanine methyl ester was prepared in 98% yield as an amorphous colorless solid. HR MS: Obs. mass, 555.0511. Calcd. mass, 555.0524, (M+H).

Example 39. 4-[[(2,6-dichlorophenyl)carbonyl]amino]-N-[[2-(trifluoromethyl) phenyl]thioxomethyl]-L-phenylalanine.

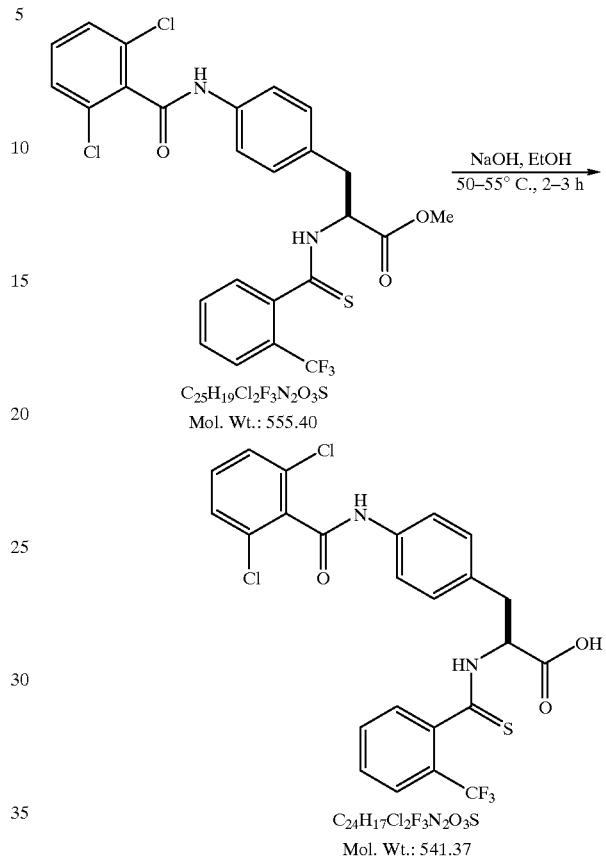

Using the general procedure described in example 18, starting with 4-[[(2,6-dichlorophenyl)carbonyl]amino]-N-[[2-(trifluoromethyl) phenyl]thioxomethyl]-L-phenylalanine methyl ester, 4-[[(2,6-dichlorophenyl)carbonyl]amino]-N-[[2-(trifluoromethyl)phenyl]thioxomethyl]-L-phenylalanine was prepared in 99% yield as an amorphous colorless solid. HR MS: Obs. mass, 541.0358. Calcd. mass, 541.0367, (M+H).

Example 40. 1-(4-bromobutyl)cyclopentanecarboxylic acid methyl ester.

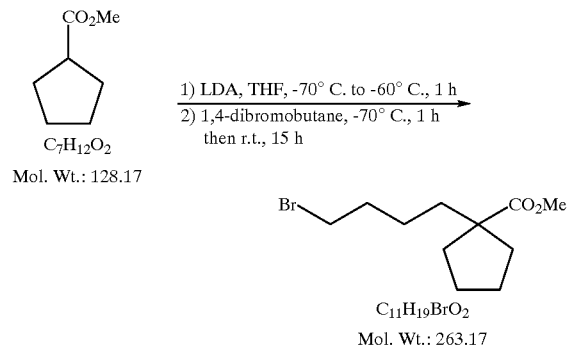

To a solution of diisopropylamine (150 mmol, 21 mL) in THF (100 mL) at −10° C. was added dropwise a 2.5M solution of n-butyl lithium in hexanes (145 mmol, 58 mL) while maintaining the temperature below 0° C. After the addition was complete, the solution was stirred for 30 min at 0° C., then it was cooled to −70° C. using a dry ice/acetone bath. A solution of methyl cyclopentanecarboxylate (100 mmol, 13.1 g) in THF (20 mL) was added dropwise at −70° C. maintaining the reaction temperature between −60 to −70° C. The mixture was then stirred for 1 h at −50 to −60° C. and a solution of 1,4-dibromobutane (100 mmol, 21.59 g) in THF (20 mL) was added dropwise and the light brown suspension was stirred for 1 h at −60 to −70° C. The cooling bath was removed and the reaction was allowed to equilibrate to room temperature and stirred overnight. The reaction mixture then was poured into a saturated solution of ammonium chloride (200 mL) and the mixture was extracted with diethyl ether (2×100 mL). The combined extracts were washed with brine (150 mL), dried (MgSO$_4$), filtered and the solution was concentrated under reduced pressure. The resulting residue was distilled at 120–133° C./2.5 mm Hg to obtain 12.8 g (48%) of 1-(4-bromobutyl)cyclopentanecarboxylic acid methyl ester as a colorless oil. HR MS: Obs. mass, 262.0565. Calcd. mass, 262.0568, (M+).

Example 41. 1-[4-(methylthio)butyl] cyclopentanecarboxylic acid methyl ester.

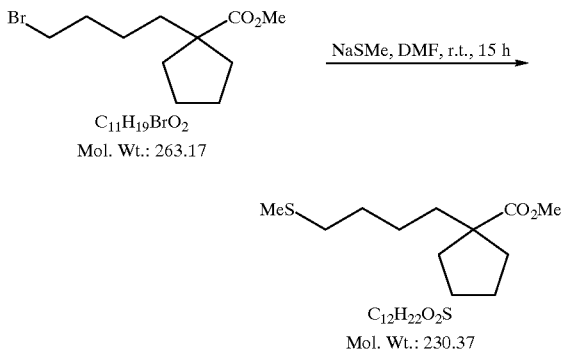

To a solution of 1-(4-bromobutyl)cyclopentanecarboxylic acid methyl ester (38 mmol, 10 g) in DMF (100 mL) was added sodium thiomethoxide (72.6 mmol, 5.09 g). After the addition, an exothermic reaction ensued and the mixture turned to a light brown cloudy solution. The mixture was stirred for 15 h at room temperature, then was poured into water (200 mL) and extracted with diethyl ether (2×150 mL). The combined extracts were washed with brine (150 mL), dried (MgSO$_4$), filtered and the solution was concentrated in vacuo. The residual material was purified by silica gel column chromatography to afford 4.43 g (51 %) of methyl 1-[4-(methylthio)butyl]cyclopentanecarboxylic acid methyl ester as a colorless oil. HR MS: Obs. mass, 230.1343. Calcd. mass, 230.1341, (M+).

Example 42. 1-[4-(methylsulfonyl)butyl] cyclopentanecarboxylic acid methyl ester.

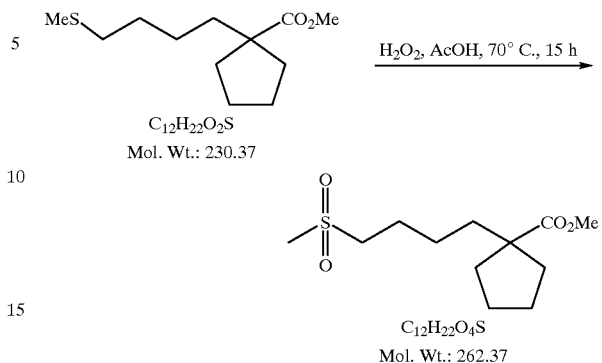

To a solution of 1-[4-(methylthio)butyl] cyclopentanecarboxylic acid methyl ester (19.2 mmol, 4.43 g) in acetic acid (20 mL) was added 30% hydrogen peroxide (10 mL) and stirred mixture was heated to 70° C. for 15 h. TLC analysis of the mixture indicated the absence of starting material. The reaction mixture was cooled to room temperature and was concentrated under vacuum. The residue was poured into saturated sodium bicarbonate solution and was extracted with diethyl ether (3×100 mL). The combined extracts were washed with brine (200 mL), dried (MgSO$_4$), filtered and the solvent was removed under reduced pressure. The residual material was purified by silica gel column chromatography to afford 4.94 g (98%) of 1-[4-(methylsulfonyl)butyl]cyclopentanecarboxylic acid methyl ester as a colorless oil. LR MS (C12H22O4S): 263 (M+H).

Example 43. 1-[4-(methylsulfonyl)butyl] cyclopentane carboxylic acid

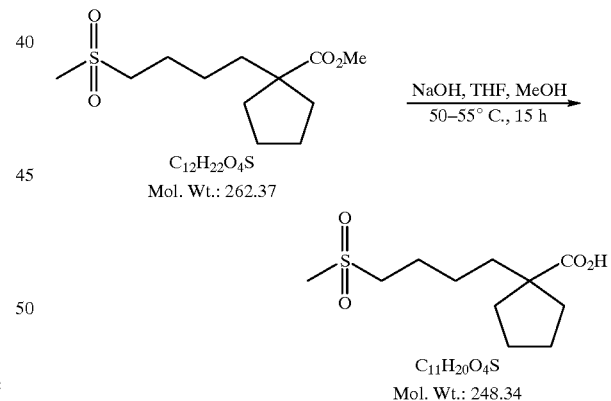

To a solution of 1-[4-(methylsulfonyl)butyl] cyclopentanecarboxylic acid methyl ester (18.8 mmol, 4.94 g) in a mixture of THF (38 mL) and methanol (38 mL) was added 1 N sodium hydroxide (38 mL) and the mixture was heated to 50–55° C. After 15 h, TLC analysis of the reaction mixture indicated the absence of starting material and the mixture was allowed to cool to room temperature. The solvent was removed under vacuum and the residue was diluted with water (100 mL) and extracted with diethyl ether (2×50 mL) to remove any neutral impurities. Then, the basic aqueous layer was acidified with 1 N hydrochloric acid and the product was extracted with ethyl acetate (2×75 mL). The combined extracts were washed with brine, dried (MgSO$_4$), filtered and the solution was concentrated in vacuo. The residual material was dried under high vacuum to afford 4.31 g (92%) of 1-[4-(methylsulfonyl)butyl]cyclopentane carboxylic acid as a low melting colorless solid. LR MS (C11H20O4S): 249 (M+H).

Example 44. 1-[4-(methylthio)butyl]cyclopentanecarboxylic acid.

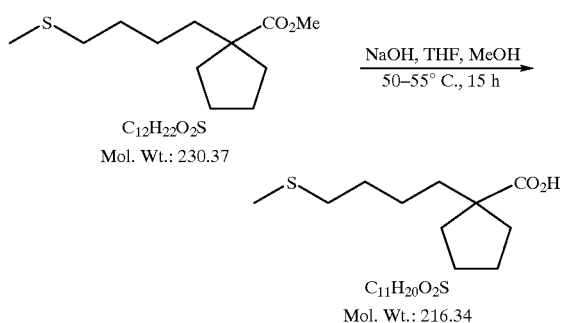

To a solution of 1-[4-(methylthio)butyl]cyclopentanecarboxylic acid methyl ester (18.8 mmol, 4.94 g) in a mixture of THF (38 mL) and methanol (38 mL) was added 1 N sodium hydroxide (38 mL)and the mixture was heated to 50–55° C. for 15 h. TLC analysis of the reaction mixture did not detect the presence of starting ester and the reaction was cooled to room temperature,. The volatiles were removed under reduced pressure and the residue was diluted with water (100 mL) and was extracted with diethyl ether (2×50 mL) to remove any neutral impurities. Then the separated aqueous layer was acidified with 1 N hydrochloric acid and the mixture was extracted with ethyl acetate (2×75 mL). The combined ethyl acetate extracts were washed with brine, dried (MgSO$_4$), filtered, then concentrated in vacuo and the residue was dried under high vacuum to afford 4.31 g (92%) of 1-[4-(methylthio)butyl]cyclopentanecarboxylic acid as a low melting colorless solid. HR MS: Obs. mass, 216.1181. Calcd. mass, 216.1184, M+.

Example 45. N-[[1-[4-(methylthio)butyl]cyclopentyl]carbonyl]-4-nitro-L-phenylalanine methyl ester.

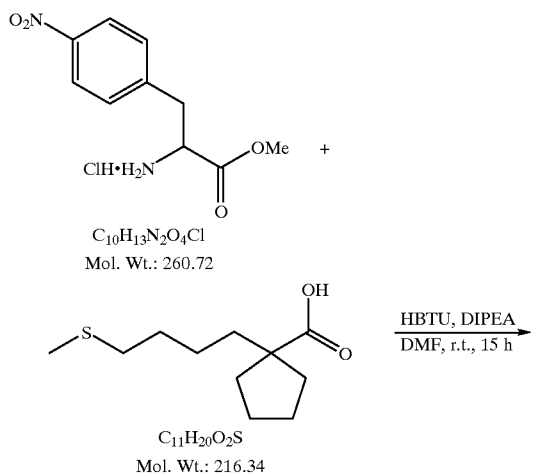

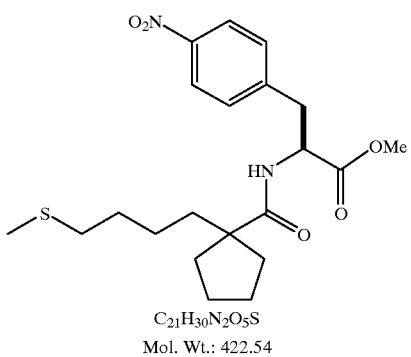

To a suspension of 4-nitro-L-phenylalanine methyl ester hydrochloride salt (181.84 mmol, 47.41 g), 1-[4-(methylthio)butyl]cyclopentanecarboxylic acid (177.17 mmol, 38.33 g) in DMF (470 mL) were added HBTU (177.17 mmol, 67.2 g) and diisopropylethylamine (443 mmol, 77 mL) at room temperature. The clear solution was stirred for 15 h at room temperature at which time TLC analysis of the mixture indicated the absence of starting materials. The reaction mixture was diluted with 600 mL of ethyl acetate then was washed in turn with 0.5N hydrochloric acid (2×250 mL), saturated sodium bicarbonate solution (2×250 mL) and brine (300 mL). The dried (MgSO$_4$) organic layer was filtered and evaporated to dryness under reduced pressure. The crude product which was purified by silica gel column chromatography to afford 58.5 g (78%) of N-[[1-[4-(methylthio)butyl]cyclopentyl]carbonyl]-4-nitro-L-phenylalanine methyl ester as an amorphous colorless solid. HRMS: Obs. mass, 423.1940. Calcd. mass, 423.1953 (M+H).

Example 46. 4-nitro-N-[[1-[4-(methylsulfonyl)butyl]cyclopentyl]carbonyl]-L-phenylalanine methyl ester.

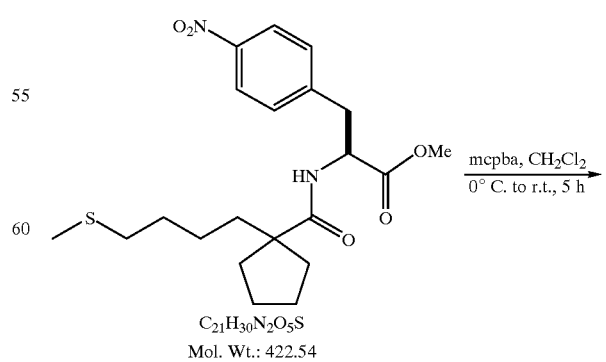

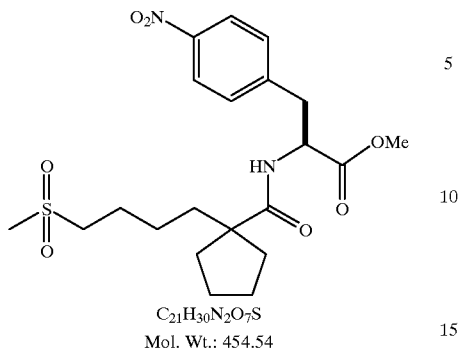

C₂₁H₃₀N₂O₇S
Mol. Wt.: 454.54

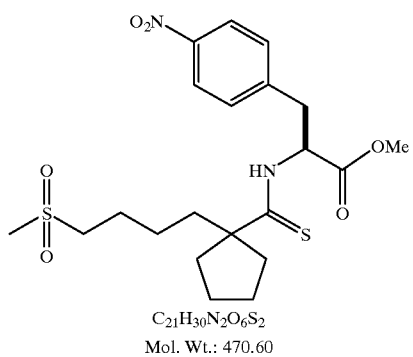

C₂₁H₃₀N₂O₆S₂
Mol. Wt.: 470.60

To a solution of N-[[1-[4-(methylthio)butyl]cyclopentyl]carbonyl]-4-nitro-L-phenylalanine methyl ester (138.4 mmol, 58.5 g) in dichloromethane (1.2 L) was added m-chloroperbenzoic acid (415 mmol, 71.7 g) at −5° C. (ice-salt bath). The suspension was stirred for 30 min at 0° C. and allowed to warm to room temperature. After 5 h, analysis of the reaction by TLC indicated that the starting material was gone. The precipitated solid was removed by filtration and the filtrate was concentrated under vacuum to afford a colorless residue. The residue was dissolved in ethyl acetate (600 mL) and was washed with saturated sodium bicarbonate solution (3×300 mL). TLC analysis showed the presence of m-chloroperbenzoic acid. Accordingly, the ethyl acetate layer was washed in turn with saturated sodium bisulfite solution (20 g in 150 mL of water), saturated sodium bicarbonate solution (200 mL) and brine (300 mL). The dried (MgSO₄) ethyl acetate layer was filtered and evaporated to dryness to give a crude product which was dissolved in ethyl acetate. Diethyl ether and hexane were added to precipitate an oily residue. Some of the solvent was removed under reduced pressure to obtain a white suspension. The suspension was further diluted with diethyl ether and the resulting solid was collected by filtration and was washed with hexane. The colorless low melting solid was dried to furnish 53.9 g (86%) of N-[[1-[4-(methylsulfonyl)butyl]cyclopentyl]carbonyl]-4-nitro-L-phenylalanine methyl ester, mp 40–44° C. HRMS: Obs. mass, 455.1854. Calcd. mass, 455.1852 (M+H).

To a solution of N-[[1-[4-(methylsulfonyl)butyl]cyclopentyl]carbonyl]-4-nitro-L-phenylalanine methyl ester (33 mmol, 15 g) in toluene (100 mL, stored over 4 Å molecular sieves) and freshly distilled THF (50 mL) was added Lawesson's reagent (33 mmol, 13.35 g, 1.0 equiv.) at room temperature. The solution was heated to 60–65° C. and was stirred for 48 h at which time TLC analysis of the mixture indicated the absence of starting material. The reaction mixture was cooled to room temperature and was poured into saturated sodium bicarbonate solution (200 mL) and extracted with ethyl acetate (3×150 mL). An oil formed in the aqueous layer, which was separated, diluted with water and extracted with ethyl acetate (2×50 mL). The combined ethyl acetate extracts were washed with saturated sodium bicarbonate solution (200 mL), with brine (300 mL), dried (MgSO₄), filtered and the solution was concentrated in vacuo. The residual light brown syrup was purified by silica gel column chromatography (hexane:ethyl acetate, 1:1) to obtain 6.87 g (44%) of N-[[1-[4-(methylsulfonyl)butyl]cyclopentyl]thioxo-methyl]-4-nitro-L-phenylalanine methyl ester as a fluffy yellow solid. HRMS: Obs. mass, 493.1438. Calcd. mass, 493.1443 (M+Na).

Example 47. N-[[1-[4-(methylsulfonyl)butyl]cyclopentyl]thioxomethyl]-4-nitro-L-phenylalanine methyl ester.

Example 48. 4-amino-N-[[1-[4-(methylsulfonyl)butyl]cyclopentyl]thioxomethyl)-L-phenylalanine methyl ester.

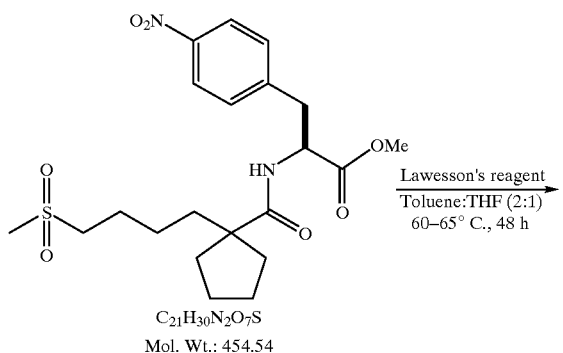

C₂₁H₃₀N₂O₇S
Mol. Wt.: 454.54

Lawesson's reagent
Toluene:THF (2:1)
60–65° C., 48 h

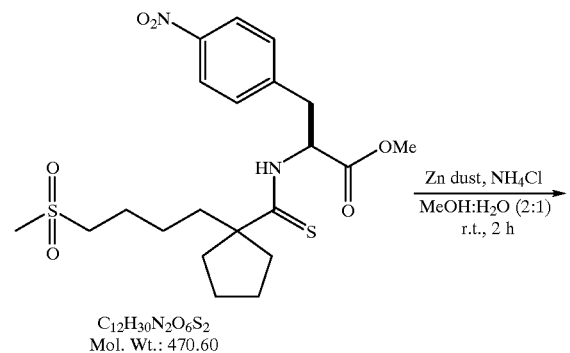

C₁₂H₃₀N₂O₆S₂
Mol. Wt.: 470.60

Zn dust, NH₄Cl
MeOH:H₂O (2:1)
r.t., 2 h

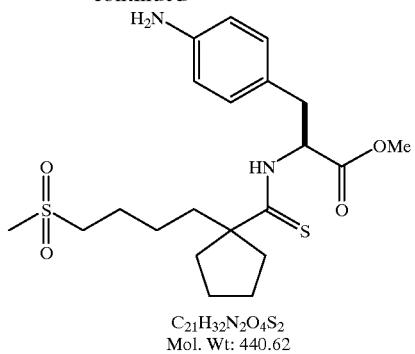

C21H32N2O4S2
Mol. Wt: 440.62

The poorly soluble N-[[1-[4-(methylsulfonyl)butyl] cyclopentyl]thioxomethyl]-4-nitro-L-phenylalanine methyl ester (19.3 mmol, 9.07 g) was dissolved in methanol (150 mL) and THF (20 mL) by gentle heating with a heat gun. To this solution, zinc dust (~325 mesh, 193 mmol, 12.62 g, 10 equiv.) and ammonium chloride (289.5 mmol, 15.5 g, 15 equiv.) were added followed by water (75 mL) at room temperature. After the addition of water, an exothermic reaction ensued and the temperature rose to 45 to 50° C. The suspension was stirred for 1 h, at which time TLC analysis of the mixture indicated the absence of starting material. The reaction mixture was filtered and the filter cake was washed with methanol (200 mL) and THF (100 mL). The volatiles were removed under vacuum and the organic residue was extracted into ethyl acetate (2×200 mL). The combined extracts were washed brine (250 mL) then were dried (MgSO4), filtered and evaporated to dryness to give 8.37 g (98%) of 4-amino-N-[[1-[4-(methylsulfonyl)butyl] cyclopentyl]thioxomethyl)-L-phenylalanine methyl ester as a colorless gum which was used directly for next step. HRMS: Obs. mass, 441.1884. Calcd. mass, 441.1882 (M+H).

Example 49. 4-[[(2,6-dichlorophenyl)carbonyl] amino]-N-[[1-[4-(methylsulfonyl)-butyl]cyclopentyl] thioxomethyl]-L-phenylalanine methyl ester.

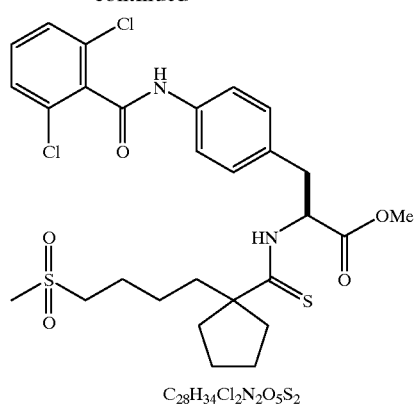

C28H34Cl2N2O5S2
Mol. Wt.: 613.62

To a solution of 4-amino-N-[[1-[4-(methylsulfonyl)butyl] cyclopentyl]thioxomethyl]-L-phenylalanine methyl ester (19.0 mmol, 8.37 g) and 2,6-dichlorobenzoyl chloride (21 mmol, 4.4 g) in dichloromethane (90 mL) was added diisopropylethylamine (32.3 mmol, 5.6 mL) at room temperature. The solution was stirred for 15 h at which time TLC analysis of the mixture indicated the absence of starting material. Then, it was diluted with water (100 mL) and the two layers were separated. The aqueous phase was extracted with dichloromethane (100 mL) and the combined extracts were washed with brine (200 mL). The dried (MgSO4) solution was concentrated under vacuum and the residue was purified by silica gel column chromatography eluting with (hexane:ethyl acetate:dichloromethane, 1:1:1) to obtain 11.54 g (99%) of 4-[[(2,6-dichlorophenyl)carbonyl]amino]-N-[[1-[4-(methylsulfonyl)butyl]cyclopentyl]thioxomethyl]-L-phenylalanine methyl ester as a colorless solid, mp 200–202° C. HRMS: Obs. mass, 613.1367. Calcd. mass, 613.1363 (N+H).

Example 50. 4-[[(2,6-dichlorophenyl)carbonyl] amino]-N-[[1-[4-(methylsulfonyl)butyl]cyclopentyl] thioxomethyl]-L-phenylalanine.

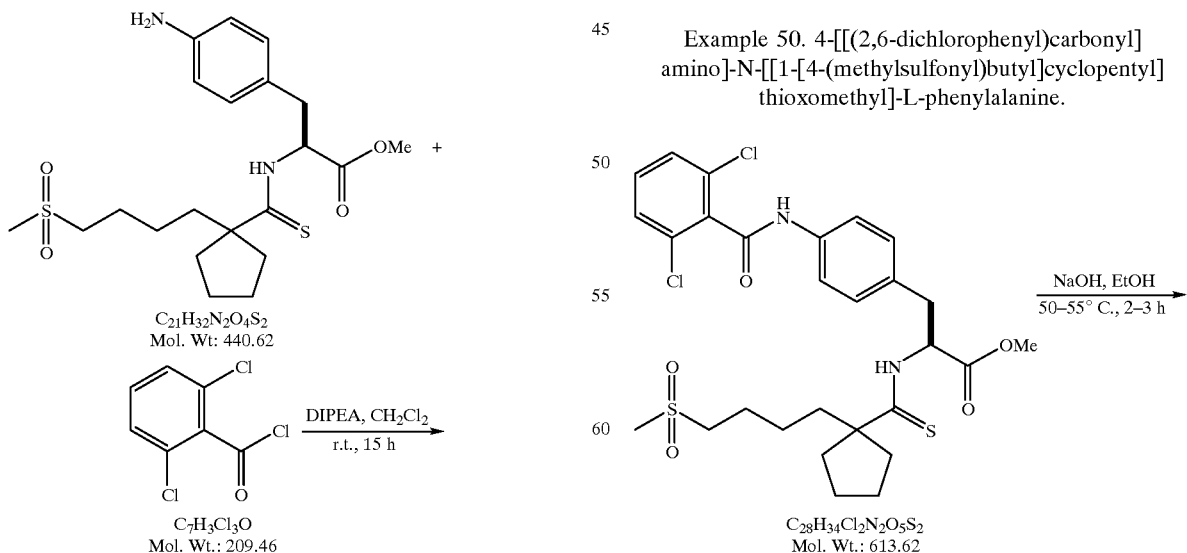

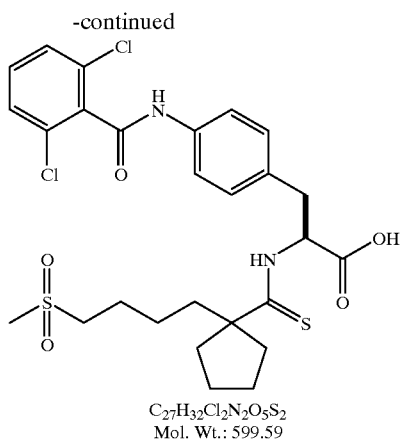

C27H32Cl2N2O5S2
Mol. Wt.: 599.59

To a solution of 4-[[(2,6-dichlorophenyl)carbonyl]amino]-N-[[1-[4-(methylsulfonyl)butyl]cyclopentyl]thioxomethyl]-L-phenylalanine methyl ester (25.86 mmol, 15.87 g) in ethanol (75 mL) was added aqueous 1.0N sodium hydroxide (60 mL) at 50° C . The mixture was heated to 50–55° C. and the resulting clear light brown solution was stirred for 22 h at which time TLC analysis of the mixture indicated the absence of starting material. The mixture was diluted with water and allowed to cool to room temperature and was filtered to remove a small amount of solids. The filtrate was concentrated and the residual aqueous solution was washed with diethyl ether (2×75 mL). The basic aqueous layer was acidified with 3.0N HCl to form a cloudy suspension and was extracted with ethyl acetate (3×100 mL). The combined ethyl acetate extracts were washed with brine (200 mL) then the dried (MgSO$_4$) solution was filtered and evaporated to dryness. The residue was taken up in dichloromethane and diluted with diethyl ether:hexane (1:1) to obtain a solid which was collected by filtration. Trituration of the solid with hot ethyl acetate (~100 mL) resulted in a suspension that was then diluted with diethyl ether (~50 mL) and the solid was collected by filtration. The above Trituration was repeated to afford 10.89 g (70%) of 4-[[(2,6-dichlorophenyl)carbonyl]amino]-N-[[1-[4-(methylsulfonyl)butyl]cyclopentyl]thioxomethyl]-L-phenylalanine as a colorless solid. HR MS: Obs. mass, 599.1193. Calcd. mass, 599.1208 (M+H).

Example 51. 4-[[(2,6-dichlorophenyl)carbonyl]amino]-N-[[1-[4-(methylsulfonyl)-butyl]cyclopentyl]thioxomethyl]-L-phenylalanine sodium salt.

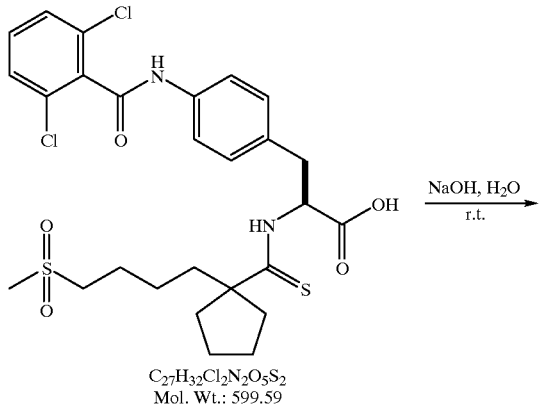

C27H32Cl2N2O5S2
Mol. Wt.: 599.59

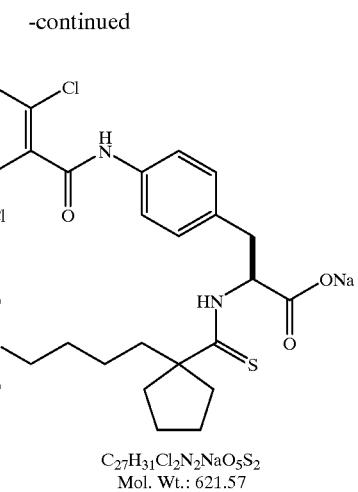

C27H31Cl2N2NaO5S2
Mol. Wt.: 621.57

A suspension of 4-[[(2,6-dichlorophenyl)carbonyl]amino]-N-[[1-[4-(methylsulfonyl)butyl]-cyclopentyl]thioxomethyl]-L-phenylalanine (16.49 mmol, 9.89 g) in water (100 mL) was treated with aqueous 1.0N sodium hydroxide (16.4 mmol, 16.4 mL) at room temperature. The mixture was heated to 40–45° C. and some acetonitrile (~15 mL) was added to give an essentially clear solution containing a small amount of suspended solid. The solution was filtered and the filtrate was lyophilized to afford 10.1 g of sodium salt as a colorless solid. HRMS: Obs. mass, 621.1023. Calcd. mass, 621.1027 (M+H).

Example 52. 4-[[(2,4-dimethylpyridin-3-yl)carbonyl]amino]-N-[[1-[4-(methylsulfonyl)butyl]cyclopentyl]thioxomethyl]-L-phenylalanine methyl ester.

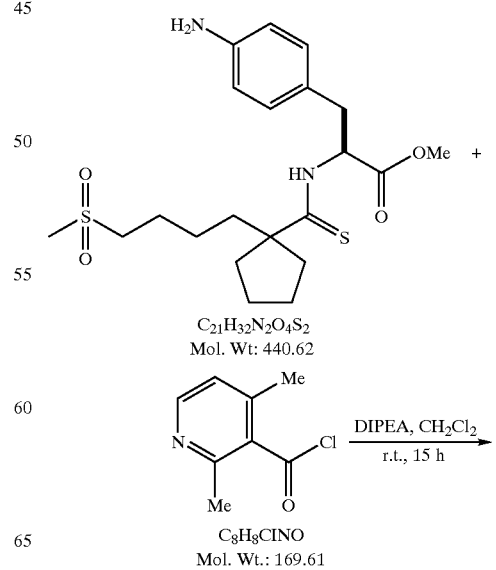

C21H32N2O4S2
Mol. Wt: 440.62

C8H8ClNO
Mol. Wt.: 169.61

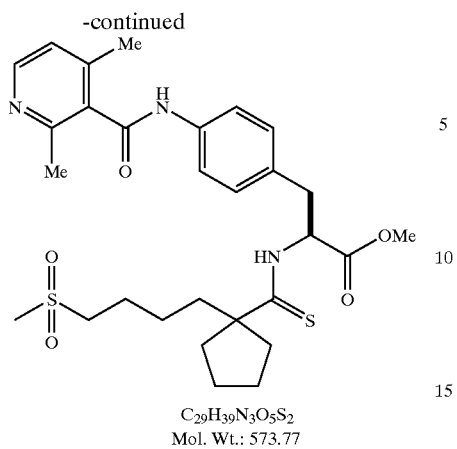

C29H39N3O5S2
Mol. Wt.: 573.77

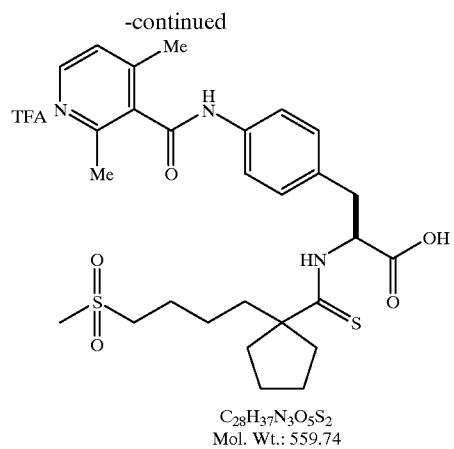

C28H37N3O5S2
Mol. Wt.: 559.74

To an ice cold solution of 2,4-dimethyl-3-pyridinecarboxylic acid (0.3 mmol, 45 mg) in dichloromethane (2 mL) containing one drop of DMF, was added oxalyl chloride (0.39 mmol, 49.5 mg) at 0° C. The reaction mixture was stirred for 30 min at this temperature, was allowed to warm to room temperature and was stirred for an additional 2 h. The solution was concentrated and the residue was dried under high vacuum. To a mixture of above acid chloride and 4-amino-N-[[1-[4-(methylsulfonyl)butyl]cyclopentyl]thioxomethyl]-L-phenylalanine methyl ester (0.2 mmol, 88 mg) in dichloromethane (3 mL) was added diisopropylethylamine (1 mmol, 0.175 mL) at room temperature. After the solution had stirred for 15 h, TLC analysis of the mixture did not detect any starting material remaining. The solution was diluted with water (20 mL) and dichloromethane (20 mL) and the layers were separated. The aqueous phase was extracted with dichloromethane (10 mL) and the combined organic extracts were washed with brine (300 mL). The dried (MgSO4) solution was filtered and evaporated to dryness and the residual material was purified by RP-HPLC to obtain 74 mg (65%) of 4-[[(2,4-dimethylpyridin-3-yl)carbonyl]amino]-N-[[1-[4-(methylsulfonyl)butyl]cyclopentyl]thioxomethyl]-L-phenylalanine methyl ester as an amorphous colorless solid. HRMS: Obs. mass, 574.2389. Calcd. mass, 574.2409 (M+H).

Example 53. 4-[[(2,4-dimethylpyridin-3-yl)carbonyl]amino]-N-[[1-[4-(methylsulfonyl)butyl]-cyclopentyl]thioxomethyl]-L-phenylalanine trifluoroacetic acid salt.

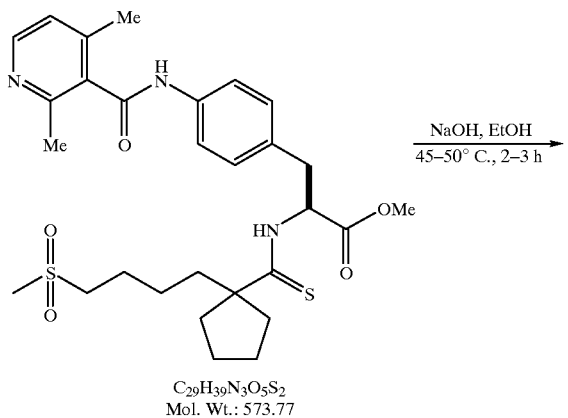

C29H39N3O5S2
Mol. Wt.: 573.77

To a solution of 4-[[(2,4-dimethylpyridin-3-yl)carbonyl]amino]-N-[[1-[4-(methylsulfonyl)butyl]cyclopentyl]thioxomethyl]-L-phenylalanine methyl ester (0.118 mmol, 68 mg) in ethanol (4 mL) was added aqueous 1.0N sodium hydroxide (3 mL) at room temperature and the stirred mixture was heated to 45–50° C. After 3 h TLC analysis of the clear solution indicated that the starting material had been consumed. The mixture was concentrated and the crude residue was purified by RP-HPLC to afford 54.5 mg (82%) of 4-[[(2,4-dimethylpyridin-3-yl)carbonyl]amino]-N-[[1-[4-(methylsulfonyl)butyl]-cyclopentyl]thioxomethyl]-L-phenylalanine trifluoroacetic acid salt as an amorphous colorless solid. HR MS: Obs. mass, 560.2240. Calcd. mass, 560.2253 (M+H).

Example 54. 1-(4-bromobutyl)cyclobutanecarboxylic acid ethyl ester.

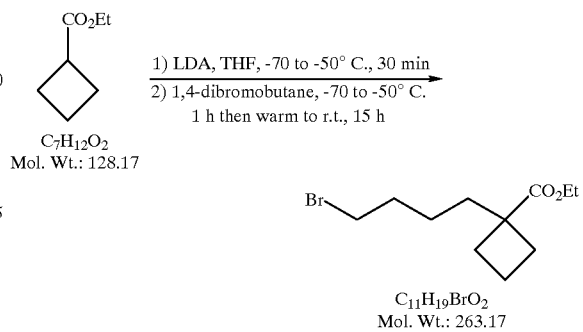

Using the general procedure described in example 40, starting with cyclobutanecarboxylic acid ethyl ester, 1-(4-bromobutyl)cyclobutanecarboxylic acid ethyl ester was prepared in 58% yield as a colorless oil. HR MS: Obs. mass, 263.0563. Calcd. mass, 263.0568, M+.

Example 55. 1-[4-(methylthio)butyl]cyclobutanecarboxylic acid ethyl ester.

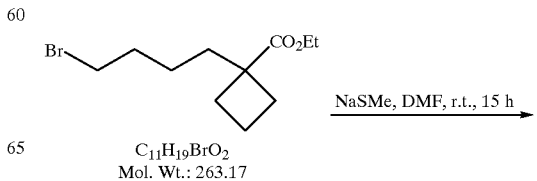

-continued

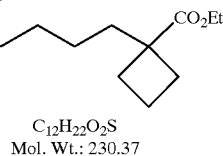

C₁₂H₂₂O₂S
Mol. Wt.: 230.37

Using the general procedure described in example 41, starting with 1-(4-bromobutyl)cyclobutanecarboxylic acid ethyl ester, 1-[4-(methylthio)butyl]cyclobutanecarboxylic acid ethyl ester was prepared in 87% yield as a colorless oil. HR MS: Obs. mass, 230.1339. Calcd. mass, 230.1340, M+.

Example 56. ethyl 1-[4-(methylsulfonyl)butyl] cyclobutane carboxylic acid ethyl ester.

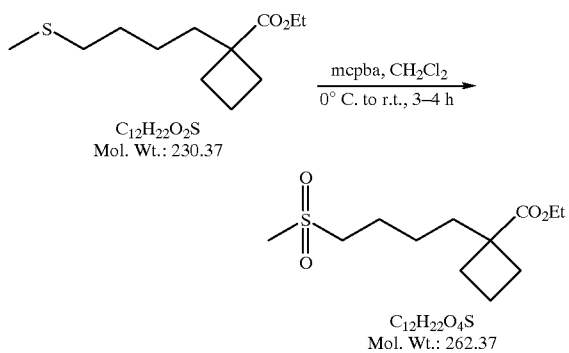

Using the general procedure described in example 46, starting with 1-[4-(methylthio)butyl]cyclobutanecarboxylic acid ethyl ester, 1-[4-(methylsulfonyl)-butyl] cyclobutanecarboxylic acid ethyl ester was prepared in 92% yield as a colorless oil. HR MS: Obs. mass, 262.1231. Calcd. mass, 262.1238, M+.

Example 57. 1-[4-(methylsulfonyl)butyl] cyclobutanecarboxylic acid.

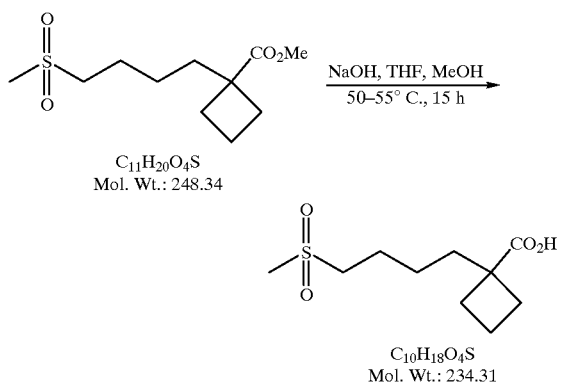

Using the general procedure described in example 43, starting with 1-[4-(methylsulfonyl)butyl]cyclobutanecarboxylic acid ethyl ester, 1-[4-(methylsulfonyl)butyl] cyclobutanecarboxylic acid was prepared in 92% yield as a low melting colorless solid. HR MS: Obs. mass, 234.0921. Calcd. mass, 234.0918, (M+).

Example 58. N-[[1-[4-(methylsulfonyl)butyl] cyclobutyl]carbonyl]-4-nitro-L-phenylalanine methyl ester.

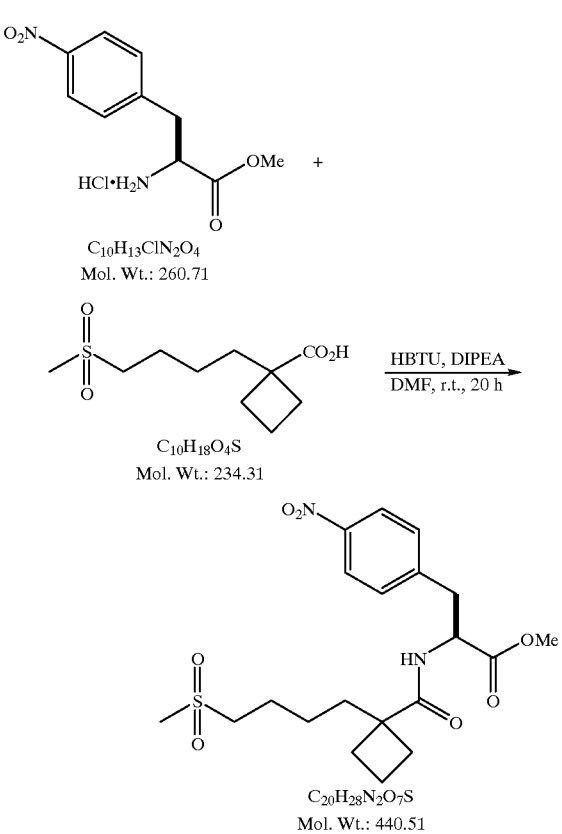

Using the general procedure described in example 45, starting with 1-[4-(methylsulfonyl)butyl]cyclobutanecarboxylic acid and 4-nitro-L-phenylalanine methyl ester hydrochloride salt, N-[[1-[4-(methylsulfonyl)butyl]cyclobutyl]carbonyl]-4-nitro-L-phenylalanine methyl ester was prepared in 89% yield as a yellow gum. HR MS: Obs. mass, 441.1700. Calcd. mass, 441.1696 (M+H).

Example 59. N-[[1-[4-(methylsulfonyl)butyl] cyclobutyl]thioxomethyl)-4-nitro-L-phenylalanine methyl ester.

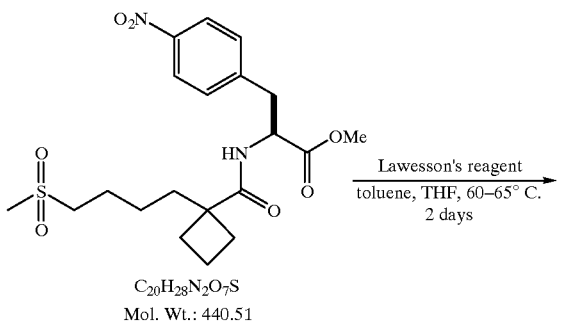

-continued

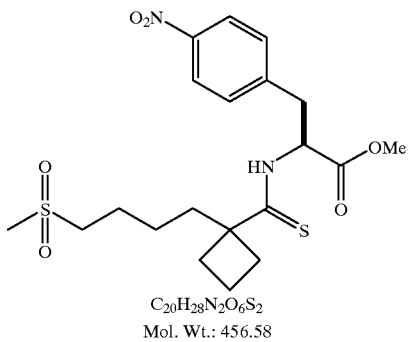

C20H28N2O6S2
Mol. Wt.: 456.58

Using the general procedure described in example 47, starting with 4-nitro-N-[[1-[4-(methylsulfonyl)butyl]cyclobutyl]carbonyl]-L-phenylalanine methyl ester, N-[[1-[4-(methylsulfonyl)butyl]cyclobutyl]thioxomethyl)-4-nitro-L-phenylalanine methyl ester was prepared in 80% yield as a colorless solid, mp 150–152° C. HR MS: Obs. mass, 457.1464. Calcd. mass, 457.1467, (M+H).

Example 60. 4-amino-N-[[1-[4-(methylsulfonyl)butyl]cyclobutyl]thioxomethyl)-L-phenylalanine methyl ester.

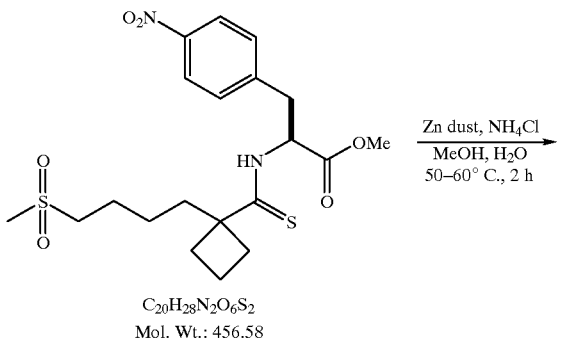

Using the general procedure described in example 48, starting with N-[[1-[4-(methylsulfonyl)butyl]cyclobutyl]thioxomethyl)-4-nitro-L-phenylalanine methyl ester, 4-amino-N-[[1-[4-(methylsulfonyl)butylcyclobutyl]thioxomethyl)-L-phenylalanine methyl ester was prepared in 94% yield as a hygroscopic solid. HR MS: Obs. mass, 427.1720. Calcd. mass, 427.1725, (M+H).

Example 61. 4-[[(2,6-dichlorophenyl)carbonyl]amino]-N-[[1-[4-(methylsulfonyl)butyl]cyclobutyl]thioxomethyl]-L-phenylalanine methyl ester.

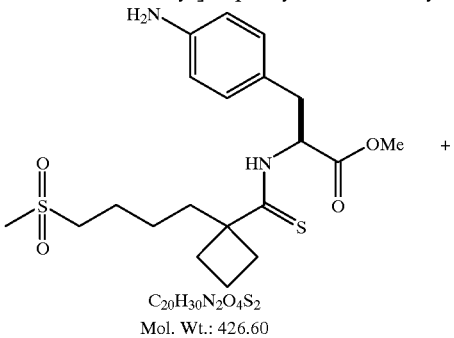

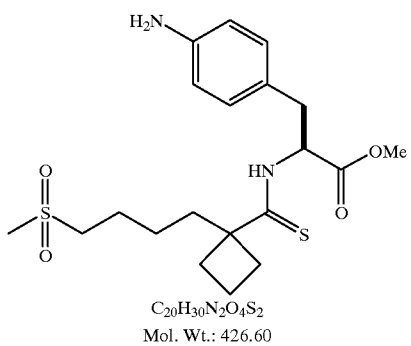

Using the procedure described in example 49, starting with 4-amino-N-[[1-[4-(methylsulfonyl)-butyl]cyclobutyl]thioxomethyl)-L-phenylalanine methyl ester, 4-[[(2,6-dichlorophenyl)-carbonyl]amino]-N-[[1-[4-(methylsulfonyl)butyl]cyclobutyl]thioxomethyl]-L-phenylalanine methyl ester was obtained in 92% yield as an amorphous colorless solid. HR MS: Obs. mass, 599.1207. Calcd. mass, 599.1208 (M+H).

Example 62. 4-[[(2,6-dichlorophenyl)carbonyl]amino]-N-[[1-[4-(methylsulfonyl)-butyl]cyclobutyl]thioxomethyl]-L-phenylalanine.

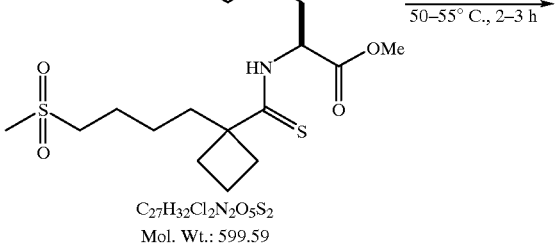

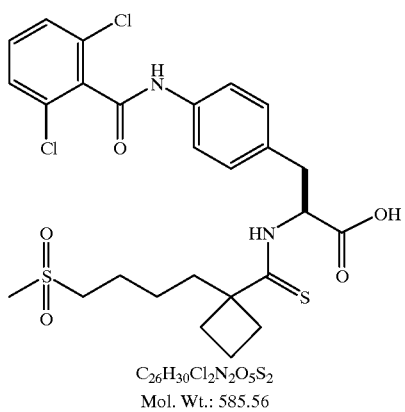

C₂₆H₃₀Cl₂N₂O₅S₂
Mol. Wt.: 585.56

Using the general procedure described in example 50, starting with 4-[[(2,6-dichlorophenyl)carbonyl]amino]-N-[[1-[4-(methylsulfonyl)butyl]cyclobutyl]thioxomethyl]-L-phenylalanine methyl ester, 4-[[(2,6-dichlorophenyl)carbonyl]amino]-N-[[1-[4-(methylsulfonyl)butyl]cyclobutyl]thioxomethyl]-L-phenylalanine was prepared in 99% yield as an amorphous colorless solid. HR MS: Obs. mass, 585.1038. Calcd. mass, 585.1051 (M+H).

Example 63. N-[[1-[4-(methylsulfonyl)butylcyclobutyl]thioxomethyl]-4-[[[4-(tifluoromethyl) pyrimidin-5-yl]carbonyl]amino]-L-phenylalanine methyl ester.

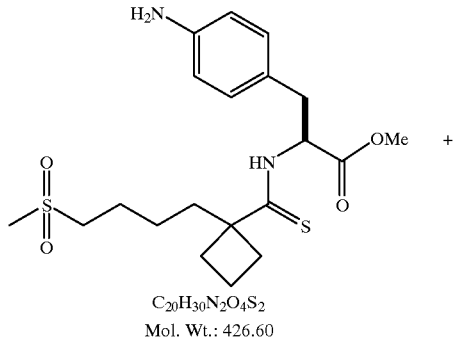

C₂₀H₃₀N₂O₄S₂
Mol. Wt.: 426.60

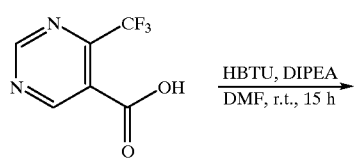

HBTU, DIPEA
DMF, r.t., 15 h

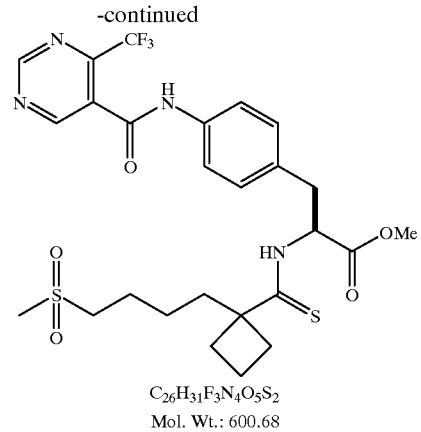

C₂₆H₃₁F₃N₄O₅S₂
Mol. Wt.: 600.68

Using the general procedure described in example 45, starting with 4-(trifluoromethyl)pyrimidine-5-carboxylic acid and 4-amino-N-[[1-[4-(methylsulfonyl)butyl]cyclobutyl]thioxomethyl)-L-phenylalanine methyl ester, N-[[1-[4-(methylsulfonyl)butyl]cyclobutyl]thioxomethyl]-4-[[[2-(trifluoromethyl) pyrimidin-5-yl]carbonyl]amino]-L-phenylalanine methyl ester was prepared in 32% yield as an amorphous colorless solid. HR MS: Obs. mass, 601.1766. Calcd. mass, 601.1766 (M+H).

Example 64. N-[[1-[4-(methylsulfonyl)butyl]cyclobutyl]thioxomethyl]- 4-[[[2-(trifluoromethyl)pyrimidin-5-yl]carbonyl]amino]-L-phenylalanine.

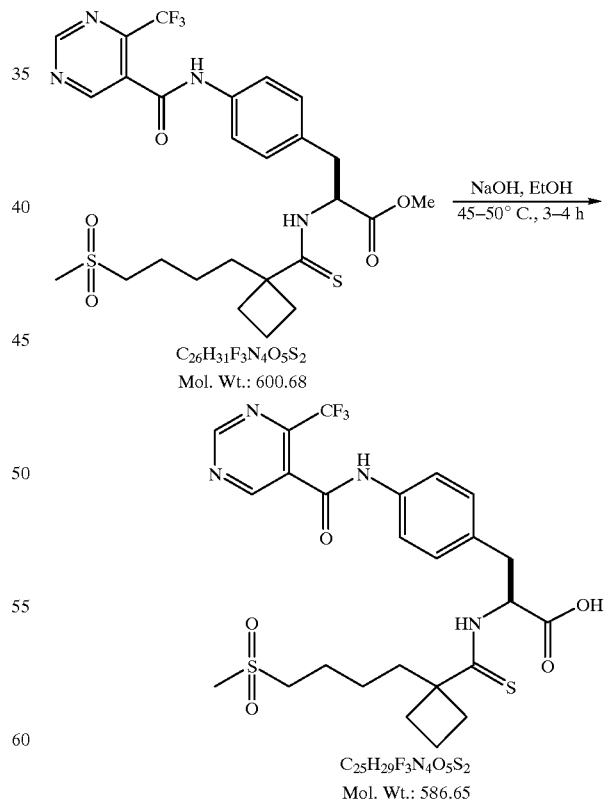

Using the general procedure described in example 50, starting with N-[[1-[4-(methylsulfonyl)butyl]cyclobutyl]thioxomethyl]-4-[[[2-(trifluoromethyl) pyrimidin-5-yl]carbonyl]amino]-L-phenylalanine methyl ester, N-[[1-[4-(methylsulfonyl)butyl]cyclobutyl]thioxomethyl]-4-[[[2-(trifluoromethyl)pyrimidin-5-yl]carbonyl]amino]-L-phenylalanine was prepared in 22% yield as an amorphous colorless solid. HRMS: Obs. mass, 587.1619. Calcd. mass, 587.1609 (M+H).

Example 65. Preparation 1-(3-bromopropyl) cyclobutanecarboxylic acid ethyl ester.

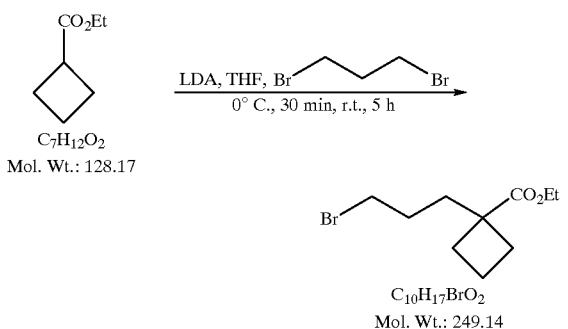

Using the general procedure described in example 40, starting with cyclobutanecarboxylic acid ethyl ester and 1,3-dibromopropane, 1-(3-bromopropyl)cyclobutanecarboxylic acid ethyl ester was prepared in 33% yield as a colorless oil. HR MS: Obs. mass, 248.0416. Calcd. mass, 248.0412 (M+).

Example 66. 1-[3-(methylthio)propyl] cyclobutanecarboxylic acid ethyl ester and 1-[3-(methylthio)propyl]cyclobutanecarboxylic acid.

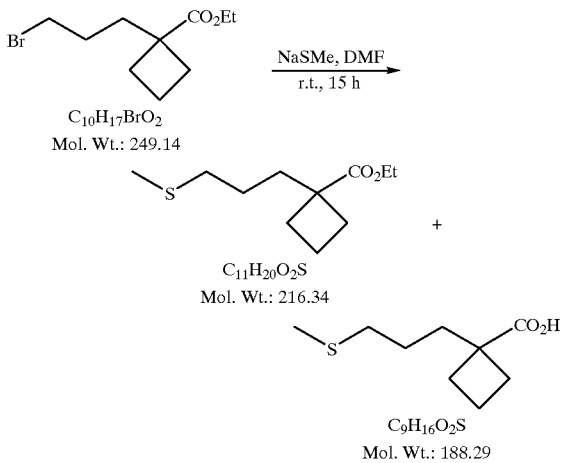

Using the general procedure described in example 41, starting with 1-(3-bromopropyl)cyclobutanecarboxylic acid ethyl ester, 1-[3-(methylthio)propyl]cyclobutanecarboxylic acid ethyl ester was prepared in 58% yield as a colorless oil. HR MS: Obs. mass, 216.1182. Calcd. mass, 216.1184 (M+). Also, 1-[3-(methylthio)propyl]cyclobutanecarboxylic acid was obtained in 16% yield as a colorless oil. HR MS: Obs. mass, 188.0872. Calcd. mass, 188.0871 (M+).

Example 67. N-[[1-[3-(methylthio)propyl]cyclobutyl]carbonyl]-4-nitro-L-phenylalanine methyl ester.

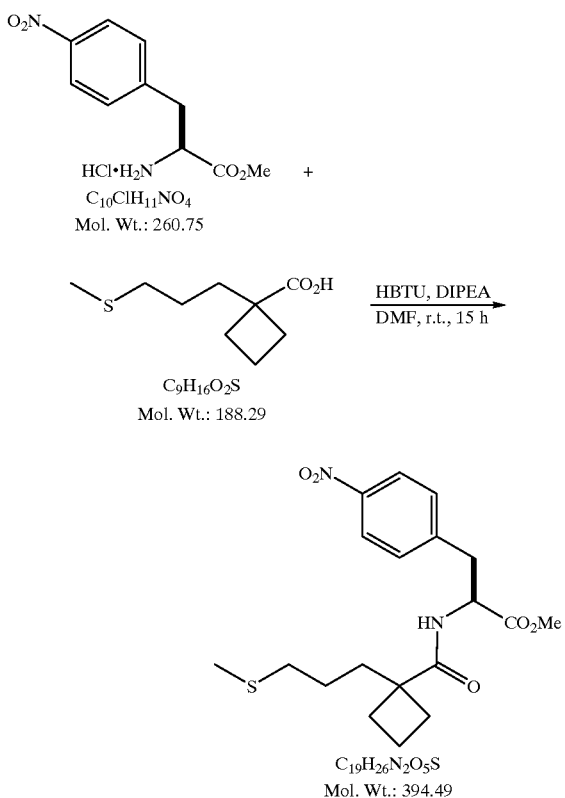

Using the general procedure described in example 45, starting with 4-nitro-L-phenylalanine methyl ester hydrochloride salt and 1-[3-(methylthio)propyl]cyclobutanecarboxylic acid, N-[[1-[3-(methylthio)propyl]cyclobutyl]carbonyl]-4-nitro-L-phenylalanine methyl ester was prepared in 92% yield as an yellow viscous oil. HR MS: Obs. mass, 395.1638. Calcd. mass, 395.1640 (M+H).

Example 68. N-[[1-[3-(methylthio)propylcyclobutyl]thioxomethyl]-4-nitro-L-phenylalanine methyl ester.

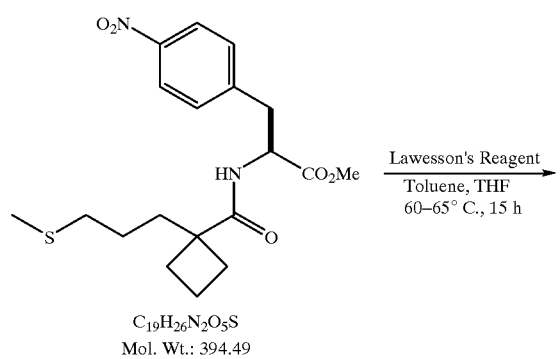

-continued

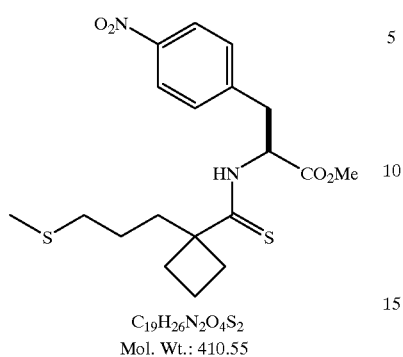

C₁₉H₂₆N₂O₄S₂
Mol. Wt.: 410.55

Using the general procedure described in example 47, starting with 4-nitro-N-[[1-[3-(methylthio)propyl]cyclobutyl]carbonyl]-4-nitro-L-phenylalanine methyl ester, N-[[1-[3-(methylthio)propyl]cyclobutyl]thioxomethyl]-4-nitro-L-phenylalanine methyl ester was prepared in 95% yield as a colorless viscous oil. HR MS: Obs. mass, 411.1408. Calcd. mass, 411.1412 (M+H).

Example 69. 4-amino-N-[[1-[3-(methylthio)propyl]cyclobutyl]thioxomethyl]-L-phenylalanine methyl ester.

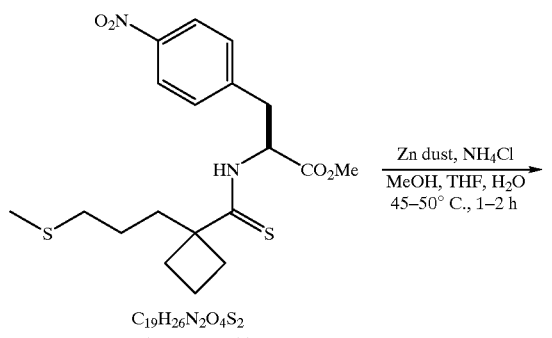

C₁₉H₂₆N₂O₄S₂
Mol. Wt.: 410.55

Zn dust, NH₄Cl
MeOH, THF, H₂O
45–50° C., 1–2 h

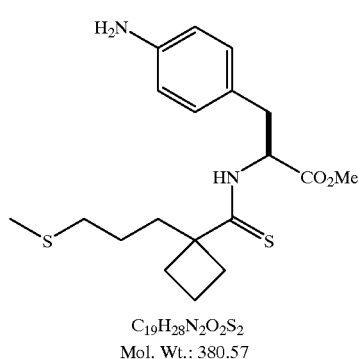

C₁₉H₂₈N₂O₂S₂
Mol. Wt.: 380.57

Using the general procedure described in example 48, starting with N-[[1-[3-(methylthio) propyl]cyclobutyl]thioxomethyl]-4-nitro-L-phenylalanine methyl ester, 4-amino-N-[[1-[3-(methylthio)propyl]cyclobutyl]thioxomethyl]-L-phenylalanine methyl ester was prepared in 97% yield as an hygroscopic yellow solid. HR MS: Obs. mass, 381.1660. Calcd. mass, 381.1671 (M+H).

Example 70. 4-[(2,6-dichlorophenylcarbonyl)amino]-N-[[1-[3-(methylthio) propyl]cyclobutyl]thioxomethyl]-L-phenylalanine methyl ester.

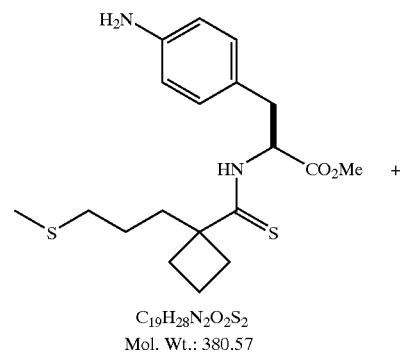

C₁₉H₂₈N₂O₂S₂
Mol. Wt.: 380.57

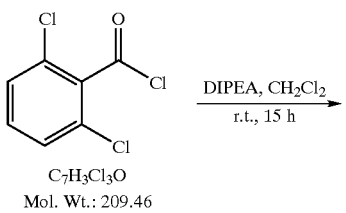

C₇H₃Cl₃O
Mol. Wt.: 209.46

DIPEA, CH₂Cl₂
r.t., 15 h

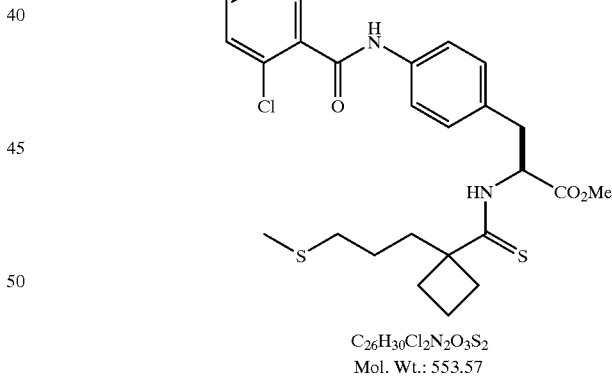

C₂₆H₃₀Cl₂N₂O₃S₂
Mol. Wt.: 553.57

Using the general procedure described in example 49, starting with 4-(amino)-N-[[1-[3-(methylthio)propyl]cyclobutyl]thioxomethyl]-L-phenylalanine methyl ester and 2,6-dichlorobenzoylchloride, 4-[[(2,6-dichlorophenyl)carbonyl]amino]-N-[[1-[3-(methylthio)propyl]cyclobutyl]thioxomethyl]-L-phenylalanine methyl ester was prepared in 83% yield as a colorless solid, mp 184–186° C. HR MS: Obs. mass, 553.1139. Calcd. mass, 553.1153 (M+H).

Example 71. 4-[[(2,6-dichlorophenyl)carbonyl]amino]-N-[[1-[3-(methylthio)propyl]cyclobutyl]-thioxomethyl]-L-phenylalanine.

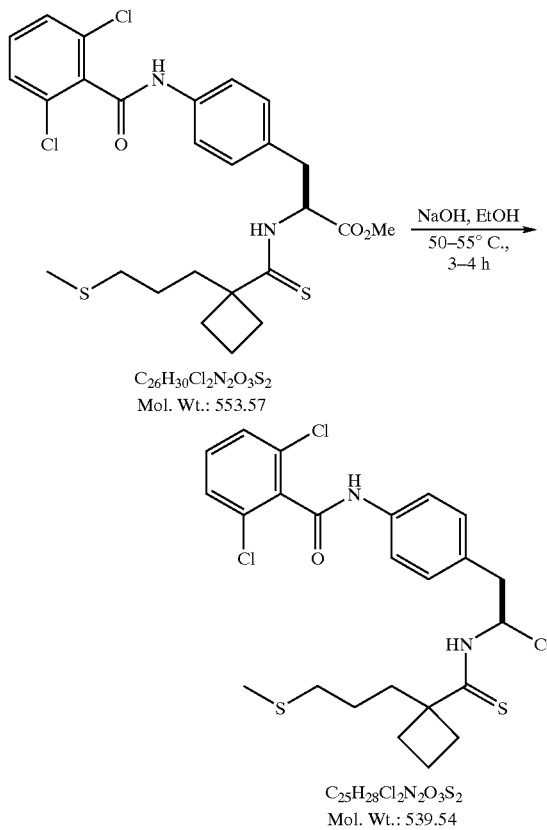

Using the general procedure described in example 50, starting with 4-[[(2,6-dichlorophenyl)carbonyl]amino]-N-[[1-[3-(methylthio)propyl]cyclobutyl]thioxomethyl]-L-phenylalanine methyl ester, 4-[[(2,6-dichlorophenyl)carbonyl]amino]-N-[[1-[3-(methylthio)propyl]cyclobutyl]thioxomethyl]-L-phenylalanine was prepared in 97% yield as a colorless solid, mp 186–188° C. HR MS: Obs. mass, 539.0986. Calcd. mass, 539.0996 (M+H).

Example 72. 1-[3-(methylsulfonyl)propyl]cyclobutanecarboxylic acid ethyl ester.

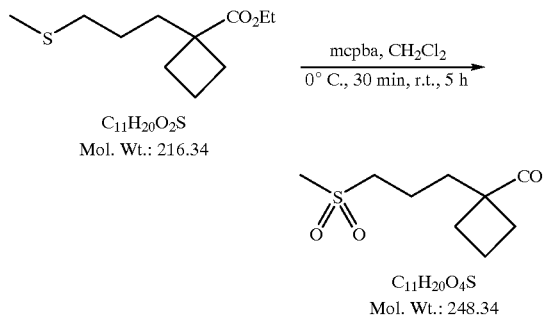

Using the general procedure described in example 46, starting with 1-[3-(methylthio)propyl]cyclobutanecarboxylic acid ethyl ester, 1-[3-(methylsulfonyl)propyl]cyclobutanecarboxylic acid ethyl ester was prepared in 87% yield as a colorless oil. HR MS: Obs. mass, 248.1084. Calcd. mass, 248.1082 (M+).

Example 73. 1-[3-(methylsulfonyl)propyl]cyclobutanecarboxylic acid.

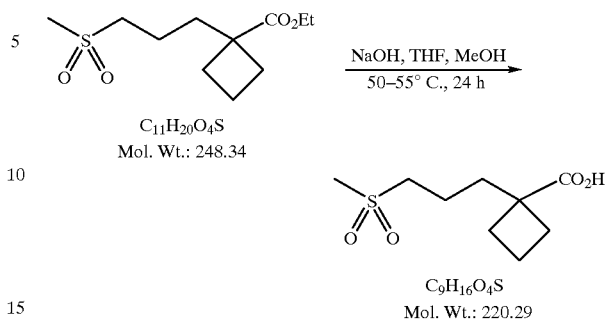

Using the general procedure described in example 43, starting with 1-[3-(methylsulfonyl)propyl]cyclobutanecarboxylic acid ethyl ester, 1-[3-(methylsulfonyl)propyl]cyclobutanecarboxylic acid was prepared in 76% yield as a colorless solid, mp 113–116° C. HR MS: Obs. mass, 220.0770. Calcd. mass, 220.0769 (M+).

Example 74. N-[[1-[3-(methylsulfonyl)propyl]cyclobutyl]carbonyl]-4-nitro-L-phenylalanine methyl ester.

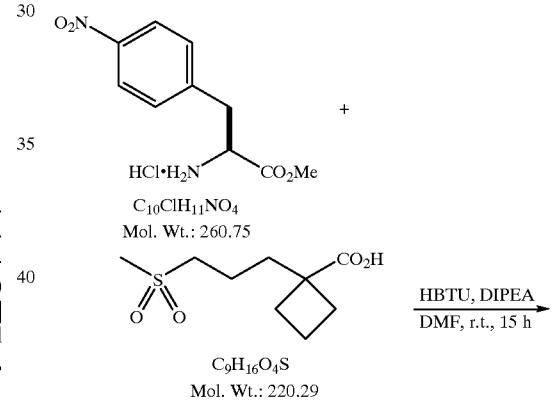

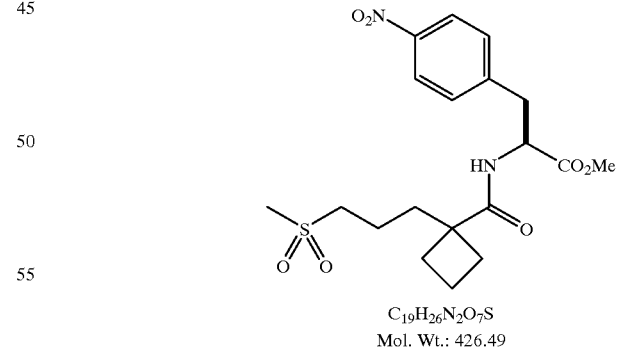

Using the general procedure described in example 45, starting from 4-nitro-L-phenylalanine methyl ester and 1-[3-(methylsulfonyl)propyl]cyclobutane carboxylic acid, N-[[1-[3-(methylsulfonyl) propyl]cyclobutyl]carbonyl]-4-nitro-L-phenylalanine methyl ester was prepared in 76% yield as a colorless amorphous solid. HR MS: Obs. mass, 427.1526. Calcd. mass, 427.1539 (M+H).

Example 75. N-[[1-[3-(methylsulfonyl)propyl] cyclobutyl]thioxomethyl]-4-nitro-L-phenylalanine methyl ester.

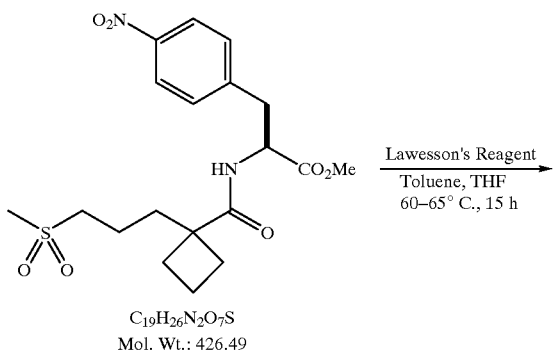

C₁₉H₂₆N₂O₇S
Mol. Wt.: 426.49

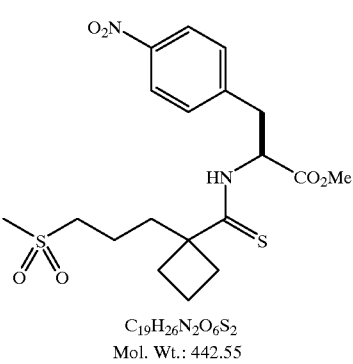

C₁₉H₂₆N₂O₆S₂
Mol. Wt.: 442.55

Using the general procedure described in example 47, starting with N-[[1-[3-(methylsulfonyl)propyl]cyclobutyl] carbonyl]-4-nitro-L-phenylalanine methyl ester, N-[[1-[3-(methylsulfonyl)propyl]cyclobutyl]thioxomethyl]-4-nitro-L-phenylalanine methyl ester was prepared in 88% yield as an yellow sticky solid. HR MS: Obs. mass, 443.1309. Calcd. mass, 443.1310 (M+H).

Example 76. 4-amino-N-[[1-[3-(methylsulfonyl) propyl]cyclobutyl]thioxomethyl]-L-phenylalanine methyl ester.

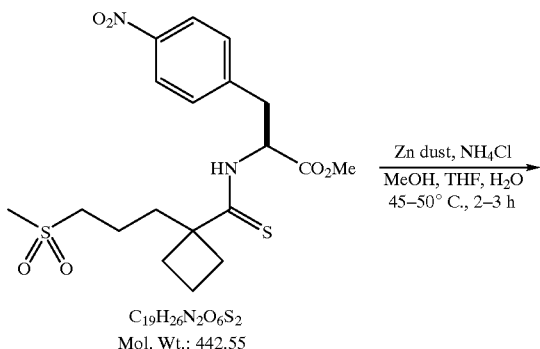

C₁₉H₂₆N₂O₆S₂
Mol. Wt.: 442.55

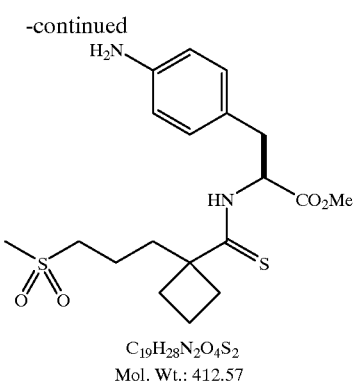

C₁₉H₂₈N₂O₄S₂
Mol. Wt.: 412.57

Using the general procedure described in example 48, starting with N-[[1-[3-(methylsulfonyl)propyl]cyclobutyl] thioxomethyl]-4-nitro-L-phenylalanine methyl ester, 4-amino-N-[[1-[3-(methylsulfonyl)propyl]cyclobutyl] thioxomethyl]-L-phenylalanine methyl ester was prepared in 97% yield as an hygroscopic yellow solid. HR MS: Obs. mass, 413.1556. Calcd. mass, 413.1570 (M+H).

Example 77. 4-[[(2,6-dichlorophenyl)carbonyl] amino]-N-[[1-[3-(methylsulfonyl)-propyl] cyclobutyl]thioxomethyl]-L-phenylalanine methyl ester.

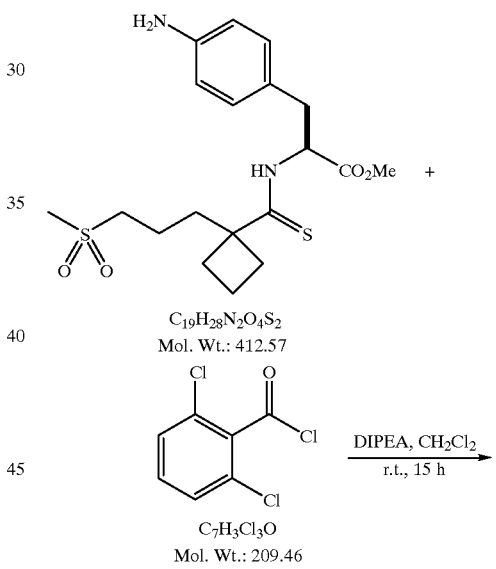

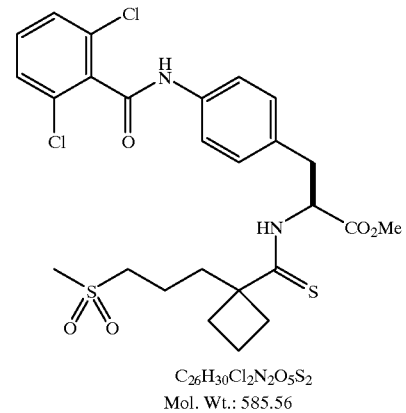

C₂₆H₃₀Cl₂N₂O₅S₂
Mol. Wt.: 585.56

Using the general procedure described in example 49, starting with 4-amino-N-[[1-[3-(methylsulfonyl)propyl]cyclobutyl]thioxomethyl]-L-phenylalanine methyl ester and 2,6-dichlorobenzoyl chloride, 4-[[(2,6-dichlorophenyl)carbonyl]amino]-N-[[1-[3-(methylsulfonyl)propyl]cyclobutyl]thioxomethyl]-L-phenylalanine methyl ester was prepared in 82% yield as a colorless amorphous solid. HR MS: Obs. mass, 585.1056. Calcd. mass, 585.1051 (M+H).

Example 78. 4-[[(2,6-dichlorophenyl)carbonyl]amino]-N-[[1-[3-(methylsulfonyl) propyl]cyclobutyl]thioxomethyl]-L-phenylalanine.

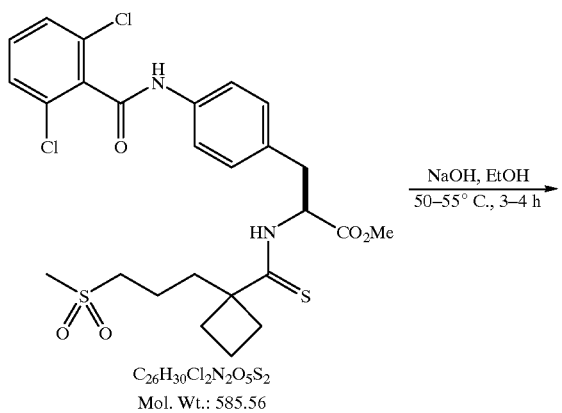

Using the general procedure described in example 50, starting with 4-[[(2,6-dichlorophenyl)carbonyl]amino]-N-[[1-[3-(methylsulfonyl)propyl]cyclobutyl]thioxomethyl]-L-phenylalanine methyl ester, 4-[(2,6-dichlorophenylcarbonyl)amino]-N-[[1-[3-(methylsulfonyl)propyl]cyclobutyl]thioxomethyl]-L-phenylalanine was prepared in 87% yield as an amorphous colorless solid. HR MS: Obs. mass, 571.0894. Calcd. mass, 571.0895 (M+H).

Example 79. 2-chloro-5-(trifluoromethyl)phenol triflate.

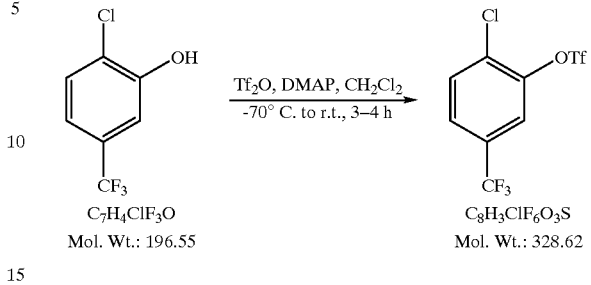

To a solution of 2-chloro-5-(trifluoromethyl)phenol (24.4 mmol, 4.8 g) in dichloromethane (160 mL) was added DMAP (54.0 mmol, 6.7 g) at −70° C. followed by triflic anhydride (36.6 mmol, 10.32 g, 6.16 mL) at −70° C. After the addition was complete, the suspension was stirred for 30 min at this temperature and then warmed to room temperature. After another 3 h, when starting material could not be detected by TLC of the reaction mixture indicated the absence of starting material, the stirred mixture was diluted with H$_2$O (100 mL) and the two layers were separated.

The aqueous layer was extracted with dichloromethane (100 mL)and then the combined dichloromethane extracts were washed with brine. The dried (MgSO$_4$) solution was filtered and evaporated to dryness to give a colorless residue which was purified by silica gel column chromatography (hexane:diethyl ether 4:1) to obtain 6.8 g (85%) of 2-chloro-5-(trifluoromethyl)phenol triflate as a colorless oil HR MS: Obs. mass, 327.9388. Calcd. mass, 327.9392 (M+).

Example 80. 2-chloro-5-(trifluoromethyl)benzoic acid.

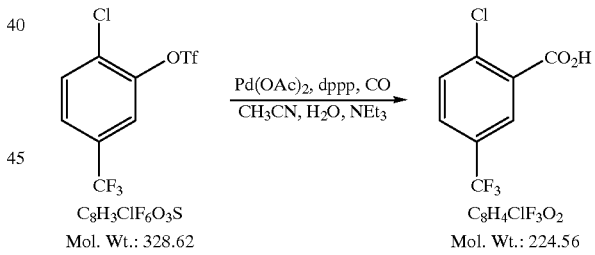

A 250 mL pressure bottle was charged with 2-chloro-5-(trifluoromethyl)phenol triflate (20.6 mmol, 6.76 g), Pd(OAc)$_2$ (1.71 mmol, 384 mg) and dppp (1.71 mmol, 701 mg). The flask was closed with a septum and evacuated three times with argon. Acetonitrile (114 mL), triethylamine (225.3 mmol, 30.7 mL) and water (22.2 mL) were added in succession with the aid of a syringe. The rubber septum was replaced with a teflon lined lid. The flask was pressurized with carbon monoxide (40 psi) and the gas was released. This process was repeated three times and finally the reaction was stirred for 5 min under pressure. The flask was then disconnected from the gas cylinder, immersed in a preheated oil bath (83–85° C.) and stirred for 2 h. The flask was re-pressurized with carbon monoxide and stirred for another 1 h. After the reaction mixture was cooled to room temperature, the pressure was released and it diluted with diethyl ether (250 mL) and 25 mL of 1.0 N NaOH. The sodium salt was extracted into water (2×100 mL). The combined aqueous extracts were acidified with 1.0 N HCl and extracted with diethyl ether (3×100 mL). The combined diethyl ether extracts were washed with brine, dried (MgSO$_4$), filtered and the solution was concentrated in vacuo to furnish a light yellow solid. The solid was dissolved in diethyl ether (100 mL) and extracted with 1.0 N NaOH solution (2×50 mL). The combined aqueous layers were acidified and extracted with diethyl ether (2×100 mL). After the combined organic extracts were washed with brine (100 mL), the dried (MgSO$_4$) solution was filtered and evaporated to dryness to give 1.6 g (35%) of 2-chloro-5-(trifluoromethyl)benzoic acid obtained as a colorless solid, mp 82–83.5° C . HR MS: Obs. mass, 223.9852. Calcd. mass, 223.9851 (M+).

Example 81. 4-[[[(2-chloro-5-(trifluoromethyl) phenyl]carbonyl]amino]-N-[[1-[4-(methylsulfonyl) butyl]cyclobutyl]thioxomethyl]-L-phenylalanine methyl ester.

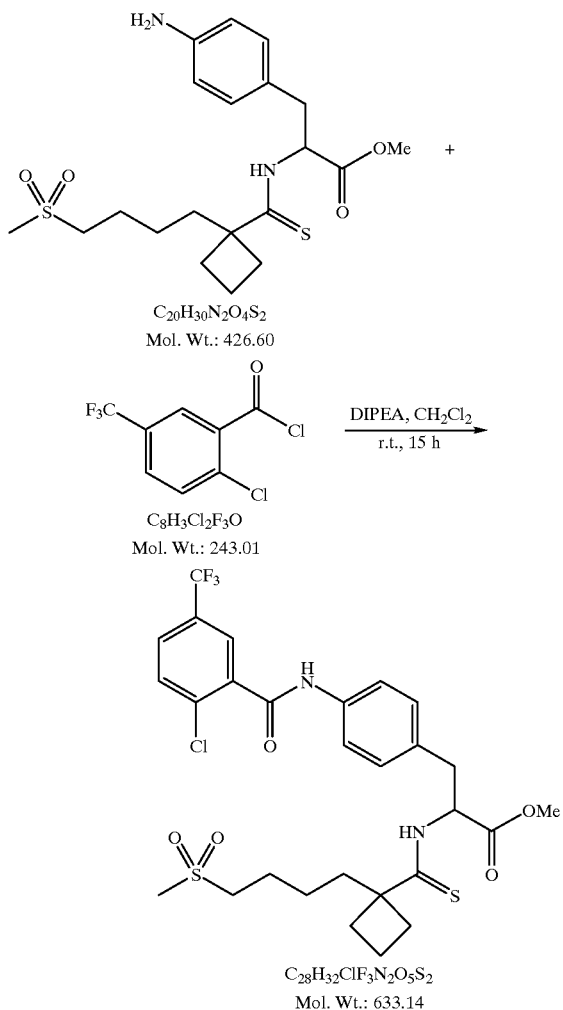

Using the general procedure described in example 52, starting with 4-amino-N-[[1-[4-(methylsulfonyl)butyl] cyclobutyl]thioxomethyl]-L-phenylalanine methyl ester and 2-chloro-5-(trifluoromethyl)benzoic acid, 4-[[[(2-chloro-5-(trifluoromethyl) phenyl]carbonyl]amino]-N-[[1-[4-(methylsulfonyl)butyl]cyclobutyl]thioxomethyl]-L-phenylalanine methyl ester was prepared in 97% yield as a colorless amorphous solid. HR MS: Obs. mass, 633.1477. Calcd. mass, 633.1471 (M+H).

Example 82. 4-[[[(2-chloro-5-(trifluoromethyl) phenyl]carbonyl]amino]-N-[[1-[4-(methylsulfonyl) butyl]cyclobutyl]thioxomethyl]-L-phenylalanine.

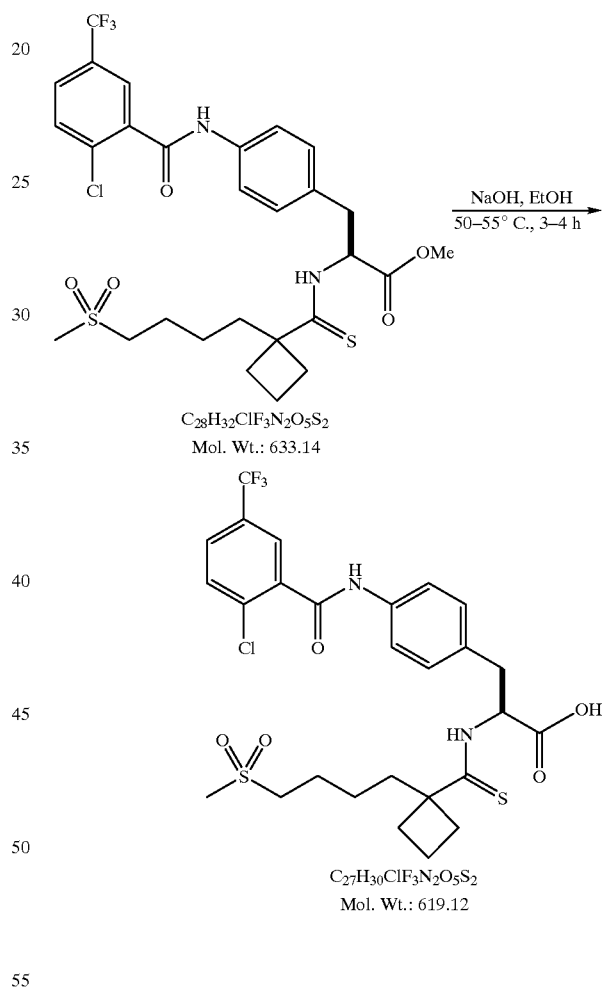

Using the general procedure described in example 50, starting with 4-[[[(2-chloro-5-(trifluoromethyl) phenyl]carbonyl]amino]-N-[[1-[4-(methylsulfonyl)butyl]-cyclobutyl] thioxomethyl]-L-phenylalanine methyl ester, 4-[[[(2-chloro-5-(trifluoromethyl)phenyl]carbonyl]amino]-N- [[1-[4-(methylsulfonyl) butyl]cyclobutyl]thioxomethyl]-L-phenylalanine was prepared in 75% yield as an amorphous colorless solid. HR MS: Obs. mass, 619.1315. Calcd. mass, 619.1318 (M+H).

Example 83. 4-[[[(2,6-dimethyl-4-(trifluoromethyl) pyridin-3-yl]carbonyl]amino]-N-[[1-[4-(methylsulfonyl)butyl]cyclobutyl]thioxomethyl]-L-phenylalanine methyl ester.

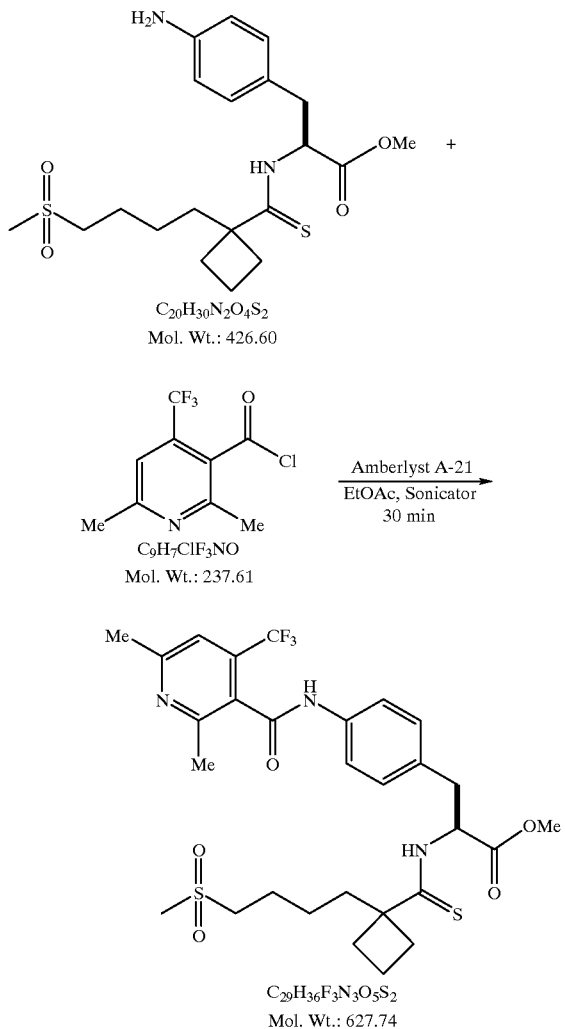

To suspension of 2,6-dimethyl-4-(trifluoromethyl)pyridine-3-carboxylic acid (0.84 mmol, 184 mg) in dichloromethane (10 mL) containing DMF (3 drops) was added dropwise oxalyl chloride (1.14 mmol, 146 mg, 0.1 mL) at 0° C. for 2–3 min. After the addition was complete, the reaction was stirred for 30 min at 0° C. and then allowed to warm to room temperature. The clear solution was stirred for another 2 h at room temperature, then the solvent was removed under reduced pressure and the residue was dried under high vacuum for 1 h. To a mixture of 4-amino-N-[[1-[4-(methylsulfonyl)butyl]cyclobutyl]thioxomethyl]-L-phenylalanine methyl ester (0.7 mmol, 298 mg) and amberlyst A-21 (1.4 mmol, 900 mg) in ethyl acetate (10 mL, stored over 4 Å molecular sieves) in a 4-necked sonicator flask was added a solution of the above prepared acid chloride in ethyl acetate (6 mL) at room temperature. The mixture was subjected for sonication for 30 min and then was partitioned between water (100 mL) and ethyl acetate (100 mL). The separated aqueous layer was extracted with ethyl acetate (50 mL) and the combined extracts were washed brine (100 mL. The dried (MgSO$_4$) ethyl acetate layer was filtered and evaporated to dryness in vacuo and the residue was purified by RP-HPLC to obtain 139 mg (32%) of 4-[[[(2,6-dimethyl-4-(trifluoromethyl)pyridin-3-yl] carbonyl]amino]-N-[[1-[4-(methylsulfonyl)butyl] cyclobutyl]thioxomethyl]-L-phenylalanine methyl ester as an amorphous colorless solid. HR MS: Obs. mass, 628.2122. Calcd. mass, 628.2127 (M+H).

Example 84. 4-[[[(2,6-dimethyl-4-(trifluoromethyl) pyridin-3-yl]carbonyl]amino]-N-[[1-[4-(methylsulfonyl)butyl]cyclobutyl]thioxomethyl]-L-phenylalanine.

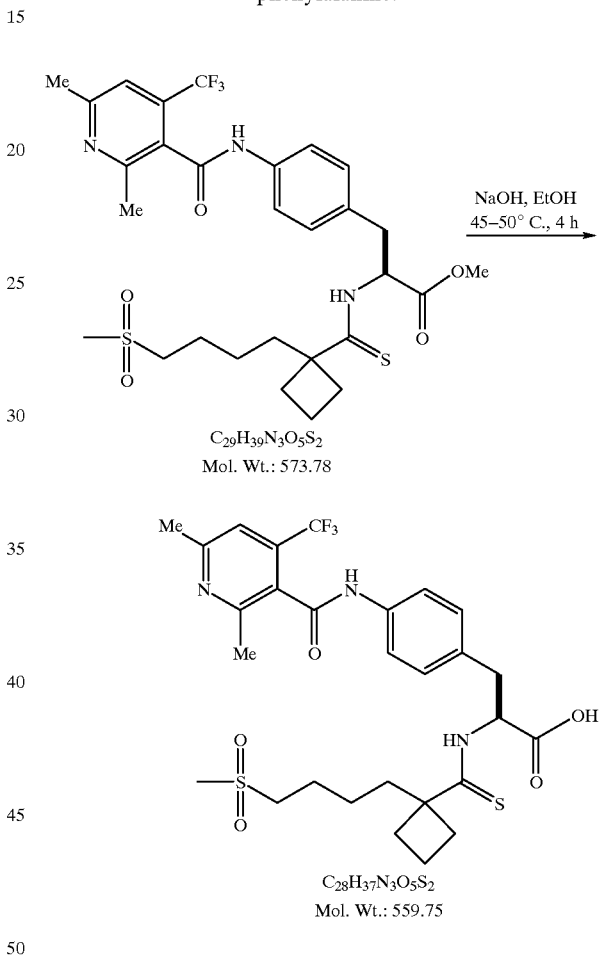

To a suspension of 4-[[[(2,6-dimethyl-4-(trifluoromethyl) pyridin-3-yl]carbonyl]amino]-N-[[1-[4-(methylsulfonyl) butyl]cyclobutyl]thioxomethyl]-L-phenylalanine methyl ester (0.2 mmol, 125 mg) in ethanol (7 mL) was added a 1.0N solution of sodium hydroxide (5.0 mL) at room temperature. Within few minutes the reaction mixture become a clear solution and it was heated to 45–50° C. and stirred for 4 hr, at which time TLC analysis of the mixture indicated the absence of starting material. After the solution was cooled to room temperature, the ethanol was removed in vacuo and the residue was purified by RP-HPLC to obtain 67.5 mg (55%) of 4-[[[(2,6-dimethyl-4-(trifluoromethyl)pyridin-3-yl] carbonyl]amino]-N-[[1-[4-(methylsulfonyl)butyl] cyclobutyl]thioxomethyl]-L-phenylalanine methyl ester as an amorphous colorless solid. HR MS: Obs. mass, 614.1970. Calcd. mass, 614.1970 (M+H).

Example 85. 4-[[(2,6-dichlorophenyl)carbonyl[amino[-N-[(2-bromophenyl)thioxomethyl]-L-phenylalanine.

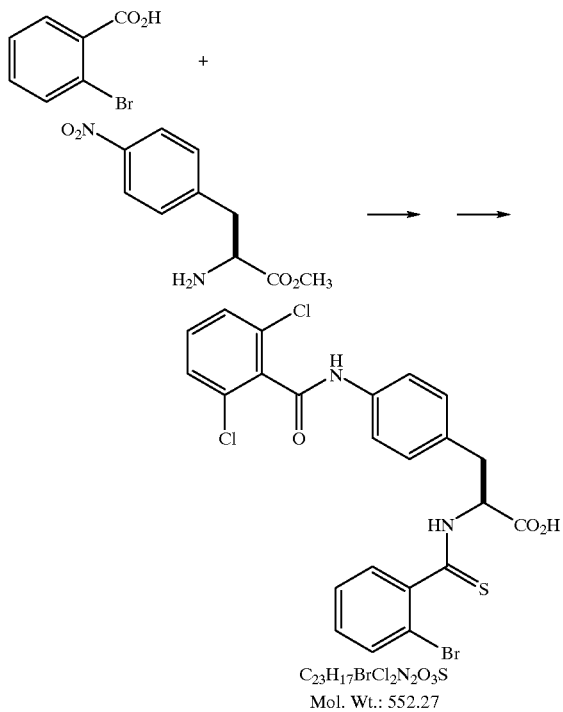

C₂₃H₁₇BrCl₂N₂O₃S
Mol. Wt.: 552.27

Using the method described in examples 35 to 39, and starting with 2-bromobenzoic acid and 4-nitro-L-phenylalanine methyl ester hydrochloride salt, the title compound was prepared. HRMS Obs. mass, 550.9593. Calcd mass, 550.9598 (M+H).

Example 86. 4-[(2S,4R)-3-acetyl-5-oxo-2-phenyl-4-(phenylmethyl)imidazolidin-1-yl]-N-[[4-(methylsulfonyl)butyl]cyclopentyl]thioxomethyl]-L-phenylalanine and 4-[(2R,4R)-3-acetyl-5-oxo-2-phenyl-4-(phenylmethyl)imidazolidin-1-yl]-N-[[4-(methylsulfonyl)butyl]cyclopentyl]thioxomethyl]-L-phenylalanine.

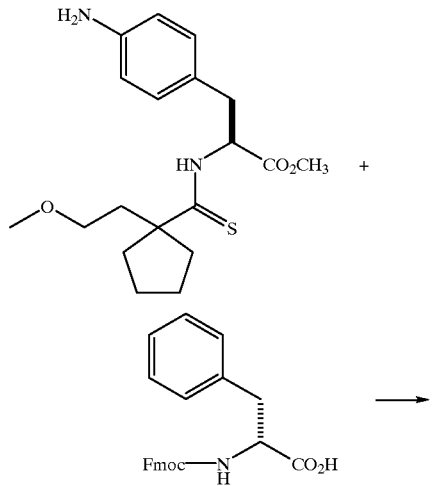

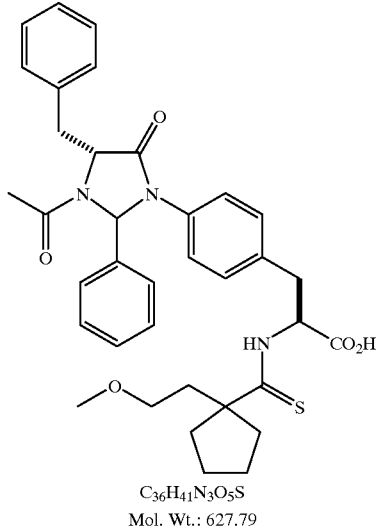

C₃₆H₄₁N₃O₅S
Mol. Wt.: 627.79

Using the procedure described in examples 26 to 29, the title compounds were prepared. The isomers were separated by chromatography at the methyl ester stage. For the 2S,4R isomer, HRMS, Obs. mass, 650.2670. Calcd mass, 650.2665 (M+Na). For the 2R,4R isomer, HRMS, obs. mass, 650.2679. Calcd. mass, 650.2665 (M+Na).

Assays:

1. VLA-4/VCAM-1 Screening Assay

VLA-4 antagonist activity, defined as ability to compete for binding to immobilized VCAM-1, was quantitated using a solid-phase, dual antibody ELISA. VLA-4 (α4β1 integrin) bound to VCAM-1 is detected by a complex of anti-integrin β1 antibody: HRP-conjugated anti-mouse IgG: chromogenic substrate (K-Blue). Initially, this entailed coating 96 well plates (Nunc Maxisorp) with recombinant human VCAM-1 (0.4 μg in 100 μl PBS), sealing each plate and then allowing the plates to stand at 4° C. for ~18 hr. The VCAM-coated plates were subsequently blocked with 250 μl of 1% BSA/0.02% NaN₃ to reduce non-specific binding. On the day of assay, all plates are washed twice with VCAM Assay Buffer (200 μl/well of 50 mM Tris-HCl, 100 mM NaCl, 1 mM MnCl₂, 0.05% Tween 20; pH 7.4). Test compounds are dissolved in 100% DMSO and then diluted 1:20 in VCAM Assay Buffer supplemented with 1 mg/mL BSA (i.e., final DMSO=5%). A series of 1:4 dilutions are performed to achieve a concentration range of 0.005 nM–1.563 μM for each test compound. 100 μl per well of each dilution is added to the VCAM-coated plates, followed by 10 μl of Ramos cell-derived VLA-4. These plates are sequentially mixed on a platform shaker for 1 min, incubated for 2 hr at 37° C., and then washed four times with 200 μl/well VCAM Assay Buffer. 100 μl of mouse anti-human integrin β1 antibody is added to each well (0.6 μg/mL in VCAM Assay Buffer+1 mg/mL BSA) and allowed to incubate for 1 hr at 37° C. At the conclusion of this incubation period, all plates are washed four times with VCAM Assay Buffer (200 μl/well). A corresponding second antibody, HRP-conjugated goat anti-mouse IgG (100 μl per well @ 1:800 dilution in VCAM Assay Buffer+1 mg/mL BSA), is then added to each well, followed by a 1 hr incubation at room temperature and concluded by three washes (200 μl/well) with VCAM Assay Buffer. Color development is initiated by addition of 100 μl K-Blue per well (15 min incubation, room temp) and terminated by addition of 100 μl Red Stop Buffer per well. All plates are then read in a UV/V is spectrophotometer at 650 nM. Results are calculated as % inhibition of total binding (i.e., VLA-4+VCAM-1 in the absence of test compound). Selected data for compounds of this invention are shown in the table below:

2. Ramos (VLA-4) / VCAM-1 Cell-Based Screening Assay Protocol

Materials:

Soluble recombinant human VCAM-1 (mixture of 5- and 7-Ig domain) was purified from CHO cell culture media by immunoaffinity chromatography and maintained in a solution containing 0.1 M Tris-glycine (pH 7.5), 0.1 M NaCl, 5 mM EDTA, 1 mM PMSF, 0.02% 0.02% $NaN_3$ and 10 μg/mL leupeptin. Calcein-AM was purchased from Molecular Probes Inc.

Methods:

VLA-4 (α4β1 integrin) antagonist activity, defined as ability to compete with cell-surface VLA-4 for binding to immobilized VCAM-1, was quantitated using a Ramos-VCAM-1 cell adhesion assay. Ramos cells bearing cell-surface VLA-4, were labeled with a fluorescent dye (Calcein-AM) and allowed to bind VCAM-1 in the presence or absence of test compounds. A reduction in fluorescence intensity associated with adherent cells (% inhibition) reflected competitive inhibition of VLA-4 mediated cell adhesion by the test compound. Initially, this entailed coating 96 well plates (Nunc Maxisorp) with recombinant human VCAM-1 (100 ng in 100 μl PBS), sealing each plate and allowing the plates to stand at 4° C. for ~18 hr. The VCAM-coated plates were subsequently washed twice with 0.05% Tween-20 in PBS, and then blocked for 1 hr (room temperature) with 200 μl of Blocking Buffer (1% BSA/ 0.02% thimerosal) to reduce non-specific binding. Following the incubation with Blocking Buffer, plates were inverted, blotted and the remaining buffer aspirated. Each plate was then washed with 300 μl PBS, inverted and the remaining PBS aspirated.

Test compounds were dissolved in 100% DMSO and then diluted 1:25 in VCAM Cell Adhesion Assay Buffer (4 mM $CaCl_2$, 4 mM $MgCl_2$ in 50 mM TRIS-HCl, pH 7.5) (final DMSO=4%). A series of eight 1:4 dilutions were performed for each compound (general concentration range of 1 nM–12,500 nM). 100 μl/well of each dilution was added to the VCAM-coated plates, followed by 100 μl of Ramos cells (200,000 cells/well in 1% BSA/PBS). Plates containing test compounds and Ramos cells were allowed to incubate for 45 min at room temperature, after which 165 μl/well PBS was added. Plates were inverted to remove non-adherent cells, blotted and 300 μl/well PBS added. Plates were again inverted, blotted and the remaining buffer gently aspirated. 100 μl Lysis Buffer (0.1% SDS in 50 mM TRIS-HCl, pH 8.5) was added to each well and agitated for 2 min on a rotary shaking platform. The plates were then read for fluorescence intensity on a Cytofluor 2300 (Millipore) fluorescence measurement system (excitation=485 nm, emission=530 nm). The results are shown in the following table:

3. MadCAM RPMI 8866 Cell Based Assay

MadCAM binding activity was quantified using an RPMI 8866 cell-based assay. RPMI 8866 cells bearing cell surface MadCAM were labelled with fluorescent dye (calcein AM) and allowed to bind MadCAM in the presence or absence of test compounds. A reduction in fluoresence intensity associated with adherent cells (% inhibition) reflects competitive inhibition of MadCAM mediated cell adhesion by the test compound. Initially, this entailed coating 96 well plates (Nunc F96 Maxisorp) with 25 ng/well of MadCAM (100 μl/well in coating buffer: 10 mM carbonate/bicarbonate buffer, 0.8 g/L sodium carbonate, 1.55 g/L sodium bicarbonate, adjusted to pH 9.6 with 1N HCL), sealing and wrapping each plate and refrigerating the plates for at least 24 hrs. The MadCAM-coated plates were subsequently washed twice with 0.05% Tween-20 in PBS, and then blocked for at least 1 hr. at room temperature with of blocking buffer (1% nonfat dry milk in PBS) to reduce non-specific binding. Following the incubation with blocking buffer, plates were washed with PBS, hand blotted, and the remaining liquid aspirated.

RPMI 8866 cells ($2\times10^6$ cells/ml×10 ml. per plate× number of plates) were transferred to a 50 ml centrifuge tube filled with PBS and spun at 200×g for 8 minutes, after which the PBS is poured off and the pellet resuspended to $10\times10^6$ cells/ml in PBS. Calcein (diluted with 200 μl DMSO from a 5 mg/ml frozen stock) was added to the cells at 5 μl/ml PBS. After incubation at 37 degrees C. for 30 min. in the dark, the cells were washed in PBS and resuspended at 2×106 cells/ml in cell buffer (RPMI 1640 medium (no additives)).

Test compounds were dissolved in 100% DMSO and then diluted 1:25 in binding buffer (1.5 mM $CaCl_2$, 0.5 mM $MnCl_2$ in 50 mM TRIS-HCl, adjusted to pH 7.5 with NaOH). Remaining dilutions were into dilution buffer (4% DMSO in binding buffer—2% DMSO final when diluted 1:2 in wells). A series of dilutions were performed for each compound tested. 129 μl of binding buffer was placed in the first row of wells in the MadCAM-coated plates. 100 μl/well of dilution buffer was added to the remaining wells, followed by 5.4 μl of each test compound in the appropriate dilution (in triplicate). 100 μl of cells (200,000 cells/well) were added. Control wells contained 100 μl dilution buffer+ 100 μl cell buffer, and 100 μl dilution buffer+100 μl cell buffer. Plates were allowed to incubate for 45 min at room temperature, after which 150 μl/well PBS was added. Plates were inverted to remove non-adherent cells, blotted and 200 μl/well PBS added. Plates were again inverted, blotted and the remaining buffer gently aspirated. 100 μl PBS was added to each well. The plates were then read for fluorescence intensity on a fluorescence measurement system (excitation=485 nm, emission=530 nm, sensitivity=2). A linear regression analysis was performed to obtain the $IC_{50}$ of each compound. The results are shown in the following table:

| Example | ELISA $IC_{50}$ nM (VLA/VCAM) | Ramos $IC_{50}$ | RPMI $IC_{50}$ |
|---|---|---|---|
| 3 | 4.0 | 66.5 | |
| 10 | 1.5 | 33 | |
| 11 | 5.6 | 42.5 | |
| 18 | 0.47 | 60 | |
| 25 | 6.0 | 101 | |
| 29 | | 220 | |
| 34 | | 4,180 | |
| 39 | | 784 | |
| 50 | | 30 | |
| 53 | | 148 | |
| 62 | | 8 | 8.7 |
| 64 | | 87 | |
| 71 | | 926 | |
| 78 | | 341 | |
| 82 | | | |
| 84 | | 5.5 | 83 |

Example 4. Acute airway inflammation in the atopic primate.

Airway inflammation in the monkey was determined using a modification of the protocol described by Turner et al. (Turner et al., 1994). Adult male cynomolgus monkeys (*Macaca fascicularis,* Hazelton Labs, Denver, Pa.) weighing between 3.6–5.8 kg were used in these studies. All animals exhibited positive skin and airway responses to Ascaris suum antigen and had at least a 3-fold increase in the sensitivity to methacholine (MCh) when subjected to an aerosol of ascaris extract.

On the day of each experiment the animals were anesthetized with ketamine hydrochloride, 12 mg/kg, and xylazine, 0.5 mg/kg, intubated with a cuffed endotracheal tube (3 mm, Mallinckrodt Medical, St. Louis, Mo.), then seated in an upright position in a specially designed Plexiglass chair (Plas-Labs, Lansing, Mich.). The endotracheal tube was connected to a heated Fleisch pneumotachograph. Airflow was measured via a Validyn differential pressure transducer (DP 45-24) that was attached to the pneumotachograph. Transpulmonary pressure was measured via a second Validyne transducer (DP 45-24) connected between a sidearm of the tracheal cannula and a 18-gauge intrapleural needle inserted in the intercostal space located below the left nipple. Recordings of pressure and flow and the calculation of $R_L$ were made using the Modular Instruments data acquisition system as described above. Baseline $R_L$ was measured for all animals on the day of each experiment and had an average value of about 0.04 cmH$_2$O/ml/sec.

Protocol

Airway inflammation was induced by exposing the animal to an aerosol of *A. Suum* extract for 60 sec. The aerosol was delivered via a nebulizer (De Vilbiss Model 5000, Healt Care Inc., Somerset, Pa.) that was attached to the endotracheal tube. The concentration of extract was predetermined for each animal (500 to 50,000 PNU) and caused at least a doubling in the airway resistance. At 24 hour after the antigen challenge, the animals were anesthetized as described previously and placed on a stainless steel table. Airway inflammation was assessed by inserting a pediatric bronchoscope into the airway lumen down to about the 4 or 5$^{th}$ generation bronchi and gently lavaging with 3 X 2 ml aliquots of sterile Hanks Balanced Salt Solution. The recovered lavage fluid then was analyzed for the total cell and differential cell counts using standard hematological techniques.

Drug Treatment

The animals received drug or a vehicle, p.o., administered 2 hours prior to antigen challenge. The compound of example 1 caused a significant decrease in the number and percent of inflammatory cells present in the lavage fluid relative to vehicle treated control animals.

What is claimed is:

1. A compound of the formula:

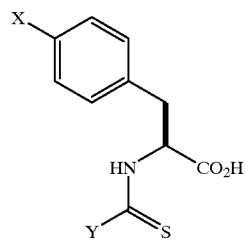

wherein x is

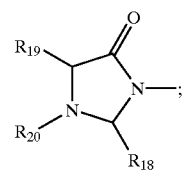

X-3

$R_{18}$ is aryl, heteroaryl, aryl lower alkyl, heteroaryl lower alkyl;

$R_{19}$ is substituted or unsubstituted lower alkyl, aryl, heteroaryl, arylalkyl, heteroaryl alkyl, and $R_{20}$ is substituted or unsubstituted lower alkanoyl or aroyl;

Y is a ring of the formula

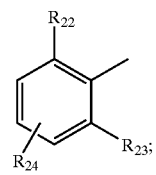

Y-1

$R_{22}$ and $R_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen, and $R_{24}$ is hydrogen, lower alkyl, lower alkoxy, aryl, nitro, cyano, lower alkyl sulfonyl, or halogen;

or Y is a group of the formula:

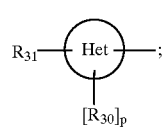

Y-2

Het is a five or six membered heteroaromatic ring bonded via a carbon atom wherein said ring contains one, two or three heteroatoms selected from the group consisting of N, O and S and $R_{30}$ and $R_{31}$ are independently hydrogen, lower alkyl, cycloalkyl, halogen, cyano, perfluoroalkyl, or aryl and at least one of $R_{30}$ and $R_{31}$ is adjacent to the point of attachment; p is an integer of from 0 to 1;

or Y is a ring of the formula

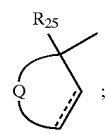

Y-3

$R_{25}$ is lower alkyl, unsubstituted or fluorine substituted lower alkenyl, or a group of formula $R_{26}$—(CH$_2$)e—, $R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula $-NR_{28}R_{29}$;

$R_{28}$ is H or lower alkyl; $R_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylaminocarbonyl, or $R_{28}$ and $R_{29}$ taken together from a 4, 5 or 6-membered saturated carbacyclic ring optionally containing one heteroatom selected from O, S, and N; with the carbon atoms in the ring being unsubstituted or substituted by lower alkyl or halogen;

Q is $-(CH2)_fO-$, $-(CH_2)_fS-$, $-(CH_2)_fN(R_{27})-$, or $-(CH_2)_f-$, $R_{27}$ is H, lower alkyl, aryl, lower alkanoyl, aroyl or lower alkoxycarbonyl;

e is an integer from 0 to 4, and f is an integer from 0 to 3; and the dotted bond is optionally hydrogenated;

or pharmaceutically acceptable salts and esters thereof.

2. The compound of claim 1 wherein $R_{18}$ is phenyl.

3. The compound of claim 1 wherein $R_{19}$ is lower alkyl which is is unsubstituted or substituted by pyridyl or phenyl.

4. The compound of claim 1 wherein $R_{20}$ is substituted or unsubstituted lower alkanoyl.

5. A compound of claim 1 wherein $R_{18}$ is phenyl, $R_{19}$ is lower alkyl which is unsubstituted or substituted by pyridyl or phenyl and $R_{20}$ is lower alkanoyl.

6. The compound of claim 1 wherein $R_{18}$ is phenyl which is unsubstituted or substituted by halogen or lower alkoxy; $R_{19}$ is phenyl lower alkyl which is unsubstituted or substituted by lower alkoxy, pyridyl lower alkyl, or lower alkyl; and $R_{20}$ is substituted or unsubstituted lower alkanoyl.

7. The compound of claim 6 wherein X is selected from the group of

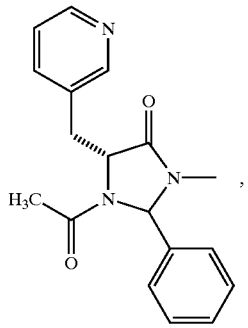

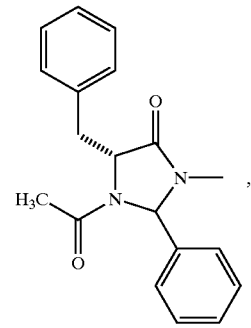

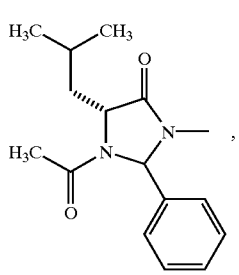

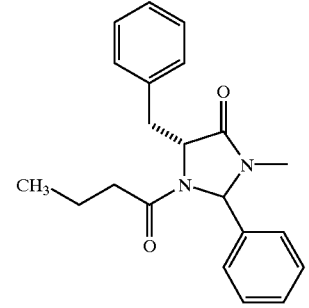

-continued

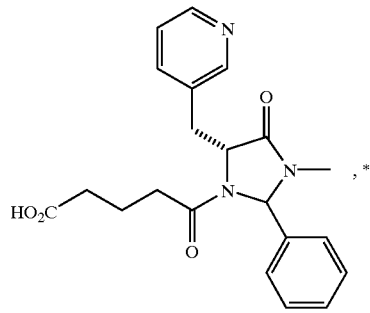

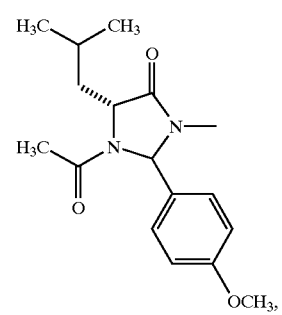

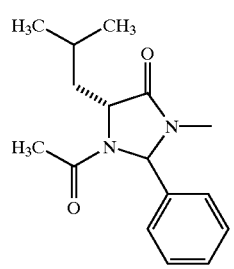

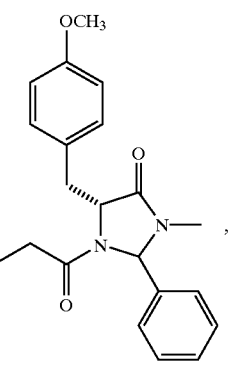

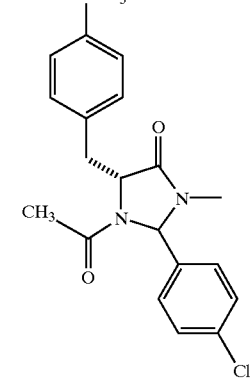

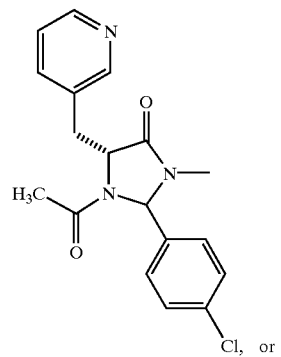

-continued

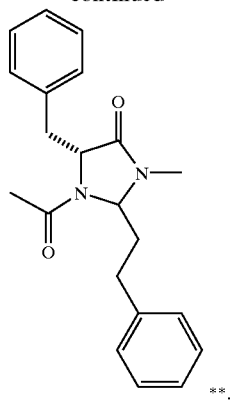

8. The compound of claim 1 wherein Y is a group of formula

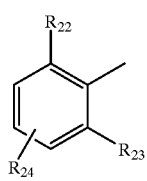

Y-1 and X, $R_{22}$, $R_{23}$, and $R_{24}$ are as above.

9. The compound of claim 8 wherein $R_{22}$ and $R_{23}$ are lower alkyl, trifluoromethyl, or halogen and $R_{24}$ is hydrogen, lower alkyl, lower alkoxy, or halogen.

10. The compound of claim 9 wherein Y is

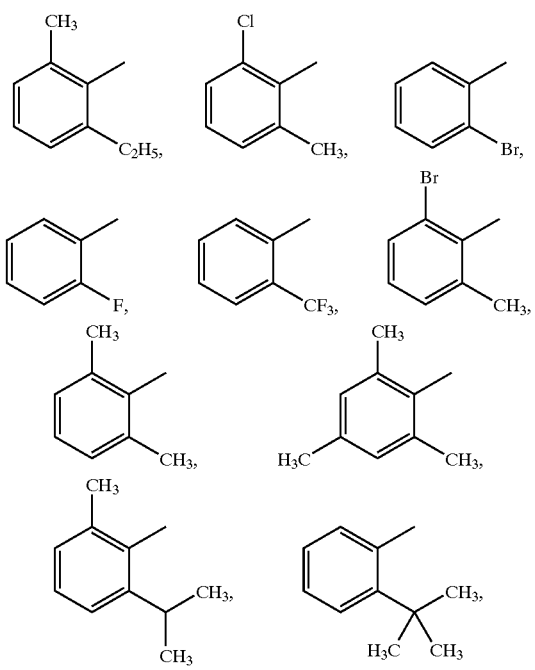

11. The compound of claim 1 wherein Y is a group of the formula Y-2.

12. The compound of claim 11 wherein Het is a 6 membered heteroaromatic ring.

13. The compound of claim 12 wherein the heteroatom is N.

14. The compound of claim 13 wherein Y-2 is

15. The compound of claim 1 wherein Y is a ring of the formula and Y, $R_{25}$ and Q are as above, and the dotted bond can be optionally hydrogenated.

16. The compound of claim 15 wherein Y is

-continued

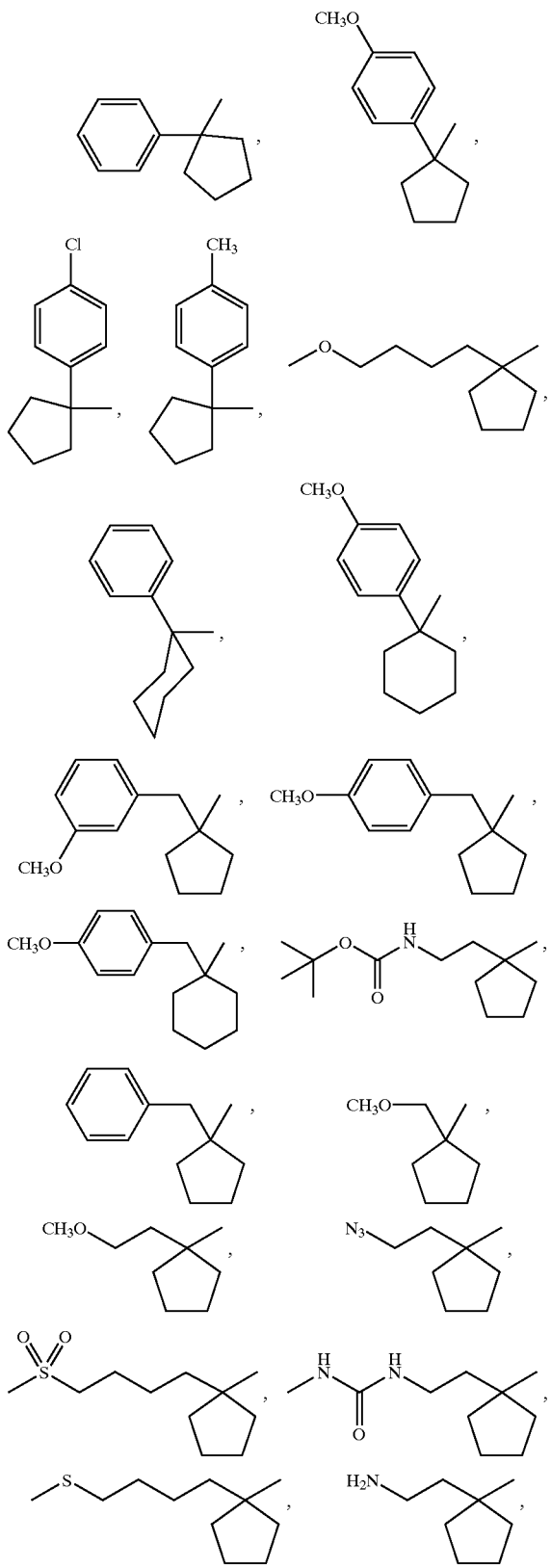

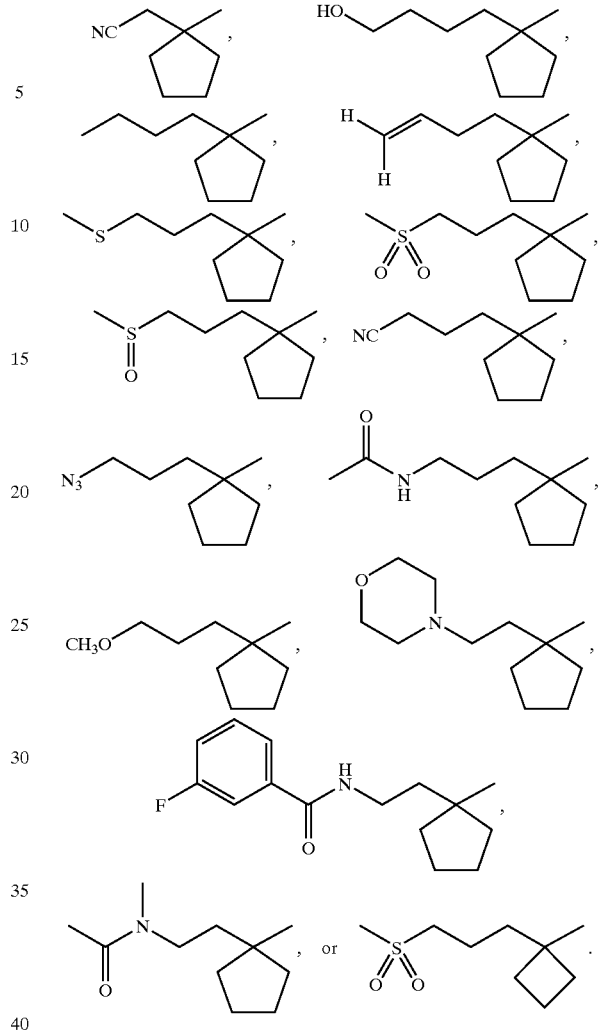

17. The compound of claim 15 wherein $R_{19}$ is pyridinyl lower alkyl or phenyl lower alkyl; $R_{20}$ is lower alkanoyl and $R_{18}$ is phenyl.

18. The compound of claim 17 wherein the ring Y-3 is a four to six membered cycloalkyl ring with $R_{25}$ being $R_{26}$—$CH_2$)e—, e is 2 to 4, $R_{26}$ being alkoxy, lower alkyl sulfonyl, loweralkylthio or $NHR_{29}$ where $R_{29}$ is loweralkoxycarbonyl or loweralkylaminocarbonyl, and the dotted bond is optionally hydrogenated.

19. The compound of claim 18 wherein $R_{26}$ is methoxy, methyl sulfonyl, or methyl thio.

20. A compound of claim 19 which is 4-[(2S,4R)-3-acetyl-2-phenyl-4-[(3-phenyl)methyl]-5-oxo-imidazolidin-1-yl]-N-[[(4-methylsulfonyl)butyl]cyclopentyl]thioxomethyl]-L-phenylalanine.

21. A compound of claim 19 which is 4-[(2R,4R)-3-acetyl-2-phenyl-4-[(3-phenyl)methyl]-5-oxo-imidazolidin-1-yl]-N-[[(4-methylsulfonyl)butyl]cyclopentyl]thioxomethyl]-L-phenylalanine.

* * * * *

UNITED STATES PATENT AND TRADEMARK OFFICE
CERTIFICATE OF CORRECTION

PATENT NO.   : 6,479,666 B2
DATED        : November 12, 2002
INVENTOR(S)  : Kenneth G. Hull et al.

It is certified that error appears in the above-identified patent and that said Letters Patent is hereby corrected as shown below:

<u>Title page,</u>
Please add the following:
-- Related U.S. Application Data
Division of Ser. No. 505,903, Feb. 17, 2002, now USPN 6,288,267. --

Signed and Sealed this

Seventeenth Day of June, 2003

JAMES E. ROGAN
*Director of the United States Patent and Trademark Office*